(12) United States Patent
Boer et al.

(10) Patent No.: US 12,285,033 B2
(45) Date of Patent: *Apr. 29, 2025

(54) STEVIOL GLYCOSIDE TRANSPORT

(71) Applicant: DSM IP ASSETS B.V., Heerlen (NL)

(72) Inventors: Viktor Marius Boer, Echt (NL);
Priscilla Zwartjens, Echt (NL); Eric Van Den Berg, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 0 days.

This patent is subject to a terminal disclaimer.

(21) Appl. No.: 18/428,486

(22) Filed: Jan. 31, 2024

(65) Prior Publication Data

US 2024/0237688 A1 Jul. 18, 2024

Related U.S. Application Data

(60) Continuation of application No. 17/512,368, filed on Oct. 27, 2021, now Pat. No. 11,925,193, which is a division of application No. 15/751,674, filed as application No. PCT/EP2016/069356 on Aug. 15, 2016, now Pat. No. 11,297,862.

(60) Provisional application No. 62/204,702, filed on Aug. 13, 2015.

(51) Int. Cl.
| | |
|---|---|
| *C12N 1/16* | (2006.01) |
| *A23L 2/60* | (2006.01) |
| *A23L 27/30* | (2016.01) |
| *C07K 14/39* | (2006.01) |
| *C07K 14/395* | (2006.01) |
| *C07K 14/40* | (2006.01) |
| *C12N 9/24* | (2006.01) |
| *C12P 15/00* | (2006.01) |
| *C12P 19/56* | (2006.01) |

(52) U.S. Cl.
CPC ............... *A23L 27/36* (2016.08); *A23L 2/60* (2013.01); *C07K 14/39* (2013.01); *C07K 14/395* (2013.01); *C07K 14/40* (2013.01); *C12N 1/16* (2013.01); *C12N 9/2402* (2013.01); *C12P 15/00* (2013.01); *C12P 19/56* (2013.01)

(58) Field of Classification Search
CPC ............. C12N 1/20; C12N 9/88; C07K 14/40
See application file for complete search history.

(56) References Cited

U.S. PATENT DOCUMENTS

| | | | | |
|---|---|---|---|---|
| 11,297,862 | B2 * | 4/2022 | Boer | C12P 15/00 |
| 2015/0031868 | A1 | 1/2015 | Lehmann et al. | |
| 2016/0153017 | A1 | 6/2016 | Van Der Hoeven et al. | |
| 2016/0160257 | A1 | 6/2016 | Broers et al. | |
| 2016/0177360 | A1 | 6/2016 | Boer et al. | |

FOREIGN PATENT DOCUMENTS

| | | |
|---|---|---|
| CN | 103732753 A | 4/2014 |
| WO | 2004026043 A1 | 4/2004 |
| WO | 2004032648 A1 | 4/2004 |
| WO | 2013110673 A1 | 8/2013 |
| WO | 2014122328 A1 | 8/2014 |
| WO | 2014191581 A2 | 12/2014 |
| WO | 2015/007748 A1 | 1/2015 |
| WO | 2015011209 A1 | 1/2015 |

OTHER PUBLICATIONS

International Search Report issued in counterpart International Application No. PCT/EP2016/069357, mailed on Nov. 18, 2016.
Dujon et al., "Genome evolution in yeasts" Database, Uniprot: Q6c4M7. (Aug. 16, 2004) p. 1.
Bowie, J.U. et al., "A method to identify protein sequences that fold into a known three-dimensional structure", Science, Jul. 12, 1991, pp. 164-170, vol. 253, No. 5016.
Chothia, Cyrus et al., "The relation between the divergence of sequence and structure in proteins", The EMBO Journal, 1986, pp. 823-826, vol. 5, No. 4.
Ng, Pauline C. et al., "Predicting Deleterious Amino Acid Substitutions", Genome Research, 2001, pp. 863-874, vol. 11.
Henikoff, Steven et al., "Amino acid substitution matrices from protein blocks", Proceedings of the National Academy of Sciences of the United States of America, Nov. 1992, pp. 10915-10919, vol. 89.
Ho, Steffan N. et al., "Site-directed mutagenesis by overlap extension using the polymerase chain reaction", Gene, Apr. 15, 1989, pp. 51-59, vol. 77, No. 1.
Huelsenbeck, John P. et al., "Bayesian analysis of amino acid substitution models", Philosophical Transactions of the Royal Society B, Oct. 7, 2008, Abstract.
Landt, Olfert et al., "A general method for rapid site-directed mutagenesis using the polymerase chain reaction", Gene, 1990, pp. 125-128, vol. 96, No. 1.
Ng, Pauline C. et al., "Predicting the Effects of Amino Acid Substitutions on Protein Function", Annual Review of genomics and Human Genetics, 2006, pp. 61-80, vol. 7.
Taylor, W.R., "Pattern matching methods in protein sequence comparison and structure prediction", Protein Engineering, Design and Selection, Jul. 1988, pp. 77-86, vol. 2, No. 2.
Villoutreix, Bruno, "Mutations or Variations", VLS3D.com, Sep. 15, 2020.

(Continued)

*Primary Examiner* — Tekchand Saidha
(74) *Attorney, Agent, or Firm* — McBee, Moore & Vanik IP, LLC

(57) ABSTRACT

A recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

13 Claims, 21 Drawing Sheets

Specification includes a Sequence Listing.

(56) References Cited

OTHER PUBLICATIONS

Muller, Tobias et al., "Estimating Amino Acid Substitution Models: A Comparison of Dayhoff's Estimator, the Resolvent Approach and a Maximum Likelihood Method", Molecular Biology and Evolution, Jan. 2002, pp. 8-13, vol. 19, No. 1.
Kruskal, Joseph, "An Overview of Sequence Comparison: Time Warps, String Edits, and Macromolecules", SIAM Review, Apr. 1983, p. 201, vol. 25, No. 2.
Guo, H., et al., "Protein to Random Amino Acid Change," PNAS (2004), vol. 101, No. 21: 9205-9210.
Mottram, Donal S., et al., "Acrylamide is formed in the Maillard reaction," Nature, (2002), vol. 419, 448-449.
Tareke, E. et al.,"Acrylamide: A Cooking Carcinogen?", Chemical Research in Toxicity, (2000), vol. 13, 517-522.
Wang, et al., "Pathway mining-based integration of critical enzyme parts for de novo biosynthesis of steviolglycosides sweetener in *Escherichia coli*," Cell Research, v. 26: pp. 258-261 (Sep. 11, 2015).

\* cited by examiner pHYPO-KAH/HYG-R PCR product
4614 bp

```
SEQUENCE LISTING

Sequence total quantity: 34
SEQ ID NO: 1            moltype = DNA   length = 1422
FEATURE                 Location/Qualifiers
misc_feature            1..1422
                        note = UGT2_1a CpO for Y. lipolitica
source                  1..1422
                        mol_type = other DNA
                        organism = synthetic construct
SEQUENCE: 1
atggccacct ccgactccat tgtcgacgac cgaaagcagc tgcacgttgc caccttcccc   60
tggctcgcct ttggccacat tctgccctac ctccagctct ccaagctcat tgctgagaag  120
ggccacaagg tttctttcct gtccaccacc cgaaacatcc agcgactctc ctcccacatc  180
tctcctctca tcaacgttgt ccagctcacc ctcccccgag tccaggagct ccccgaggat  240
gccgaggcca ccactgatgt ccaccccgag gacatcccct acctcaagaa ggcctccgac  300
ggtctgcagc ccgaggtcac ccgattcctc gagcagcact ctcccgactg gatcatctac  360
gactacaccc actactggct ccccctccatt gctgcttctc tcggtatctc tcgagcccac  420
ttctccgtca ccaccccctg ggccattgct tacatgggcc cctctgctga cgccatgatc  480
aacggttccg acggccgaac caccgtcgag gatctcacca ccctcccaa gtggttcccc  540
ttccccacca aggtctgctg gcgaaagcac gatctcgccc gactcgtccc ctacaaggcc  600
cccggtatct ccgacggtta ccgaatgggc ctggttctca agggctccga ctgtctgctc  660
tccaagtgct accacgagtt tggtacccag tggctccccc tgctcgagac tctgcaccag  720
gtcccgttg tcccgtcgg tctgctccct cccgagatcc ccggtgacga aggacgag    780
acttgggttt ccatcaagaa gtggctcgac ggcaagcaga agggctccgt cgtctacgtt  840
```

```
gctctcggct ccgaggttct tgtctcccag actgaggtcg tcgagctcgc cctcggtctg    900
gagctctccg gtctgcccct cgtctgggcc taccgaaagc ccaagggtcc cgccaagtcc    960
gactccgtcg agctccccga cggtttcgtc gagcgaactc gagatcgagg tctggtctgg   1020
acctcttggg ctccccagct ccgaatcctc tcccacgagt ccgtctgcgg tttcctgacc   1080
cactgtggtt ccggctccat tgtcgagggc ctcatgttcg gccaccccct catcatgctg   1140
cccatcttcg gtgaccagcc cctcaacgcc cgactcctcg aggacaagca ggtcggtatc   1200
gagatccccc gaaacgaaga ggacggctgc ctcaccaagg agtctgttgc ccgatctctg   1260
cgatctgttg ttgtcgagaa agagggtgag atctacaagg ccaacgcccg agagctctcc   1320
aagatctaca cgacaccaa ggtcgagaag gagtacgttt cccagtttgt cgactacctc   1380
gagaagaacg cccgagctgt cgccattgac cacgagagtt aa                      1422

SEQ ID NO: 2            moltype = DNA  length = 803
FEATURE                 Location/Qualifiers
source                  1..803
                        mol_type = other DNA
                        organism = Yarrowia lipolytica
SEQUENCE: 2
taccaaccac agattacgac ccattcgcag tcacagttca ctagggtttg ggttgcatcc     60
gttgagagtg gtttgttttt aaccttctcc atgtgctcac tcaggttttg ggttcagatc    120
aaatcaaggc gtgaaccact gtttgaggac aaatgtgaca caaccaacca gtgtcagggg    180
caagtccgtg acaaagggga agatacaatg caattactga cagttacgga ctgcctcgat    240
gccctaacct tgccccaaaa taagacaact gtcctcgttt aaacaaacc ctattcagcg    300
tcacgtcata atagcgtttg gatagcacta gtctatgagg agcgttttat gttgcgcgtga   360
gggcgattgg tgctcatatg ggttcaattg aggtggtgga acgagcttag tcttcaattg    420
aggtgcgagc gacacaattg ggtgtcacgt ggcctaattg acctcggatc gtggagtccc    480
cagttataca gcaaccacga ggtcatgag taggagacgt caccagacaa taggttttt    540
ttggactgga gagggtaggg caaaagcgct caacgggctg tttggggagc tatggggag    600
gaattggcga tatttgtgag gttgacggct ccgatttgcg tgttttgtcg cttctgcatc    660
tccccatacc catatcttcc ctccccacct ctttccacga taattttacg gatcagcaat    720
aaggttcctt ctcctagttt ccacgtccat atatatctat gctgcgtcgt ccttttcgtg    780
acatcaccaa aacacataca aaa                                            803

SEQ ID NO: 3            moltype = DNA  length = 995
FEATURE                 Location/Qualifiers
source                  1..995
                        mol_type = other DNA
                        organism = Yarrowia lipolytica
SEQUENCE: 3
ctgtacctgc tgtggaccac gcacggcgga acgtaccgta caaatatttt cttgctcaca     60
tgactctctc tcggccgcgc acgcggtgg caaattgctc ttgcattggc tctgtctcta    120
gacgtccaaa ccgtccaaag tggcagggtg acgtgatgcg acgcacgaag gagatggccc    180
ggtggcgagg aaccggacac ggcgagccgg cgggaaaaaa ggcggaaaac gaaagcgaa    240
gggcacaatc tgacggtgcg gctgccacca acccaaggag gctattttgg gtcgctttcc    300
atttcacatt cgccctcaat ggccactttg cggtggtgaa catggtttct gaaacaaccc    360
cccagaatta gagtatattg atgtgtttaa gattgggttg ctatttggcc attgtggggg    420
aggtagcga cgtggaggac attccaggc gaattgagcc tagaaagtgg taccattcca    480
accgtctcag tcgtccgaat tgatcgctat aactatcacc tctctcacat gtctacttcc    540
ccaaccaaca tccccaacct cccccacact aaagttcacg ccaataatgt aggcactctt    600
tctgggtgtg ggacagcaga gcaatacgga ggggagatta caacgagc acaattggg    660
gagatggtag ccatctcact cgaccgtcg acttttggca acgctcaatt cccaccaaa    720
tttgggctgg agttgagggg accgtgttcc agcgctgtag gaccagcaac acacgtgtg    780
tcaacagcaa ccaacgcccc cgctaatgca cccagtactg cgcaggtgtg ggccaggtgc    840
gttccagatg cgagttggcg aaccctaagc cgacagtgta ctttttggga cgggcagtag    900
caatcgtggg cggagacccc ggtgtatata aggggtgga gaggacggat tattagcacc    960
aacacacaca cttatactac atgctagcca caaaa                              995

SEQ ID NO: 4            moltype = DNA  length = 1004
FEATURE                 Location/Qualifiers
source                  1..1004
                        mol_type = other DNA
                        organism = Yarrowia lipolytica
SEQUENCE: 4
gtcagaaggg gcagctctaa acgaagaact gcggtcaggt gacacaactt tttccatctc     60
agggtgtgtc gcgtgtgctt catccaaact ttagttgggt ttcgggttcg cgcgagatga    120
tcacgtgccc tgatttggtg tcgtccccg tcgcgctgcg cacgtgattt atttatttcc    180
ggtggctgct gtctacgcgg ggccttctct gcccttctgt ttcaaccttc gggcggttct    240
cgtaaccagc agtagcaatc catttcgaaa ctcaaagagc taaaaacgtt aaacctcagc    300
agtcgctcga cgaatgggct gcggttggga agcccacgag gcctatagcc agagcctcga    360
gttgacagga gcccagacgc cttttccaac ggcaactttt atataaatg gcaatgtatt    420
catgcaattg cggccgtgtc aggttggaga cactggacca cactctccat tgcttcctga    480
ggagatggat cattgctagt gcatctacgc gcagcaatcc cgcaagctcg acaaccgtag    540
atgggctttg tgggccaat caattacgca acccgcacgt taaattgtat gaggaaggaa    600
ggccacggta caaagtgggt ggtcttcacc cagtggttgt tggtggcgtc atgcagacca    660
tgcattgggg atagcacagg gttggggtgt cttgtgact caatggggta aaggagatgt    720
aaaagggcgc tgaaaagtgg tagaatcgaa atccctgacg tcaatttata aagtaaaatg    780
cgtttctgcc attttgctcc cctccttctt tcgcaatcgc ctcccaaaa gttgtcgtgg    840
cagtacacat gcttgcatac aatgaagcta atccggcttg ctcagtagtt gctatatcca    900
ggcatggtgt gaaacccctc aaagtatata taggagcggg gagccccagt ctgggtcttt    960
ttctctccat ctcaaaacta cttttctcaca tgctagccac aaaa                   1004
```

```
SEQ ID NO: 5            moltype = DNA  length = 1422
FEATURE                 Location/Qualifiers
source                  1..1422
                        mol_type = other DNA
                        organism = Yarrowia lipolytica
SEQUENCE: 5
atttcttgtg tgtgcggcaa acgtagcaat tgcaactgca taaacgatga ttgtaaaagt    60
atcacacttt gctcagacag gttagattca cctggtacga gggcagtgtc ttaaaggttc   120
catctacctc ggcccttgtt tcttgaagag tggtcaatat gtgttttata cagctgaaat   180
ttcccctgta tgttgagatc gtgtatattg gtcataatct gggctcttta gtcgatccca   240
gttttctcgg gcaagttttt ttctccacaa agtaccgctg gaaaactcta tgtgacttgt   300
tgacagatta cttgggttat ctgcgggata tgtcttggat aggcaaccgg gcatatatca   360
ccgggcggac tgttggttct gtacgtacat acagcacttt gagctcatgt ctcacacgta   420
accatggtgc gtgaggcttt ggcatcctt tctacttgta gtggctatag tacttgcagt    480
ccaagcaaac atgagtatgt gcttgtatgt actgaaaccc gtctacggta atatttaga    540
gtgtggaact atgggatgag tgctcattcg atactatgtt gtcacccgat ttgccgtttg   600
cgaggtaaga cacattcggt ggttcaggcg gctacttgta tgtagcatcc acgttcatgt   660
tttgtggatc agattaatgg tatgatatg cacggggcgt ttcccccggta acgtgtaggc   720
agtccagtgc aacccagaca gctgagctct ctatagccgt gcgtgtgcgg tcatatcacg   780
ctacacttag ctacagaata aagctcgta gcgccaacag cgttgacaaa tagctcaagg    840
gcgtgagca caggggttag gaggttttaa tgggcgaaga ggcgcgtaga tgtagtcttc    900
ctcggtccca tcgtaatca cgtgtgtgcc gatttgcaag acgaaaagcc acgagaataa    960
accgggagag gggatggaag tccccgaaca gcaaccagcc cttgccctcg tggacataac  1020
cttttcacttg ccagaactct aagcgtcacc acgtataca agcgcacgta gaagattgtg  1080
gaagtcgtgt tggagactgt tgatttgggc ggtggagggg gtatttggag agcaagtttg  1140
agatttgtgc cattgagggg gaggttattg tggccatgca gtcggatttg ccgtcacggg  1200
accgcaacat gcttttcatt gcagtccttc aactatccat ctcacctccc caatggcttt  1260
ttaactttcg aatgacgaaa gcacccccct ttgtacagat gactatttgg gaccaatcca  1320
atagcgcaat tgggtttgca tcatgtataa aaggagcaat cccccactag ttataaagtc  1380
acaagtatct cagtataccc gtctaaccac acatttatca cc                     1422

SEQ ID NO: 6            moltype = DNA  length = 865
FEATURE                 Location/Qualifiers
source                  1..865
                        mol_type = other DNA
                        organism = Yarrowia lipolytica
SEQUENCE: 6
atgctcactt tgttgtcct gatgatctcc cgttatttcg ccgctcctct ggaaaccatc    60
cgcccgcaaa tccctctgc ccatcttgac aatgcacaat gcatcattct cagcctgcat    120
gaatgcgaaa gatggcaata ttggtggagg aggcgacggc ggtaaacaat ggagatagag   180
accacaaaag agacctggag acccaaaatg gactcacgac aactccccca ctcccccact   240
ccctctctcc ccctgggcat cagttgccca tcggtatctc aactgtcgca ctagttagcg   300
caaccatcac atactttaga cgccaaacaa tgggacaact catcgcgccg aactatgggc   360
agattttaac tcgcacaaca ttaccccaac tctaaaaggt aacctcgacc ggaaaacggg   420
aagacaggat cagcaaccgt gatcgacaga atcttcaggg cactacagtt gatagacata   480
ggttatgttg gtaggtctag acgggcctcg gggaattgac cccaccagtt gacagtcacg   540
tgccctgat acagctagtt tagcacatct gcccactacg tctggacgca ccatggtggt   600
gccagtcgcg tgaactcaaa cacccactag cctcgggaag gattcagtta aatccgcacc   660
ttatttccaa cacaaagaag cggttggcgg acaaagaaca tgtcctttct ggggcactgt   720
acattccagg actctgttca aggtcaaata tacaaaacac agatagagaa acatagacag   780
ctgcggcctt ataaatacct gggcgcactt ctctcttttt ccctcctcat cacacattcg   840
ttcaccacta agtcactcgt tcaaa                                         865

SEQ ID NO: 7            moltype = DNA  length = 880
FEATURE                 Location/Qualifiers
source                  1..880
                        mol_type = other DNA
                        organism = Yarrowia lipolytica
SEQUENCE: 7
aaacaaaaga gctgaaatca tatccttcag tagtagtata gtcctgttat cacagcatca    60
attacccccg tccaagtaag ttgattggga tttttgttta cagatacagt aatatacttg   120
actatttctt tacaggtgac tcagaaagtg catgttggaa atgagccaca gaccaagaca   180
agatatgaca aaattgcact attcgatgca gaattcgacg tggtttccat tggtgttatg   240
acattcatct gcattcatac aaaaaagtct tggtagtggt acttttgcgt tattacctcc   300
gatatctacg caccccccaa ccccccctgct acagtaaaga gtgtgagtct actgtacatg   360
cttactaaac cacctactgt acagcgaaac ccctcagcaa atcacacaa tcagctcatt    420
acaacacacc caatgacctc accacaaatt ctatacgcct tttgacgcca ttattcagt    480
agcttgcaac gccgttgtct taggttccat ttttagtgct ctattccctc acttaaccgt   540
tataggcaga tcaggccatg gcactaagtg tagagctaga ggttgatatc gccacgagtg   600
ctccatcagg gctaggtgg ggttagaaat acagtccgtg cgcactcaaa aggcgtccgg    660
gttagggcat ccgataatat cgcctggact cggcgccata ttctcgactt ctgggcgcgt   720
tgtattcatc tcctccgctt cccaacactt ccacccgttt ctccatccca accaatagaa   780
tagggtaacc ttattcggga cactttcgtc atacatagtc agatatacaa gcaatgtcac   840
tctccttcgt actcgtacat acaacacaac tacattcaaa                         880

SEQ ID NO: 8            moltype = DNA  length = 1000
FEATURE                 Location/Qualifiers
source                  1..1000
```

```
                   mol_type = other DNA
                   organism = Yarrowia lipolytica
SEQUENCE: 8
caattcatgt atcgtgtcaa ttcatgtatc gtgtcaattc atgtatcgtg tcaatactta    60
tatctcaagt ggttgcatcg caaacagcca tcgcatactc cactctactc tcactgagtt   120
cactcttacc cggctccacc ttctagaagc caccaccgat ccaccgacga tgatcagtcc   180
accacttgct ctgaatgtgc gttggagctg caccatgatt gatgacgtca ccgccattca   240
gatagggcaa aagacgagcg ccaatcgcaa caatgggcga gtgtcgacga ctcccccgct   300
ctctgcggtt tcagcgactc caaccgtcgc caaaagaccg tcattttcgt ctaaagcgca   360
gcccagccca tctcttctaa aagattccag aaagataggg ttcaccaact acgcaccaat   420
atgtacagta tcgtagctac tccggcttgg ctgatctgag agatagagat ggctccgaaa   480
cgcggaaaac ggcggggtcg gaccgatcac gtgacacgta tcatccgtc gcgccccgag    540
cgccatttca acaccaaata ctcccggtca cgtgccaccc cgcccgctct acccacgaga   600
tgtttctaca ctatacactg ccacgccgtc ataccgtcag ctaggttaac attcgattaa   660
ttagtggagt caccagtgta caggactatg gcgaaaccg ggttacacaa accggcccgg    720
aatagcagca ttataccgct ggacgagatc ccgtcaata aattgcgtcg ttactcggga    780
caaccattgc tcctccggct acacctgctc aaaggacttg ttccacactc ttccccagct   840
ctcccacgca aacaaagaga gcaaccttaa gtggacagct catgagcact ccctcgtttt   900
gctgccacg ctcgattata taaagaccag cggatcccct tctatttgga cttgcatcaa     960
ccaaccacaa cccacaccaa gcacacaaag cacaagaaca                         1000

SEQ ID NO: 9           moltype = DNA   length = 127
FEATURE                Location/Qualifiers
source                 1..127
                       mol_type = other DNA
                       organism = Yarrowia lipolytica
SEQUENCE: 9
aattaacaga tagtttgccg gtgataattc tcttaacctc ccacactcct ttgacataac    60
gatttatgta acgaaactga aatttgacca gatattgttg taaatagaaa atctggcttg   120
taggtgg                                                             127

SEQ ID NO: 10          moltype = DNA   length = 200
FEATURE                Location/Qualifiers
source                 1..200
                       mol_type = other DNA
                       organism = Yarrowia lipolytica
SEQUENCE: 10
gttttttgat caatgatcca atggctttca catacccccc cacgcctata attaaaacac    60
agagaaatat aatctaactt aataaatatt acggagaatc tttcgagtgt tcagcagaaa   120
tatagccatt gtaacaaaag ccggctatcg accgcttat cgaagaatat ttcccgcccc    180
ccagtggcca aacgatatcg                                               200

SEQ ID NO: 11          moltype = DNA   length = 200
FEATURE                Location/Qualifiers
source                 1..200
                       mol_type = other DNA
                       organism = Yarrowia lipolytica
SEQUENCE: 11
ctatccgaag atcaagagcg aagcaagttg taagtccagg acatgttcc cgcccacgcg     60
agtgattat aacacctctc tttttgaca cccgctcgcc ttgaaattca tgtcacataa    120
attatagtca acgacgtttg aataacttgt cttgtagttc gatgatgatc atatgattac   180
attaatagta attactgtat                                               200

SEQ ID NO: 12          moltype = DNA   length = 200
FEATURE                Location/Qualifiers
source                 1..200
                       mol_type = other DNA
                       organism = Yarrowia lipolytica
SEQUENCE: 12
acttcgagct aatccagtag cttacgttac ccaggggcag gtcaactggc tagccacgag    60
tctgtcccag gtcgcaattt agtgtaataa acaatatata tattgagtct aaagggaatt   120
gtagctattg tgattgtgtg attttcgtct tgctggttct tattgtgtcc cattcgtttc   180
atcctgatga ggaccctgg                                                200

SEQ ID NO: 13          moltype = DNA   length = 200
FEATURE                Location/Qualifiers
source                 1..200
                       mol_type = other DNA
                       organism = Yarrowia lipolytica
SEQUENCE: 13
gctatttaca gcatgtgtaa tgaggaatat aacgttgatt gaattgtttg tgaaaaatgt    60
agaaaatttc agtgaagttg tgttttctat atagtaagca cttttggtac aagtatctgc   120
acatccctgc atgttacaag cctgatcatg cagggcaata ttctgactat aaatataacct  180
cgatattta gcaagctata                                                200

SEQ ID NO: 14          moltype = DNA   length = 300
FEATURE                Location/Qualifiers
source                 1..300
                       mol_type = other DNA
```

```
                        organism = Yarrowia lipolytica
SEQUENCE: 14
atgtggtgat tgctgttgtg caagcctttg ctcgttttct gctgtatgta atttaaagaa    60
cgattgtatg aatcgaagtc aaggtgagtg tagtttgaga agtgtaaccc cagtgtcata   120
gctgtgtact ccattcattg aagggtgtag tcgtgtttta ttgcatgagc gcctattact   180
cgtataagta actgttttgt aacacttcat gaacggagat ggtatgaaca gaagtaataa   240
tatcctggaa gtcagctgtg cccagaggtg tgtgtgggtg tggcatactt tgggacaaca   300

SEQ ID NO: 15           moltype = DNA   length = 1503
FEATURE                 Location/Qualifiers
misc_feature            1..1503
                        note = tHMG CpO for Yarrowia lipolitica
source                  1..1503
                        mol_type = other DNA
                        organism = synthetic construct
SEQUENCE: 15
atgacccagt ctgtgaaggt ggttgagaag cacgttccta tcgtcattga gaagcccagc    60
gagaaggagg aggacacctc ttctgaagac tccattgagc tgactgtcgg aaagcagccc   120
aagcccgtga ccgagacccg ttctctggac gacttggagg ctatcatgaa ggcaggtaag   180
accaagctcc tggaggacca cgaggttgtc aagctctctc tcgaaggcaa gctccctttg   240
tatgctcttg agaagcagct tggtgacaac acccgagctg ttggcatccg acgatctatc   300
atctcccagc agtctaatac caagactctt gagacctcaa agctccctta cctgcactac   360
gactacgacc gtgttttgg agcctgttgc gagaacgtta ttggttacat gcctctcccc   420
gttggtgttg ctggcccat gaacattgat ggcaagaact accacattcc tatgccacc    480
actgagggt gtcttgttgc ctcaaccatg cgaggttgca aggccatcaa cgccggtggc   540
ggtgttacca ctgtgcttac tcaggacggt atgacacgag gtccttgtgt ttccttcccc   600
tctctcaagc gggctggagc cgctaagatc tggcttgatt ccgaggaggg tctcaagtcc   660
atgcgaaagg ccttcaactc cacctctcga tttgctcgtc tccagtctct tcactctacc   720
cttgctggta acctgctgtt tattcgattc cgaaccacca ctggtgatgc catgggcatg   780
aacatgatct ccaagggcgt cgaacactct ctggccgtca tggtcaagga gtacggcttc   840
cctgatatgg acattgtgtc tgtctcgggt aactactgca ctgacaagaa gcccgcagcg   900
atcaactgga tcgaaggccg aggcaagagt gttgttgccg aagccaccat ccctgctcac   960
attgtcaagt ctgttctcaa aagtgaggtt gacgctcttg ttgagctcaa catcagcaag  1020
aatctgatcg gtagtgccat ggctggctct gtgggaggtt tcaatgcaca cgccgcaaac  1080
ctggtgaccg ccatctacct tgccactggc caggatcctg ctcagaatgt cgagtcttcc  1140
aactgcatca cgctgatgag caacgtcgac ggtaacctgc tcatctccgt ttccatgcct  1200
tctatcgagg tcggtaccat tggtggaggt actattttgg agccccaggg tgctatgctg  1260
gagatgcttg gcgtgcgagg tcctcacatc gagaccccg gtgccaacgc caacagctt   1320
gctcgcatca ttgcttctgg agttcttgca gcggagcttt cgctgtgttc tgctcttgct  1380
gccggccatc ttgtgcaaag tcatatgacc cacaaccgtt cccaggctcc tactccggcc  1440
aagcagtctc aggccgatct gcagcgtctc caaaacggtt cgaatatctg cattcggtca  1500
tag                                                                1503

SEQ ID NO: 16           moltype = DNA   length = 984
FEATURE                 Location/Qualifiers
misc_feature            1..984
                        note = GGS CpO for Yarrowia lipolitica
source                  1..984
                        mol_type = other DNA
                        organism = synthetic construct
SEQUENCE: 16
atggattata acagcgcgga tttcaaggag atctggggca aggccgccga caccgcgctg    60
ctgggaccgt acaactacct cgccaacaac cggggccaca acatcagaga acacttgatc   120
gcagcgttcg gagcggttat caaggtggac aagagcgatc tcgaaaccat ttcgcacatc   180
accaagattt tgcataactc gtcgctgctt gttgatgacg tggaagacaa ctcgatgctc   240
cgacgaggcc tgccggcagc ccattgtctg tttggagtcc ccaaaaccat caactccgca   300
aactacatgt actttgtggc tctgcaggag gtgctcaagc tcaagtctta tgatgccgtc   360
tccattttca ccgaggaaat gatcaacttg catagaggtc agggtatgga tctctactgg   420
agagaaacac tcacttgccc ctcggaagac gagtatctgg agatggtggt gcacaagacc   480
ggaggactgt ttcggctggc tctgagactt atgctgtcga tggcatcgaa acaggaggac   540
catgaaaaga tcaactttga tctcacacac cttaccgaca cactgggagt catttaccag   600
attctggatg attacctcaa cctgcagtcc acggaattga ccgagaacaa gggattctgc   660
gaagatatca gcgaaggaaa gttttcgttt ccgctgattc acagcatccg gaccaacccg   720
gataaccacg agattctcaa cattctcaaa cagcgaacaa gcgacgcttc actcaaaaag   780
tacgccgtgg actacatgag aacagaaacc aagagtttcg actactgcct caagagaatc   840
caggccatgt cactcaaggc aagttcgtac attgatgatc tcgcagcagc cggccacgat   900
gtctccaagt tgcgagccat tttgcattat tttgtgtcca cctctgactg tgaggagaga   960
aagtactttg aggatgcgca gtga                                          984

SEQ ID NO: 17           moltype = DNA   length = 1446
FEATURE                 Location/Qualifiers
misc_feature            1..1446
                        note = UGT1 CpO for Yarrowia lipolitica
source                  1..1446
                        mol_type = other DNA
                        organism = synthetic construct
SEQUENCE: 17
atggacgcca tggccaccac cgagaagaag ccccacgtca tcttcatccc cttcccccgcc   60
cagtcccaca tcaaggccat gctcaagctc gcccagctcc tccaccacaa gggcctccag  120
```

```
atcacctttg tcaacaccga cttcatccac aaccagttcc tcgagtcctc cggcccccac  180
tgtctggacg gtgctccgg ttttccgatt gagactatcc ccgatggtgt ctcccactcc    240
cccgaggcct ccatccccat ccgagagtct ctgctccgat ccattgagac taacttcctc  300
gaccgattca ttgatctcgt caccaagctc cccgatcctc ccacctgtat catctccgac  360
ggtttcctgt ccgttttcac cattgatgct gccaagaagc tcggtatccc cgtcatgatg  420
tactggactc tggctgcctg tggtttcatg ggtttctacc acatccactc tctgatcgag  480
aagggctttg ctcctctcaa ggacgcctcc tacctcacca acggttacct cgacaccgtc  540
attgactggg tccccggtat ggagggtatc cgactcaagg acttccccct cgactggtcc  600
accgacctca acgacaaggt tctcatgttc accaccgagg ctccccagcg atcccacacg  660
gtttcccacc acatcttcca caccttcgac gagctcgagc cctccatcat caagactctg  720
tctctgcgat acaaccacat ctacaccatt ggcccctcc agctcctcct cgaccagatc  780
cccgaggaga agaagcagac cggtatcacc tctctgcacg gctactctct cgtcaaggaa  840
gagcccgagt gcttccagtg gctccagtcc aaggagccca actccgttgt ctacgtcaac  900
tttggctctc ccaccgtcat gtctctcgag gacatgaccg agtttggctg gggtctggtc  960
aactccaacc actacttcct gtggatcatc cgatccaacc tcgtcattgg cgagaacgcc  1020
gttctgcctc ccgagctcga ggagcacatc aagaagcgag gcttcattgc ctcttggtgc  1080
tcccaggaga aggttctcaa gcacccctcc gtcggtggtt tcctgaccca ctgcggctgg  1140
ggctccacca ttgagtctct gtccgctggt gtccccatga ttgctggcc ctactcctgag  1200
gaccagctca ccaactgccg atacatctgc aaggagtggg aggttggtct ggagatgggg  1260
accaaggtca agcgagatga ggtcaagcga ctcgtccagg agctcatggg cgagggtggt  1320
cacaagatgc gaaacaaggc caaggactgg aaggagaagg cccgaattgc cattgccccc  1380
aacggctctt cttctctcaa cattgacaag atggtcaagg agatcactgt tctcgctcga  1440
aactaa                                                             1446

SEQ ID NO: 18             moltype = DNA   length = 1383
FEATURE                   Location/Qualifiers
misc_feature              1..1383
                          note = UGT3 CpO for Yarrowia lipolitica
source                    1..1383
                          mol_type = other DNA
                          organism = synthetic construct
SEQUENCE: 18
atggccgagc agcagaagat caagaagtct ccccacgttc tgctcatccc cttccctctg  60
cagggccaca tcaacccctt catccagttc ggcaagcgac tcatctccaa gggtgtcaag  120
accactctgg tcaccaccat ccacaccctc aactccactc tcaaccactc caacaccacc  180
accacctcca tcgagatcca ggccatctcc gacggctgtg acgagggtgg tttcatgtct  240
gctggtgagt cttacctcga cttttcaag caggtcggtt ccaagtctct ggctgacctc  300
atcaagaagc tccagtccga gggtaccacc attgacgcca tcatctacga ctccatgacc  360
gagtgggttc tcgatgtcgc catcgagttt ggtattgacg gtggctcctt cttcacccag  420
gcctgtgtcg tcaactctct ctactaccac gtccacaagg gtctgatctc tctgcccctc  480
ggcgagactg tctccgtccc cggtttcccc gttctgcagc gatgggagac tcctctcatt  540
ctccagaacc acgagcagat ccagtccccc tggtcccaga tgctcttcgg ccagttcgcc  600
aacattgagc aggcccgatg ggttttcacc aactccttct acaagctcga ggaagaggtc  660
attgagtgga cccgaaagat ctggaacctc aaggtcattg gccccaccct cccctccatg  720
tacctcgaca agcgactcga tgacgacaag gacaacggtt caacctcta caaggccaac  780
caccacgagt gcatgaactg gctcgacgac aagcccaagg agtccgttgt ctacgttgcc  840
tttggctctc tggtcaagca cggccccgag caggttgagg agatcaccg agctctgatt  900
gactccgatg tcaacttcct gtgggtcatc aagcacaagg aagagggtaa gctccccgag  960
aacctgtccg aggtcatcaa gaccggcaag ggcctcattg ttgcctggtg caagcagctc  1020
gacgttctcg cccacgagtc cgtcggctgc tttgtcaccc actgcggctt caactccacc  1080
ctcgaggcta tctctctcgg tgtccccgtt gttgccatgc cccagttcgc cgaccagacc  1140
accaacgcca agctcctcga tgagattctc gtgtgtcggtg tccgagtcaa ggctgacgag  1200
aacggtattg tccgacgagg taacctggct cttgtatca gatgatcat ggaggaagag  1260
cgaggtgtca tcatccgaaa gaacgccgtc aagtggaagg atctggccaa ggttgctgtc  1320
cacgagggtg gctcttccga caacgacatt gtcgagtttg tctccgagct catcaaggcc  1380
taa                                                                1383

SEQ ID NO: 19             moltype = DNA   length = 1377
FEATURE                   Location/Qualifiers
misc_feature              1..1377
                          note = UGT4 CpO for Yarrowia lipolitica
source                    1..1377
                          mol_type = other DNA
                          organism = synthetic construct
SEQUENCE: 19
atggagaaca agaccgagac taccgtccga cgacgacgac gaatcattct cttccccgtc  60
cccttccagg gccacatcaa ccccattctg cagctcgcca acgttctgta ctccaagggc  120
ttctccatca ccatcttcca caccaacttc aacaagccca agacctccaa ctaccccac   180
ttcactttcc gattcatcct cgacaacgac ccccaggacg agcgaatctc caacctgccc  240
acccacggtc ctctggctgg tatgcgaatc cccatcatca cgagcacgg tgctgacgag  300
ctccgacgag agctcgagct gctcatgctc gcctccgaag aggacgagga agtcctgt    360
ctgatcaccg atgctctgtg gtactttgcc cagtccgtcg ccgactctct caacctgcga  420
cgactcgttc tcatgacctc ctctctgttc aacttccacg cccacgtttc tctgcccag   480
tttgacgagc tcggttacct cgaccccgat gacaagaccc gactcgagga gcaggcttcc  540
ggtttcccca tgctcaaggt caaggacatc aagtccgcct actccaactg cgcagattct  600
aaggagattc tcggcaagat gatcaagcag accaaggcct cctccggtgt catctggaac  660
tccttcaagg agctcgagga gtccgagctc gagactgtca tccgagagat ccccgctccc  720
tctttcctca tccccctgcc caagcacctc accgcttcct cctcttctct gctcgaccac  780
gaccgaaccg tctttcagtg gctcgaccag cagcccctc ctccgtcct ctacgttcc    840
```

```
ttcggctcca cctccgaggt cgacgagaag gacttcctcg agattgctcg aggcctcgtt    900
gactccaagc agtccttcct gtgggttgtc cgaccggct ttgtcaaggg ctccacctgg      960
gttgagcccc tgcccgatgg tttcctcggt gagcgaggcc gaattgtcaa gtgggtcccc   1020
cagcaggaag ttctggccca cggtgccatt ggtgccttct ggaccactc cggctggaac   1080
tccactctcg agtccgtctg cgaggtgtc cccatgatct tctccgactt tggcctcgac    1140
cagcccctca acgccgata catgtccgat gttctcaagg tcggtgtcta cctcgagaac   1200
ggctgggagc gaggtgagat tgccaacgcc atccgacgag tcatggtcga cgaggaaggt   1260
gagtacatcc gacagaacgc ccgagtcctc aagcagaagg ccgatgtctc tctcatgaag   1320
ggtggttctt cttacgagtc tctcgagtct ctcgtttcct acatctcttc tttgtaa       1377
```

| | | |
|---|---|---|
| SEQ ID NO: 20 | moltype = DNA length = 2232 | |
| FEATURE | Location/Qualifiers | |
| misc_feature | 1..2232 | |
| | note = tCPS_SR CpO for Yarrowia lipolitica | |
| source | 1..2232 | |
| | mol_type = other DNA | |
| | organism = synthetic construct | |

SEQUENCE: 20
```
atgtgcaagg ctgttccaa ggagtactcc gatctgctcc agaaggacga ggcctctttc      60
accaagtggg acgacgacaa ggtcaaggac cacctcgaca ccaacaagaa cctctacccc    120
aacgacgaga tcaaggagtt tgtcgagtcc gtcaaggcca tgttcggctc catgaacgac    180
ggcgagatta atgtctctgc ttacgacacc gcctgggtg tcttggtcca ggatgtcgac    240
ggttccggct ctcctcagtt ccctcctct ctcgagtgga tcgccaacaa ccagctgtcc    300
gacggttctt ggggtgacca cctgctcttc tctgctcacg accgaatcat caacaccctg    360
gcctgtgtca ttgctctgac ctcttggaac gtccacccct ccaagtgcga gaagggtctg    420
aacttcctcc gagagaacat ctgcaagctc gaggacgaga acgccgacat catgcccatt    480
ggcttcgagg tcaccttccc ctctctgatt gacattgcca agaagctcaa cattgaggtc    540
cccgaggaca cccccgctct caaggagatc tacgctcgac gagacatcaa gctcaccaag    600
atccccatga aggttctcca aaggtcccc accactctcc tccactctct cgagggtatg    660
cccgatctcg agtgggagaa gctgctcaag ctgcagtgca aggacggctc tttcctcttc    720
tcccctctct ccactgcctt cgccctcatg cagaccaagg acgagaagtg tctccagtac    780
ctcaccaaca ttgtcaccaa gttcaacggt ggtgtcccca acgtctaccc cgttgacctc    840
tttgagcaca tctgggttgt tgaccgactc agcgactcg gtatcgcccg atacttcaag    900
tccgagatca aggactgtgt cgagtacatc aacaagtact ggactcaaga ccggtatctgc    960
tgggcccgaa acacccacgt ccaggacatt gacgacaccg ccatgggctt ccgagttctg   1020
cgagcccacg gctacgatgt cacccccgat gtctttcgac agtttgagaa ggacggcaag   1080
tttgtctgtt tcgccggtca gtccaccag gccgtcaccg gtatgttcaa cgtctaccga   1140
gcttctcaga tgctcttccc cggtgagcga atcctcgagg acgccaagaa gttctcctac   1200
aactacctca aggagaagca gtccaccaac agctgctcga acaagtggat cattgccaag   1260
gatctgcccg tgaggttgg ctacgccctc gacatcccct ggtacgcctc tctgccccga   1320
ctggagactc gatactacct cgagcagtac ggtggtgagg acgatgtctg gatcggtaag   1380
accctgtacc gaatgggcta cgtttccaac aacacctacc tcgagatggc caagctcgac   1440
tacaacaact acgttgccgt cctccagctc gagtggtaca ccatccagca gtggtacgtc   1500
gacattggta tcgagaagtt cgagtccgac aacatcaagt ccgtccttgt ctcctactac   1560
ctcgctgctg cctccatctt cgagcccgag cgatccaagg agcgaattgc ctgggccaag   1620
accaccatcc tcgtcgacaa gatcacctcc atcttcgact cctcccagtc ctccaaggaa   1680
gatatcaccg ccttcattga caagttccga aacaagtcct cctccaagaa gcactccatc   1740
aacggcgagc cctggcacga ggtcatggtt gctctcaaga aaactctcca cggctttgcc   1800
ctcgacgctc tgatgaccca ctctcaggac atccaccccc agctccacca ggcctgggag   1860
atgtggctca ccaagctcca ggacggtgtt gatgtcactg ctgagctcat ggtccagatg   1920
atcaaacatga ccgccggccg atgggtttcc aaggagctcc tcacccaccc ccagtaccag   1980
cgactctcca ctgtcaccaa ctctgtctgc cacgacatca ccaagctcca caacttcaag   2040
gagaactcca ccaccgtcga ctccaaggtc caggagctgg tccagctcgt ttcctccgac   2100
accccccgatg atctccgacca ggacatgaag cagaccttcc tgactgtcat gaaaactttc   2160
tactacaagg cctggtgcga ccccaacacc atcaacgacc acatctccaa ggtctttgag   2220
attgtgattt aa                                                        2232
```

| | | |
|---|---|---|
| SEQ ID NO: 21 | moltype = DNA length = 2274 | |
| FEATURE | Location/Qualifiers | |
| misc_feature | 1..2274 | |
| | note = tKS-SR CpO for Yarrowia lipolitica | |
| source | 1..2274 | |
| | mol_type = other DNA | |
| | organism = synthetic construct | |

SEQUENCE: 21
```
atgacctccc acggcggcca gaccaacccc accaacctca tcattgacac caccaaggag      60
cgaatccaga agcagttcaa gaacgtcgag atctccgttt cctcctacga caccgcctgg    120
gtcgccatgg tccctctcc caactccccc aagtctccct gcttccccga gtgtctcaac    180
tggctcatca acaaccagct caacgacggc tcttgggcga tggtcaaacca caccacaac    240
cacaaccacc cctcctcaa ggactctctc tcttccactc tcgcctgcat tgttgctctc    300
aagcgatgga cgttggcga ggaccagatc aacaagggtc tgtctttcat tgagtccaac    360
ctcgcctccg ccaccgagaa gtcccagccc tccccattg cctttgatat catcttcccc    420
ggtctgctcg agtacgccaa gaacctcgat atcaacctgc ctccaagca gaccgacttc    480
tctctcatgc tgcacaagcg agagctcgag cagaagcgat gccactccga agagatggac    540
ggctacctgg cctacattc cgagggtctg ggtaacctct acgactggaa catggtcaag    600
aagtaccaga tgaagaacgg ttccgttttc aactccccct ctgccaccgc tgctgccttc    660
atcaaccacc agaaccccgg ctgtctcaac tacctcaact ctctgctcga caagtttggt    720
aacgccgtcc ccactgtcta cccccacgat ctcttcatcc gactctccat ggtcgacacc    780
attgagcgac tcggtattc ccaccacttc gagtcgaga tcaagaacgt tctcgatgag    840
```

```
acttaccgat gctgggttga gcgagatgag cagatcttca tggacgttgt cacctgtgct    900
ctggccttcc gactcctccg aatcaacggt tacgaggttt cccccgaccc cctcgccgag    960
atcaccaacg agctggctct caaggacgag tacgccgccc tcgagactta ccacgcttct   1020
cacattctgt accaagagga tctgtcctcc ggcaagcaga ttctcaagtc cgccgacttc   1080
ctcaaggaga tcatctccac tgactccaac cgactcctca agctcatcca caaggaagtc   1140
gagaacgctc tcaagttccc catcaacacc ggtctggagc gaatcaacac ccgacgaaac   1200
atccagctct acaacgtcga caacacccga attctcaaga ccacctacca ctcttccaac   1260
atctccaaca ccgactacct gcgactcgcc gtcgaggact tctacacctg ccagtccatc   1320
taccgagagg agctcaaggg tctggagcga tgggttgtcg agaacaagct cgaccagctc   1380
aagtttgccc gacaaaagac tgcctactgc tacttctccg ttgctgccac cctctcttct   1440
cccgagctct ccgacgcccg aatctcttgg gccaagaacg gtatcctgac cactgttgtc   1500
gacgacttct ttgacattgg tggcaccatt gacgagctga ccaacctcat ccagtgcgtc   1560
gagaagtgga acgtcgacgt tgacaaggac tgttgttccg agcacgtccg aatcctcttc   1620
ctggctctca aggacgccat ctgctggatc ggtgacgaag ccttcaagtg gcaggctcga   1680
gatgtcactt cccacgtcat ccagacctgg ctcgagctca tgaactccat gctgcgagag   1740
gccatctgga cccgagatgc ctacgtcccc accctcaacg agtacatgga gaacgcctac   1800
gtcagctttg ctctcggtcc cattgtcaag cccgccatct actttgtcgg tcccaagctg   1860
tccgaggaga ttgtcgagtc ctccgagtac cacaacctct tcaagctcat gtccacccag   1920
ggccgactcc tcaacgatat ccactccttc aagcgagagt tcaaggaagg taagctcaac   1980
gccgttgctc tgcacctgtc caacggtgag tccggcaagt cgaggaaga ggtcgtcgag   2040
gagatgatga tgatgatcaa gaacaagcga aggagctca tgaagctcat cttcgaggag   2100
aacggctcca ttgtccccg agcctgcaag gacgccttct ggaacatggc ccacgtcctc   2160
aacttcttct acgccaacga cgacggtttc accggcaaca ccattctcga caccgtcaag   2220
gacatcatct acaaccctct ggttctggtc aacgagaacg aggagcagag gtaa          2274

SEQ ID NO: 22            moltype = DNA   length = 1578
FEATURE                  Location/Qualifiers
misc_feature             1..1578
                         note = KAH_4 CpO for Yarrowia lipolitica
source                   1..1578
                         mol_type = other DNA
                         organism = synthetic construct
SEQUENCE: 22
atggagtctc tggttgtcca caccgtcaac gccatctggt gcattgtcat tgtcggtatc     60
ttctccgtcg gctaccacgt ctacggccga gctgttgtcg agcagtggcg aatgcgacga    120
tctctcaagc tccagggtgt caagggtcct cctccctcca tcttcaacgg taacgtttcc    180
gagatgcagc gaatccagtc cgaggccaag cactgctccg tgacaacat catctcccac    240
gactactctt cttctctgtt cccccacttt gaccactggc gaaagcagta cggccgaatc    300
tacacctact ccactggcct caagcagcac ctctacatca accaccccga gatggtcaag    360
gagctctccc agaccaacac cctcaacctc ggccgaatca cccacatcac caagcgactc    420
aacccccattg tcggtaacgg tatcatcacc tccaacggcc ccactgggcc caccagcga    480
cgaatcattg cctacgagtt cacccacgac aagatcaagg gtatggtcgg tctgatggtc    540
gagtccgcca tgcccatgct caacaagtgg gaggagatgg tcaagcgagg tggtgagatg    600
ggctgtgaca tccgagtcga cgaggacctc aaggatgtct ccgctgacgt cattgccaag    660
gcctgtttcg gctcttcctt ctccaagggc aaggccatct tctccatgat ccgagatctg    720
ctcaccgcca tcaccaagcg atccgtcctc ttccgattca cggtttcac cgacatggtt    780
ttcggctcca agaagcacgg tgacgttgac attgacgctc tcgagatgga gctcgagtcc    840
tccatctggg agactgtcaa ggagcgagag attgagtgca aggacaccca caagaaggac    900
ctcatgcagc tcattctcga gggtgccatc cgatcttgtg acgtaacct gtgggacaag    960
tctgcttacc gacgattcgt tgtcgacaac tgcaagtcca tctactttgc cggccacgac   1020
tccaccgccg ttccgtttc ttggtgcctc atgctgctcg ctctcaaccc tctcttggcag   1080
gtcaagatcc gagatgagat tctgtcctcc tgcaagaacg gtatcccga cgccgagtcc   1140
atccccaacc tcaagaccgt caccatggtc atccaggaga ctatgcgact ctaccctccc   1200
gctcccattg tcggccgaga ggcctccaag gacattcgac tcggtgatct ggttgtcccc   1260
aagggtgtct gtatctggac ccctcatccc gctctgcaac gagatcccga gatctgggt   1320
cccgacgcca acgacttcaa gcccgagcga ttctccgagg gtatctccaa ggcctgcaag   1380
taccccagt cctacatccc cttttggcct ggccccgaa cctgtgtcgg caagaacttt   1440
ggtatgatga aggtcaaggt cctcgttcct ctgattgct ccaagttctc cttcactctg   1500
tctcccacct accagcactc tccctccac aagctgctcg tcgagcccca gcacggtgtt   1560
gtcatccgag ttgtataa                                                 1578

SEQ ID NO: 23            moltype = DNA   length = 1578
FEATURE                  Location/Qualifiers
misc_feature             1..1578
                         note = KO_Gib CpO for Yarrowia lipolitica
source                   1..1578
                         mol_type = other DNA
                         organism = synthetic construct
SEQUENCE: 23
atgtccaagt ccaactccat gaactccacc tcccacgaga ctctcttcca gcagctcgtt     60
ctcggcctcg accgaatgcc cctcatggac gtccactggc tcatctacgt tgcctttggt    120
gcctggctct gctcctacgt catccacgtt ctgtcctctt cctccactgt caaggtcccc    180
gtcgtcggtt accgatccgt tttcgagccc acctggctcc tccgactgcg attcgtctgg    240
gagggtggtt ccatcattgg ccagggctac aacaagttca aggacccaat cttccaggtc    300
cgaaagctcg gtaccgacat tgtcatcatc cctccccaact acattgacga ggtccgaaag    360
ctctcccagg acaagacccg atccgtcgag cccttcatca cgactttgc cggcagtac    420
acccgaggta tggtctttct gcagtccgat ctccagaacc gagtcatcca gcagcgactc    480
acccccaagc ttgtctctct caccaaggtc atgaaggaag agctcgacta cgctctgacc    540
aaggagatgc ccgacatgaa gaacgacgag tgggttgagg tcgacatctc ttccatcatg    600
```

```
gtccgactca tctctcgaat ctccgcccga gttttcctcg gccccgagca ctgccgaaac   660
caggagtggc tcaccaccac cgccgagtac tccgagtctc tcttcatcac cggcttcatc   720
ctccgagttg tccccacat  tctccgaccc ttcattgctc ctctgctgcc ctcttaccga   780
accctgctgc gaaacgtttc ttccggccga cgagtcattg gtgatatcat ccgatcccag   840
cagggtgacg gtaacgagga catcctctct tggatgcgaa atgctgccac tggtgaggag   900
aagcagatcg acaacattgc ccagcgaatg ctcattctgt ctctcgcctc catccacacc   960
accgccatga ccatgaccca cgccatgtac gatctgtgtg cctgcccga  gtacattgag  1020
cccctccgag atgaggtcaa gtccgtcgtt ggtgcttctg gctgggacaa gaccgctctc  1080
aaccgattcc acaagctcga ctctttcctc aaggagtccc agcgattcaa cccgttttc   1140
ctgctcacct tcaaccgaat ctaccaccag tccatgaccc tctccgatgg taccaacatc  1200
ccctccggta cccgaattgc tgtcccctct cacgccatgc tccaggactc cgcccacgtc  1260
cccggtccca ctcctcccac tgagttcgac ggtttccgat actccaagat ccgatccgac  1320
tccaactacg cccagaagta cctcttctcc atgaccgact cttcgaacat ggcctttggc  1380
tacggtaagt acgcctgccc cggccgattc tacgcctcca acgagatgaa gctgactctg  1440
gccattctgc tcctccagtt tgagttcaag ctccccgacg gtaagggccg accccgaaac  1500
atcaccatcg actccgacat gatccccgac ccccgagctc gactctgtgt ccgaaagcga  1560
tctctgcgtg acgagtaa                                                1578

SEQ ID NO: 24           moltype = DNA   length = 2133
FEATURE                 Location/Qualifiers
misc_feature            1..2133
                        note = CPR_3 CpO for Yarrowia lipolitica
source                  1..2133
                        mol_type = other DNA
                        organism = synthetic construct
SEQUENCE: 24
atgtcctcct cttcttcttc ttccacctcc atgattgatc tcatggctgc catcatcaag    60
ggtgagcccg tcattgtctc cgaccccgcc aacgcctccg cctacgagtc cgttgctgcc   120
gagctgtcct ccatgctcat cgagaaccga cagtttgcca tgatcgtcac cacctccatt   180
gctgttctca ttggctgcat tgtcatgctc tctctggcga gatctggctc cggtaactcc   240
aagcgagtcg agccctcaa  gcccctggtc atcaagcccc gagaagagga gatcgacgac   300
ggccgaaaga aggtcaccat cttcttggc  acccagaccg gtactgctga gggcttcgcc   360
aaggctctcg gtgaggaagc caaggctcga tacgaaaaga cccgattcaa gattgtcgac   420
ctcgatgatt acgctgccga tgacgacgag tacgaggaga agtcaagaa  agaggacgtt   480
gccttcttct tcctcgccac ctacggtgac ggtgagccca ccgacaagcc tgcccgattc   540
tacaagtggt tcaccgaggg taacgaccga ggcgagtggc tcaagaacct caagtacggt   600
gttttcggtc tgggcaaccg acagtacgag cacttcaaca aggttgccaa ggttgtcgac   660
gacatcctcg tcgagcaggg tgcccagcga ctcgtccagg tcggctcgg  tgatgatgac   720
cagtgcatcg aggacgactt cactgcctgg cgagaggctc tgtggcccga gctcgacacc   780
attctgcgag aggaaggtga caccgccgtt gccacccct  acaccgccgc cgtcctcgag   840
taccgagtct ccatccacga ctccgaggat gccaagttca acgacatcaa catggccaac   900
ggtaacggct acaccgtctt tgacgcccag caccctaca  aggccaacgt cgccgtcaag   960
cgagagctcc acaccccga  gtccgaccga tccgagtt   ttgatctgt  tgacattgct  1020
ggttccggtc tgacctacga gactggtgac cacgttggtg tcctctgtga caacctgtcc  1080
gagactgtcg acgaggctct gcgactcctc gacatgtccc ccgacactta cttctctctg  1140
cacgccgaga agaggacgg  tactcccatc tcttcttctc tgcccctcc  cttccctcc   1200
tgcaacctgc gaaccgctct gacccgatac gcctgcctcc tcttctctcc caagaagtct  1260
gctctcgttg ctctgccgc  ccacgcctcc gaccccaccg aggctgagcg actcaagcac  1320
ctcgcctctc ccgctggcaa ggacgagtac tccaagtggg ttgtcgagtc ccagcgatct  1380
ctgctcgagg tcatggccga gttccctcc  gccaagcccc ctctcggtgt tttcttcgcc  1440
ggtgttgctc cccgactcca gccccgattc tactccatct cctcttcctc caagatcgct  1500
gagactcgaa tccacgttac ctgtgctctg gtctacgaga gatgcccac  cggccgaatc  1560
cacaagggtg tctgctccac ctggatgaag aacgccgttc cctacgagaa gtccgagaac  1620
tgttcctctg ctcccatctt tgtccgacag tccaacttca gctcccctc  cgactccaag  1680
gtcccatca  tcatgattgg cccgggtacc ggcctgcccc ccttccgagg cttcctgcag  1740
gagcgactcg ccctcgtcga gtccggtgtc gagctcggcc cctccgtcct cttctttggc  1800
tgccgaaacc gacgaatgga cttcatctac gaagaggagc tccagcgatt cgtcgagtcc  1860
ggtgctctcg ccgagctctc cgttgccttc tcccgagagg gtcccaccaa ggagtacgtc  1920
cagcacaaga tgatggacaa ggcctccgac atctggaaca tgatctccca gggcgcctac  1980
ctctacgtct gcggtgacgc caagggtatg gcccgagatg tccaccgagt tctgcacacc  2040
attgcccagg agcagggctc catgactcc  accaaggccg agggtttcgt caagaacctc  2100
cagacctccg gccgatacct ccgagatgtc tgg                               2133

SEQ ID NO: 25           moltype = DNA   length = 1419
FEATURE                 Location/Qualifiers
misc_feature            1..1419
                        note = UGT2_10b CpO for Y. lipolitica
source                  1..1419
                        mol_type = other DNA
                        organism = synthetic construct
SEQUENCE: 25
atggccacct ccgactccat tgttgacgac cgaaagaagc tccacattgt catgttcccc    60
tggctcgcct ttgccacat  catccccat  ctcgagcttt ccaagctcat tgcccagaag   120
ggcacaaagg tttccttcct ctccaccacc aagaacattg accgactctc ctcccacatc   180
tctcccctca tcaactttgt caagctcacc ctccccgag  tccaggagct cccgaggac   240
gccgaggcca ccactgatgt ccaccccgag atatcccct  acctcaagaa ggcctccgac   300
ggcctccagc ccgaggtcac tgagttcctc gagcagcact ctcccgactg gatcatctac   360
gactacaccc actactggct ccccgagatt gccaagtctc tcggtgtctc tcgagcccac   420
ttctccgtca ccaccccctg ggccattgct tacatgggtc ccactgccga tgccatgatc   480
```

```
aacggttccg actaccgaac cgagcttgag gacttcaccg tccctcccaa gtggttcccc  540
ttccccacca ccgtctgctg gcgaaagcac gatctggccc gactcgtccc ctacaaggct  600
cccggtatct ccgacggtta ccgaatgggc ctcgtcatca agggctgcga ctgtctgctc  660
tccaagacct accacgagtt cggtactcag tggctccgac ttctcgagga gctgcaccga  720
gtcccgtca tccccgttgg tctgctccct ccctccatcc ccggctctga caaggacgac  780
tcttgggttt ccatcaagga gtggctcgac ggccaggaga agggctccgt tgtctacgtt  840
gctctcggtt ccgaggttct cgtcacccag gaagaggttg tcgagcttgc tcacggtctg  900
gagctgtccg gtctgccctt cttctgggcc taccgaaagc caagggtcc cgccaagtcc  960
gactccgtcg agcttccga tggtttcgtc gagcgagtcc gagatcgagg tctggtctgg  1020
acctcttggg ctccccagct ccgaatcctc tcccacgagt ccgttgctgg tttcctcacc  1080
cactgcggtt ccggctccat tgtcgagggc ctcatgttcg gccacccctct catcatgctc  1140
cccatcttcg gtgaccagcc cctcaacgcc cgactccttg aggacaagca ggtcggtatc  1200
gagatccccc gaaacgagga agatggttct ttcacccgag actctgttgc cgagtctctg  1260
cgactcgtca tggtcgagga agagggtaag atctaccgag gaaggccaa ggagatgtcc  1320
aagctctttg gcgacaagga cctccaggac cagtacgtcg acgactttgt cgagtacctc  1380
cagaagcacc gacgagctgt tgccattgac cacgaaagc                          1419

SEQ ID NO: 26           moltype = DNA  length = 1758
FEATURE                 Location/Qualifiers
source                  1..1758
                        mol_type = other DNA
                        organism = Yarrowia lipolytica
SEQUENCE: 26
atggaatgga tttcacatct ggagaacgat gacgatgtgc tggaaatcga ggactacaag  60
gtgcgcaagg acgcgctgct gatcgccatt caagtaaccc agaacgccat taacaacgga  120
actcttcata aggccttgga ggcagccttc gatgctgtga ctgacagaat cgtcatatcg  180
ccgcaagatt acaccggcgt tatgctgttc ggtgcctcca tgcagtctga ggacgacggt  240
gacgagttcg atgatgagtc agatacacat ttcattctca agctgggcct tcctaccgct  300
gctcagatca aacgactcaa acgactggca gaggaccctg atctgggtga gaggttcaag  360
gtgcaggaag agcctcacct gatggacgtg ttttcgaca tgaaccgcca ttttatcaac  420
atggcaccca acttcgcgtc cagacgaatc atctatatca cagacgacga tacccccacg  480
acgaatgagg acgatatcaa caagacacga gttcgaattg aggatctaag ccatctcaag  540
gtgaaggtcg agcctctttt gatcaaccct tcggaagaca agacgttcga ctcctccaaa  600
ttctacgctc ttgtgttcaa cgaagacaca tctgtggagc cggttgaggc gatcgatttg  660
aagcagttta tcaacaaaag aaacgtgctc aatcgatcac tgttcaatgt caaaatggaa  720
atcggagaag gtcttgttgt cggagtaaga ggataccttc tttatgcgga acaaaaaggct  780
acttcaacaa cccgaaaggc ctgggtttac actggaggtg agaaaccccga gattgccaaa  840
ttagaatcgc aggccgtcac tattgaaagt ggcagaagcg tggacaaggc agatctgaga  900
aagctttca agtttggaaa tgactatgtt ccttctcacag aagaacagct gacgcaaatc  960
cggtactttg gagagccaat tattcgaatt ctcggcttcc acaattcctc ggacttctcc  1020
gagctcttca tccacagtgt ccgatcgtca atgttcctat atcccactga tgagaagctt  1080
gtgggttcga ttcgagcctt tcagcactc tatcagagtc tcaagaacaa ggataagatg  1140
gctctgcct gggttattgt ccgcaagggc gccaaaccta ttctggctct tcttattcct  1200
tcaactaagg agatcgaagg tcttcatatg gtcttcttgc cttttacaga tgatattcga  1260
caagaaccaa agactgaact tgtgtctgcc gcccctgagc tcgtgacgc aaccaagaat  1320
attttcactc gtctacgcat gcctggcgga tttgagtcgc aaagatacc caaccccgt   1380
ctacagtggc attaccgagt tgtacgagcc atggccctc aggagaggt tcccaaggta  1440
cccgaagaca agacgacacc aaagtatcgg tctattgata ctcgagttgg tgatgccatc  1500
gaggaatgga acaaggtgtt gcagagcagc tccaagcgac ctgcggagga tatctgtaag  1560
gctgagaaga agtcaagag ttctgacgcg ggccctccgt ccaacgagca aatgcaaaat  1620
atggttgaga atgacattgt cggcaagctg accgtcgcag aactcagggc ttggggtgct  1680
gctaacaatg ttgagcccaa tggtagcaag ttgaagaagg actgggttga ggtggtcaaa  1740
aagtactatg ggaagtga                                                1758

SEQ ID NO: 27           moltype = DNA  length = 4245
FEATURE                 Location/Qualifiers
source                  1..4245
                        mol_type = other DNA
                        organism = Yarrowia lipolytica
SEQUENCE: 27
atgggtaaaa ccgaagtgac acaggagagt ctagaatgcg ggtcggtcac gtcctcgctg  60
gggaaaaagc ccttctccat catcacactc ttcaccggca gacgcattcc tccggtacct  120
actgaaaaac cagattcggc cgaagaacgg gccgggattc tgtcaaaatt gacctggcaa  180
tggcttagtc cattgttgaa aactggttac ttacgaacgt gagatctgta  240
aaagtgagag agaaactc ggcggctgtg atccagcagc gacttgaatc caatctcgaa  300
aaacaatacg ccaagtacca cgccaaactg ctcaagaaag gactctcgga gcaagaggcg  360
catctcaagc tgcaagattc agccaaaccc ctcgtcttgg ctcttaacca gacgtttttt  420
tggaagttct ggctagccgg actgtttgcc ctagtcaagg acctctgtgg aatcgcctca  480
gctatggtgt cacgtgttct gatcgaatac attcaagaca gatatctcta caggggaca  540
gaccgggaac ctaaggtcgg ccgaggagtc ggccctcga taggcctatt tctactggcc  600
gtaggagtca ctttcttctt caaccacatg ttctacaatg tcaagatggt tggagctcag  660
gctcgtgcag ctctggtggc cgtcatctac agcaagagta cccgtttgag cgccaagggc  720
cgagctcaat acaccacagg caagatcaca aacttggcag ctattgacgc acatcgagtt  780
gatctcagtt gtgaatctt ccactacatt actatctttt tgcctgttgt gggttgtgcc  840
attgctgtac tcgtggtcaa cctcaaggtc gcagctctag ttggaattgc gaccatgatt  900
gtcttgatct ttgtcgtcgc aggcataccc atcttctcta tgaagctgcg agccatcatt  960
gtcaagctca cggataagcg agtcacgtat atccgagaag ctctgcagtc gattagaatc  1020
atcaagtact acggctggga ggttcctttac tgtgacaaga tcaagaaggt gcgtcttgac  1080
gagacccgta actacgccaa gatgggctcg attcgaggaa cagccattgg tatgtttcag  1140
```

```
gcactcccta ttttggcagg agcgttgtct ttcatcacct acgctgctct aggtcatgga 1200
actgatcctg ctcgaatgtt ctcttctctg acgcttttca atttactcct gcctgctctt 1260
gctgttcttc cccaggccct ccaggctgct ggagacgctc gagtggctct cagacgtatc 1320
cagcggttcc ttggggccga ggagtcgact cccactacag ttttgacgc tactcttgaa 1380
tctactgatg acgctgtgat tgtggaagac gcctcttca tctggccaga agttgtcgat 1440
gataagagcg acaaagagaa ggctaaagat gcaaagaagg aggaaaagga taagaagaag 1500
gccgagaaga aggccaagaa ggcggccaag aaggcggcca aggagatcgc ggtggttgtg 1560
gaagaggagg tggaacacga aaagaccgag ggatccagtg agtctgaaaa gggtactctt 1620
aagtcgactt tcaagggctt caacaacctg tctttcaaaa tcaagcgggg tgaatttgtc 1680
gttgttaccg gtcccattgg ttctggaaag tcgtctcttc ttgctgccat cactggatct 1740
atggttttga caggcggttc cgtgcgagtg tcgtccacag agtggattgg atgtctggag 1800
ccgtggattc aaaacgccac agttcgagat aacattgtgt ttgggcgaaa attcgactct 1860
gaatggtata gaactgtggt tactgcctgt cagctgagcc aggatctcaa aataatgact 1920
cacggagaca ataccatgat tggagagcga ggcatccata tttcgggcgg tcaaaaagct 1980
cgaatcaacc tcgcacgtgc tatatatgga aaccccgaga ttctcatcat ggacgacgtc 2040
ctgtcggctg tggacgctcg agtaggtgct ggtattgtgg acgattgtct tcgaggctta 2100
gccaagaact ccactcgaat tctggccacc atcagctgt ctgtgctgcc taaggctgat 2160
catgtgattt tcatgatgc cgaaggccag tttcatattg gtacgtacca agagctgaag 2220
gctgacaatg agcagttcaa ggctcttttg gcggctggtt ccatgtccaa ggaggaggtg 2280
gttgctgtcg acgagactga ggttgttatt gaaggcgatc ttgaagacga ctgcgataac 2340
aaggaggagt atgaggatgc agctgagacc atttccattt tggcagatgc cactcaagag 2400
ctgcaaaagg tgaccactac agtctcggca tttgaggaga acgataacat gatggaggaa 2460
gaagagcgaa tgagagatgc agttggtttg catgtgtact ggcagtattt tcgtcaggcc 2520
aaccccagta gggtcaaggt aatgatgttc attggcatga tcttcattc catgattgtg 2580
attgcctttc tgtttgtctt cacatctgta tggctctcgt tctggacagg tgaccgtttc 2640
catgcctcca gaaacttcta caccggaatt tacatcatgc tgggtattct tctgcttctt 2700
gctgtggcag gatacatgat tgtcaatgag atcaactctg ccatggcagc aagaaatcta 2760
cacaatcatg ctttggactc ggtgttcgct gcacgaactt ctttcttcga taccactcct 2820
cagggtcgta tcatcaaccg gttcacccga gacacagact ctctggataa cgagctggct 2880
atgcgattga ctatgttgtt ctttggcgtc tccgcattct tctccaactt cctgcttact 2940
tgtgtctacg ttccttatgt gactcttgtg cttgtccctg tcggttttgt cttctacgtt 3000
tctctaggtt actaccgaaa gtcagctcgt gaagtcaagc gaattgactc cattgaacgg 3060
tcgcacatga tgagtgtctt caacgagtcc atttccggta tgcccgtcat catcatgtac 3120
aaggcccagc atcggctcat gaacaagctt caggctactc tcgatgatat ggacagtgag 3180
tacttcctca ctgctgcaaa ccagcgatgg ctgtctctcc gtctggatgg tctgggttct 3240
ttggtcgttc tggtggccac tattcttgtt gctgtcggag tctttgatct cacccctcc 3300
aacatggggtc tgatcatttc cgcggcctcc tttatccccg aagtcatgtc tatggttgcc 3360
caggccgttg ctgaactcga aaactgcatg aacgccacag agcgaattct ttactacaag 3420
gacaacattc ctgctgaggc tgctcgaaa gtggacggta cagcgctga ccagcgaccc 3480
aactggcctg agcagggagc catcagcttc aacaatgtgt ccatgaagta ccgagatgga 3540
cttccttacg tgctcaagtc attgtctgtc gactttcagg gaggacacaa ggtgggtatc 3600
tgtggacgaa caggagccgg taagagtacc atcttgcaga ctctgtatcg aattgtggag 3660
cttgctgagg gttctattac tattgatggt gttgacattt cgactattgg actgcatcag 3720
cttcggtctc agttgtccat cattcccag gagccagttt tgttcctggg caccatccgg 3780
tctaatttgg atcctctgga gcaatactct gatgctgagc tatgggggttc tctacgacgg 3840
tctggacttc tcgatgaagg agagactgag ggtaagtttc atctggatca aaaggtggag 3900
gctgacggca gcaacttctc tctaggtgag cgacagctgc tgactctagc ccgagcactg 3960
cttagaaaca ccaaaattt ggtgctggac gaagccacat caaatgtcga ctacaagacg 4020
gacaagctgt tcaggagac catttcacgg gagtttggcc actgcacgat tctgtgtatc 4080
gcccatcgac tgcgaaccat tgccaagtat gatcgtattt tggtgcttga gtccggcgag 4140
atcaaccagt acgacacgcc ctggaacttg tacaacgaca aggagggtat tttccgaggt 4200
atgtgtgaca cctccgggtt gaacgaggta gacttcaaca agtaa          4245
```

SEQ ID NO: 28        moltype = DNA  length = 4245
FEATURE               Location/Qualifiers
misc_feature       1..4245
                      note = YALI0E25201g CpO for Y. lipolitica
source              1..4245
                      mol_type = other DNA
                      organism = synthetic construct
SEQUENCE: 28

```
atgggtaaga ccgaggtcac tcaggagtct ctcgagtgcg gttccgtcac ctcctctctc  60
ggcaagaagc ccttctccat catcactctc ttcaccggcc gacggatccc tcccgtcccc 120
actgagaaga ccgactccgc tgaggagcga gccggcactc tctccaagct gacgagtcac 180
tggctctctc ctctgctcaa gaccggttac ctccgaaaca tcgagcgaga ggatctgtac 240
aaggtccgag agcgaaactc cgctgccgtt atccagcagc gacttgagtc caacctggag 300
agcagtacgc ccaagtacca cgccaagctc ctcaagaagg tctgtctga gcaagaggcc 360
cacctcaagc tgcaggactc tgccaagccc tgtcctgg ccctcaacca gaccttcttc 420
tggaagttct ggctcgctgg tctgttcgcc ctcgtcaagg acctctgtgg cattgcttcc 480
gccatggttt cccgagttct cattgagtac atccaggacc gatacctca ccgaggtacc 540
gaccgagagc ccaaggtcgg ccgaggtgtc ggtccctcca tcgactcttc cctgctgacc 600
gttggtgtca ctttcttctt caaccacactg ttctacaacg tcaagatgggt tggtgcccag 660
gcccgagctg ccctcgtcgc tgtcatctac tccagtccca ccgactgtc gccaagggt 720
cgagcccagt acaccaccgg caagatcacc acctcgtcac ccattgatgc tccaccgagt 780
gatctgtctt gcgagtcttt tcactacatc actatcttcc ttcccgtcgt cggctgcgct 840
attgccgtcc tcgttgtcaa cctcaaggtt gctgctctcg tcggtattgc cactatgatt 900
gtcctcatct ttgtcgttgc tggtatcacc atcttctcca tgaagctccg agccatcatc 960
gtcaagctca ccgacaagcg agtcacctac atccgagagg ctctccagtc catccgaatc 1020
atcaagtact acggctggga ggttcctac tgcgacaaga ttaagaaggt ccgactcgac 1080
```

```
                                                -continued
gagactcgaa actacgccaa gatgggctcc attcgaggaa ccgctattgg tatgttccag   1140
gctctcccca tcctcgccgg cgctctgtct tttatcacct acgccgccct cggtcacggc   1200
accgaccccg cccgaatgtt ctcttctctc accctcttca acctgctgct ccccgctctt   1260
gccgttctcc cccaggccct ccaggccgct ggtgacgccc gagtcgccct cgacgaatc    1320
cagcgattcc tcggtgctga ggagtccacc cccaccactg tcttcgatgc tactcttgag   1380
tctaccgacg acgccgtcat cgtcgaggac gcctccttca tttggcccga ggtcgttgac   1440
gacaagtccg acaaggagaa ggccaaggat gctaagaaag aggagaagga caagaagaag   1500
gctgagaaga agccaagaa ggccgctaag aaggcagcca aggagatcgc cgttgttgtt    1560
gaggaagagg tcgagcacga gaagaccgaa ggctcctccg agtccgagaa aggtaccctc   1620
aagtccacgt tcaagggttt caacaacctg tcttttcaaga tcaagcgagg tgagttcgtt   1680
gtcgtcactg gtcccatcgg ctccggtaag tcctctctgc tcgctgccat taccggttcc   1740
atggttctga ccggtggttc tgtccgagtc tcttccaccg agtggatcgg ttgcctcgag   1800
ccttggatcc agaacgccac cgtccgagac aacattgtct tcggccgtaa gtttgactcc   1860
gagtggtacc gaaccgttgt caccgcctgc cagctctccc aggacctcaa gatcatgacc   1920
cacggcgata acaccatgat tggtgagcga ggtatcactg tctccggtgg tcagaaggcc   1980
cgaatcaacc tggcccgcgc gatctacggt aaccccgaga ttctcatcat ggacgacgtc   2040
ctctccgccg tcgacgccag ggtcggagcc ggtatcgtcg atgactgtct gagaggcctc   2100
gccaagaact ctacccgaat cctcgccacc accagctct ctgttctccc caaggccgaa   2160
cacgtcatct ttatgacgc cgagggtcag ttccacattg gcacctacca agagctcgag   2220
gctgataacg agcagttcaa ggctctcctc gctgccggct ctatgtccaa agaggaagtc   2280
gttgccgttg acgagactga ggttgtcatt gagggtgacc tcgaggacga ctgtgacaac   2340
aaggaagagt acgaggatgc tgccgaagact atctccattc tcgccgacgc cacccaggag   2400
ctccagaagg ttaccaccac cgtttctgct tttgaggaga cgacaacat gatggaggaa    2460
gaagaacgaa tgcgagatgc cgtcggtctg cacgtctact ggcagtactt ccgacaggcc   2520
aacccctctc gagtcaaggt catgatgttc attggtatga ttttcatctc catgattgtc   2580
attgccttcc tcttcgtctt cacctccgtc tggctctcca tttggaccgg tgaccgattc   2640
cacgcttccc gaaacttcta caccggcatc tacatcatgc tcggtatcct ccttctgctc   2700
gccgtcgccg gttacatgat cgtcaatgag atcaactctg ccatggccgc ccgaaacctg   2760
cacaaccacg ccctcgactc cgtcttcgcc gctcgaactt cttttcttcga caccactccc   2820
cagggccgaa tcattaaccg attcacccgg gacaccgact ccctcgataa cgaactggcc   2880
atgcgactca ccatgctctt tttcggtgtt tccgccttt tctccaactt cctcctcacc    2940
tgtgtctacg ttccctacgt caccctggtt cttgtccccg ttggtttcgt cttctacgtt   3000
tccctcggtt actaccgaaa gtccgcccga gaggtcaagc gaatcgactc cattgagcga   3060
tcccacatga tgtccgtctt caacgagtcc atctccggta tgcccgttat catcatgtac   3120
aaggcccaac accgactcat gaacaagctc caggccaccc tcgacgacat ggactccgcc   3180
tacttcctga ccgctgccaa ccagcgatgg ctctcccctcc gactgacgg tcttggctct   3240
cttgttgtcc tcgtcgccac cattcttgtc gccgtcggtg tctttgacct caccccctcc   3300
aacatgggcc tcatcatctc tgctgcctct ttcatcccg aggtcatgtc catggtcgcc   3360
caggccgttg ctgagctcga gaactgcatg aacgctaccg agcgaatcct ctactacaag   3420
gacaacatcc ccgccgaggc tgctcgagag gtcgacgtat ccgagcttga tcagcgaccc   3480
aactggcccg agcagggcgc catctccttc aacaacgtgt ccatgaagta ccgagatggt   3540
ctgccctacg tcctcaagtc tctctccgtc gacttccagg cggcacaa ggtcggtatc     3600
tgcggacgaa ccggtgccgg caagtccact atcctccaga cctgtaccg aatcgtcgag   3660
ctggccgagg gctccatcac cattgatggt gtcgacatct ccaccattgg cctgcaccag   3720
ctccgatccc agctgtccat catccccag gagcccgttc tgttccttgg caccatccga    3780
tccaacctcg atccctcga gcagtactcc gacgccgagc tctggggttc tctccgacga   3840
tccggccttc tggacgaggg tgaaaccgag ggtaagttcc acctcgacca gaaggtcgag   3900
gccgatggtt ccaacttctc tctgggtgag cgacagctcc tcaccctcgc ccgagccctt   3960
ctgcgaaaca ccaagattct tgttctcgac gaggctacct ccaacgtcga ctacaagacc   4020
gataagctcg tccaggagac aatctcccga gagttcggtc actgcaccat tctctgtatc   4080
gcccaccgac tgcgaaccat cgctaagtac gaccgaattc tcgttctcga gtccggccag   4140
atcaaccagt acgacacccc ctggaacctc tacaacgaca aggaaggtat cttccgaggc   4200
atgtgcgaca cctccggcct caacgaggtc gactttaata aataa                  4245

SEQ ID NO: 29        moltype = AA  length = 1414
FEATURE              Location/Qualifiers
source               1..1414
                     mol_type = protein
                     organism = Yarrowia lipolytica
SEQUENCE: 29
MGKTEVTQES LECGSVTSSL GKKPFSIITL FTGRRIPPVP TEKPDSAEER AGILSKLTWQ   60
WLSPLLKTGY LRNIEREDLY KVRERNSAAV IQQRLESNLE KQYAKYHAKL LKKGLSEQEA   120
HLKLQDSAKP LVLALNQTFF WKFWLAGLFA LVKDLCGIAS AMVSRVLIEY IQDRYLYRGT   180
DREPKVGRGV GPSIGLFLLA VGVTFFFNHM FYNVKMVGAQ ARAALVAVIY SKSTRLSAKG   240
RAQYTTGKIT NLAAIDAHRV DLSCESFHYI TIFLPVVGCA IAVLVVNLKV AALVGIATMI   300
VLIFVVAGIT IFSMKLRAII VKLTDKRVTY IREALQSIRI IKYYGWEVPY CDKIKKVRLD   360
ETRNYAKMGS IRGTAIGMFQ ALPILAGALS FITYAALGHG TDPARMFSSL TLFNLLLPAL   420
AVLPQALQAA GDARVALRRI QRFLGAEEST PTTVFDATLE STDDAVIVED ASFIWPEVVD   480
DKSDKEKAKD AKKEEKDKKK AEKKAKKAAK KAAKEIAVVV EEVEHKTE GSSESEKGTL    540
KSTFKGFNNL SFKIKRGEFV VVTGPIGSGK SSLLAAITGS MVLTGGSVRV SSTEWIGCLE   600
PWIQNATVRD NIVFGRKFDS EWYRTVVTAC QLSQDLKIMT HGDNTMIGER GITVSGGQKA   660
RINLARAIYG NPEILMMDDV LSAVDARVGA GIVDDCLRGL AKNSTRILAT HQLSVLPKAD   720
HVIFMDAEGQ PHIGTYQELE ADNEQFKALL AAGSMSKEEV VAVDETEVVI EGDLEDDCDN   780
KEEYEDAAET ISILADATQE LQKVTTTVSA FEENDNMMEE EERMRDAVGL HVYWQYFRQA   840
NPSRVKVMMF IGMIFISMIV IAFLVFTSV WLSFWTGDRF HASRNFYTGI YIMLGILLLL   900
AVAGYMIVNE INSAMAARNL HNHALDSVFA ARTSFFDTTP QGRIINRFTR DTDSLDNELA   960
MRLTMLFFGV SAFFSNFLLT CVYPVYTLV LVPVGFVFYV SLGYYRKSAR EVKRIDSIER   1020
SHMMSVFNES ISGMPVIIMY KAQHRLMNKL QATLDDMDSA YFLTAANQRW LSLRLDGLGS   1080
LVVLVATILV AVGVFDLTPS NMGLIISAAS FIPEVMSMVA QAVAELENCM NATERILYYK   1140
```

```
DNIPAEAARE VDGTELDQRP NWPEQGAISF NNVSMKYRDG LPYVLKSLSV DFQGGHKVGI    1200
CGRTGAGKST ILQTLYRIVE LAEGSITIDG VDISTIGLHQ LRSQLSIIPQ EPVLFLGTIR    1260
SNLDPLEQYS DAELWGSLRR SGLLDEGETE GKFHLDQKVE ADGSNFSLGE RQLLTLARAL    1320
LRNTKILVLD EATSNVDYKT DKLVQETISR EFGHCTILCI AHRLRTIAKY DRILVLESGE    1380
INQYDTPWNL YNDKEGIFRG MCDTSGLNEV DFNK                                1414

SEQ ID NO: 30           moltype = DNA   length = 1000
FEATURE                 Location/Qualifiers
source                  1..1000
                        mol_type = other DNA
                        organism = Yarrowia lipolytica
SEQUENCE: 30
cggttgagag ttcaagaaca cgaccaagta accccgagaa agtgtcgatg gatacagaga      60
aaacaatatc gcagatattg acaacaaact tgcaacgaga gccctctaca tgctccaata    120
ttcttcttcc agacctaccc gttcacacaa ctacaagttg ccgccttaaa caacaacgtg    180
gtcaactccg gagttaacag aagcataata atgtgatgga atttggaggt tggggagaga    240
cagtttggac cggagacacg ccacggggaa atcatcataa acattggtaa aatgccaaaa    300
aaaatttata catggtagca aaagcatcct ggagaactca taagtatgtc agggtcccaa    360
aaacctcgtt aatggaggcc tgcggacttc ttccgtgaca ttgtgaacca ttaatacaac    420
ctgaaaagac catctgcaaa acaccagtga tagtggttcc aacgcaactt cgtgcacact    480
caacgctacc actgctagac ctaccgccgt tagacctatt gtatcgccgc caccgttctt    540
aaatgcagat gaagtaaaac atgccgttcg gtccaatagt taatgttgct ccgccatgct    600
cagttttttt tcttttcttt cggcaaaata accttcgcag tcatgtgaga tatcgcacga    660
caagatgtga ctaacatgcc aacggcggct gcccccaagg tgtatatgag taccaaatta    720
gggcatgata caagaatacc tttcgaaaag ccggaacaag ataaagcagc caacccctta    780
taacggccag ctagcgccaa acttgctcgc ccgagcccc accgcttct catccgtacg    840
ccatttcgtg ccacgtatcc agaaagttct actcccagca cagggttagg ggtgttgcca    900
ttctgggtca ctccccacca ccacagcatg ttttttcctc tctcccgaca accacaactc    960
tctagtttac actaaccaca cacgacacca attttaaaaa                         1000

SEQ ID NO: 31           moltype = DNA   length = 300
FEATURE                 Location/Qualifiers
source                  1..300
                        mol_type = other DNA
                        organism = Yarrowia lipolytica
SEQUENCE: 31
atgcaaacca gtaatttat tgtgtagtct aggattgaca tttgattacc gtgtacatta     60
aatgaatgat tgtaaattga agaggaagt gtagcaatgg ttgaatgggg agtaatgggt    120
tactgtaatt gcatgtccca ccttctttgc accgttcttg ttgtatacag tacaatacat    180
acatacccta tgtatgtttt ttgtgaatat gatgagtcta ctactacagt aaatcagctt    240
tgatccctgc cagaatgtgt gtacacagta tgggactctc atcccctgta caatataata    300

SEQ ID NO: 32           moltype = DNA   length = 912
FEATURE                 Location/Qualifiers
misc_feature            1..912
                        note = carG nucleic acid sequence codon optimized for Y.
                        lipolitica
source                  1..912
                        mol_type = other DNA
                        organism = synthetic construct
SEQUENCE: 32
atgctcaact ctcacaaccg aaccgaggag cgatccaccg aggatattat tctcgagcct     60
tacacctacc tcatttctca gcccggaaag gacattcgag ctaagctcat ttctgccttt    120
gacctctggc tgcacgttcc taaggatgtt ctttgcgtca tcaacaagat tatccggtatg    180
ctgcacaacg cctctcttat gattgacgat gttcaggacg actctgatct ctgacgagga    240
gtccccgttg ctcaccacat ttacggtgtc cctcagacta ttaacaccgc taactacgtg    300
attttcctcg cccttcagga ggttatgaag ctgaacatcc cttctatgat gcaggtgtgt    360
accgaggagc ttattaacct ccaccgaggt cagggaattg agctgtactg gcagagattcc    420
ctcacttgtc ccactgagga ggagtacatt gatatggtta acaacaagac ctctggcctc    480
cttcgacttg ccgtccgact gatgcaggct gcttctgagt ccgacatcga ctacacccct    540
ctcgtcaaca ttatcggaat tcacttccag gttcgagatg actacatgaa cctccagtcc    600
acctcttaca ctaacaacaa gggcttttgc gaggacctga ccgagggaaa gttctccttc    660
cctattattc acgctattcg aaaggacccc tctaaccgac agctcctgaa cattatctct    720
cagaagccca cctccattga ggttaagaag tacgctcttg aaaggctgaa    780
tcttttgagt acgttcgaga gttccttcga cagaaggagg ctgagtccct gaaggagatc    840
aagcgacttg gcggcaaccc tctcctcgag aagtacattg agactattcg agtcgaggct    900
actaacgact aa                                                        912

SEQ ID NO: 33           moltype = DNA   length = 1419
FEATURE                 Location/Qualifiers
misc_feature            1..1419
                        note = UGT2_6b CpO for Y. lipolitica
source                  1..1419
                        mol_type = other DNA
                        organism = synthetic construct
SEQUENCE: 33
atggctactt ccgactccat tgtcgacgac cgaaagaagc tccacattgt catgttcccc     60
tggctcgcct ttgccacaca cattccctac ctcgagcttt ccaagctcat tgcccagaag    120
ggccacaagg tttcttcct ctccaccacc aagaacattg accgactctc ctcccacatc    180
```

```
tctcctctca tcaacgttgt ccagctcacc ctcccccgag tccaggagct gcccgaggac    240
gccgaggcca ccaccgatgt ccaccccgag gatatcccct acctcaagaa ggcctccgac    300
ggtctgcagc ccgaggtcac cgagttcctc gagcagcact ctcccgactg gatcatctac    360
gactacaccc actactggct cccctccatt gccaccaagc acggtgtctc tcgagcccac    420
ttctccgtca ccaccccctg ggccattgcc tacatggcgc ccactgctga cgccatgatc    480
aacggttccg atggccgaac caccccgag gacttcactg tccctcccaa gtggttcccc    540
ttccccacca aggtctgctg gcgaaagcac gatctggccc gactcgttcc ctacaaggcc    600
cccggtatct ccgacggcta ccgaatgggt ctggtcatca agggctgcga ctgtctgctc    660
tccaagacct accacgagtt tggcacccag tggctccgac tcctcgagac tctccaccga    720
aagcccgtca tccccgtcgg tctgctccct ccctccatcc ccggctccga caaggacgac    780
tcttgggttt ccatcaagga gtggctcgac ggccaggaga agggctctgt tgtctacgtt    840
gctctcggtt ccgaggttct cgtcacccag gacgaggttg ttgagctggc ccacggtctg    900
gagctgtccg gcctcccctt cgtctgggct taccgaaacc ccaagggtcc cgccaagtcc    960
gactccgtcg agcttcccga tggtttcgtc gagcgagtcc gagatcgagg tctggtctgg   1020
acctcttggg ctccccagct ccgaatcctc tcccacgagt ccgtctgtgg tttcctcacc   1080
cactgcggtt ccggctccat cgtcgagggt ctgatgttcg gccacccct catcatgctc   1140
cccatcttcg gtgaccagcc cctcaacgcc cgactccttg aggacaagca ggtcggtatc   1200
gagatccccc gaaacgaaga ggacggttcc ttcacccgag actctgttgc tgagtctctc   1260
cgactcgtca tggtcgagga gagggtaag atctaccgag agaaggccaa ggagatgtcc   1320
aagctgttcg gtgacaagga tctccaggac cagtacgtcg acgactttgt cgagtacctc   1380
cagaagcacc gacgagctgt tgccattgac cacgagtct                          1419

SEQ ID NO: 34          moltype = DNA  length = 1341
FEATURE                Location/Qualifiers
misc_feature           1..1341
                       note = RT18 nucleic acid sequence CpO for Y. lipolitica
source                 1..1341
                       mol_type = other DNA
                       organism = synthetic construct
SEQUENCE: 34
atgtccacca ccctcaaggt cctcatgttc cccttcctcg cttacggcca catctctccc     60
tacctcaacg ttgccaagaa gctcgccgac cgaggcttcc tcatctacct ctgttccacc    120
cccatcaacc tcaagtccac catcaacaag atccccgaga gtacgccga ctccatccag    180
ctcatcgaac tccatctccc cgagcttccc gagctgcctc cccactacca caccaccaac    240
ggtctgcctc ccaacctcaa ccacatcctc cgacgagccc tcaagatgtc caagcccaac    300
ttctccaaga tcatgcagaa cctgaagccc gatctgctca tctacgacat tctccagcag    360
tgggccgagg atgtcgccac cgagcttaac atccccgccg tcaagctgct cacctctggt    420
gttgctgttt tctcttactt cttcaacctc accaagaagc ccgaggtcga gttccctac    480
ccgctatct acctccgaaa gatcgagctg gtccgatggt gcagaactct gtccaagcac    540
aacaaggaag gtgaggagca cgacgacggc ctcgcctacg gcaacatgca gatcatgctc    600
atgtccactt ccaagatcct cgaggccaag tacattgact actgcattga gctgaccaac    660
tggaaggtcg tccccgtcgg ctctctcgtc caggactcca tcaccaacga cgccgctgac    720
gacacatgg aactcattga ctggctcggt actaaggacg agaactccac cgtcttttgtc   780
tcttttggct ccgagtactt cctctccaaa gaggacgttg aagaggttgc cttcggtctg    840
gagctgtcca acgtcaactt catctgggtt gtccgattcc ccaagggtga ggagaagaac    900
ctcgaggacg ttctgcccaa gggcttcttc gagcgaatcg tgagcgagg ccgagtcctc    960
gacaagtttg ctccccagcc ccgaattctc aaccaccct ctaccggtgg tttcatctct    1020
cactgtggct ggaactccgc catggagtcc attgactttg gtgtcccat tgtcgccatg    1080
cccatgcagc tcgaccagcc catgaacgcc cgactcattg tcgagcttgg tgttgccgtc    1140
gagattgtcc gagatgatga tggtaagatc taccgaggtg agattgctga gactctcaag    1200
ggtgtcatca ccggcgagat tggtgagatc ctccgagcca aggtccgaga catctccaag    1260
aacctcaagg ccatcaagga cgaggagatg gacgttgctg cccaggagct gatccagctc    1320
tgccgaaact ccaataaata a                                              1341
```

STEVIOL GLYCOSIDE TRANSPORT

CROSS-REFERENCE TO RELATED APPLICATIONS

This application is a continuation of U.S. application Ser. No. 17/512,368, filed 27 Oct. 2021, which is a divisional of U.S. application Ser. No. 15/751,674, filed on 9 Feb. 2018 (now U.S. patent Ser. No. 11/297,862, issued 12 Apr. 2022), which is a 371 National Stage Application of PCT/EP2016/069356, filed 15 Aug. 2016, and claims benefit to U.S. Provisional Application No. 62/204,702, filed 13 Aug. 2015, the entire contents of each of which are incorporated herein by reference.

REFERENCE TO SEQUENCE LISTING SUBMITTED AS AN XML FILE (.xml)

Pursuant to the EFS-Web legal framework and 37 CFR §§ 1.821-825 (see MPEP § 2442.03(a)), a Sequence Listing in the form of an .xml file (entitled "Sequence_Listing_2919208-344003.xml" created on 31 Jan. 2024, and 80,922 bytes in size) is submitted concurrently with the instant application, and the entire contents of the Sequence Listing are incorporated herein by reference.

FIELD OF THE INVENTION

The present invention relates to a recombinant host capable of producing a steviol glycoside. The invention also relates to a process for the preparation of a steviol glycoside using such a recombinant host. The invention also relates to a fermentation broth comprising a steviol glycoside, a steviol glycoside and to a composition comprising two or more steviol glycosides. The invention further relates to a foodstuff, feed or beverage which comprises a steviol glycoside or a composition comprising two or more steviol glycosides.

DESCRIPTION OF RELATED ART

The leaves of the perennial herb, *Stevia rebaudiana* Bert., accumulate quantities of intensely sweet compounds known as steviol glycosides. Whilst the biological function of these compounds is unclear, they have commercial significance as alternative high potency sweeteners.

These sweet steviol glycosides have functional and sensory properties that appear to be superior to those of many high potency sweeteners. In addition, studies suggest that stevioside can reduce blood glucose levels in Type II diabetics and can reduce blood pressure in mildly hypertensive patients.

Steviol glycosides accumulate in *Stevia* leaves where they may comprise from 10 to 20% of the leaf dry weight. Stevioside and rebaudioside A are both heat and pH stable and suitable for use in carbonated beverages and many other foods. Stevioside is between 110 and 270 times sweeter than sucrose, rebaudioside A between 150 and 320 times sweeter than sucrose. In addition, rebaudioside D is also a high-potency diterpene glycoside sweetener which accumulates in *Stevia* leaves. It may be about 200 times sweeter than sucrose. Rebaudioside M is a further high-potency diterpene glycoside sweetener. It is present in trace amounts in certain *stevia* variety leaves, but has been suggested to have a superior taste profile.

Steviol glycosides have traditionally been extracted from the *Stevia* plant. In *Stevia*, (−)-kaurenoic acid, an intermediate in gibberellic acid (GA) biosynthesis, is converted into the tetracyclic diterpene steviol, which then proceeds through a multi-step glycosylation pathway to form the various steviol glycosides. However, yields may be variable and affected by agriculture and environmental conditions. Also, *Stevia* cultivation requires substantial land area, a long time prior to harvest, intensive labour and additional costs for the extraction and purification of the glycosides.

More recently, interest has grown in producing steviol glycosides using fermentative processes. WO2013/110673 and WO2015/007748 describe microorganisms that may be used to produce at least the steviol glycosides rebaudioside A, rebaudioside D and rebaudioside M.

Further improvement of such microoganisms is desirable in order that higher amounts of steviol glycosides may be produced and/or additional or new steviol glycosides and/or higher amounts of specific steviol glycosides and/or mixtures of steviol glycosides having desired ratios of different steviol glycosides.

SUMMARY OF THE INVENTION

The present invention is based on the identification of a protein which is capable of mediating steviol glycoside transport.

Accordingly, the protein may be overexpressed in a recombinant host (such as a microbial cell) in order to increase steviol glycoside transport out of the host. Alternatively, a host (such as a microbial cell) may be modified so as to express less of the protein than a corresponding non-modified version of the host. In this case, more steviol glycoside may be retained within the host which is then glycosylated to a steviol glycoside comprising a higher number of sugar moieties.

Thus, the invention relates to a recombinant host, for example a cell such as a microbial cell, which produces steviol glycoside outside the host to a greater degree than a corresponding host not overexpressing the protein. This may facilitate easier recovery of steviol glycosides. The invention also relates to a recombinant host capable of producing a steviol glycoside which overexpresses a heterologous polypeptide which mediates steviol glycoside transport.

Accordingly, the invention relates to a recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto.

The invention also relates to a recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.

The invention also relates to a recombinant host which comprises steviol glycosides (inside and/or outside the host) having a higher or lower average glycosylation number than a corresponding host not modified according to the invention.

The invention also relates to:
a process for the preparation of a steviol glycoside which comprises fermenting a recombinant host according to any one of the preceding claims in a suitable fermentation medium and, optionally, recovering the steviol glycoside;

a fermentation broth comprising a steviol glycoside obtainable by a process of the invention;

a steviol glycoside obtained by a process or a fermentation broth of the invention;

a composition comprising two or more steviol glycosides of the invention or obtainable by a process of the invention;

a foodstuff, feed or beverage which comprises a steviol glycoside or a composition of the invention.

DESCRIPTION OF THE SEQUENCE LISTING

Figure 1:
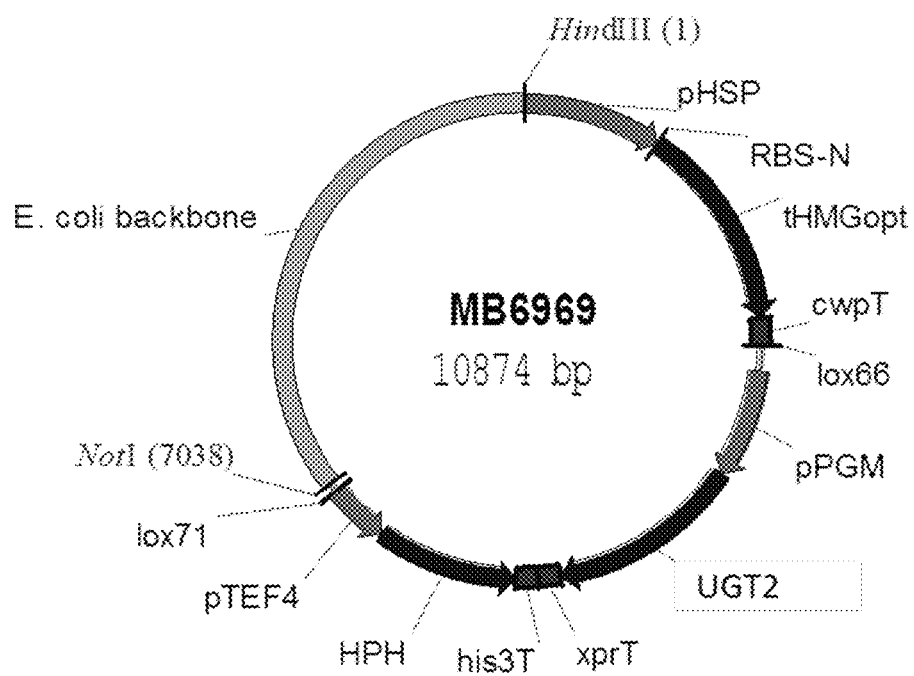
FIG. 1 sets out a schematic representation of the plasmid MB6969, encoding tHMG, UGT2_1a, HPH.

A description of the sequences is set out in Table 14. Sequences described herein may be defined with reference to the sequence listing or with reference to the database accession numbers also set out in Table 14.

DETAILED DESCRIPTION OF THE INVENTION

Throughout the present specification and the accompanying claims, the words "comprise", "include" and "having" and variations such as "comprises", "comprising", "includes" and "including" are to be interpreted inclusively. That is, these words are intended to convey the possible inclusion of other elements or integers not specifically recited, where the context allows.

The articles "a" and "an" are used herein to refer to one or to more than one (i.e. to one or at least one) of the grammatical object of the article. By way of example, "an element" may mean one element or more than one element.

The invention relates to the identification of a polypeptide which is capable of mediating steviol glycoside transport. Such a polypeptide may directly mediate steviol glycoside transport, i.e. may be a transporter protein, or may indirectly mediate steviol glycoside transport. Such a polypeptide may be capable of mediating transport of one or more steviol glycoside.

The invention relates to a recombinant host either overexpressing or having reduced expression of such a polypeptide. The terms recombinant host or recombinant cell may, depending on the context, be used interchangeably.

Such a polypeptide as described herein may be overexpressed in a recombinant host, such as a recombinant host cell, capable of producing one or more steviol glycosides. Such a cell may be capable of producing more of one or more steviol glycosides external to the cell than a corresponding cell which does not overexpress the polypeptide. That is to say, a recombinant cell according to the invention may have increased or decreased steviol glycoside transport in a comparison with a corresponding non-recombinant cell.

Accordingly, the invention provides a recombinant host capable of producing a steviol glycoside which overexpresses a polypeptide, the polypeptide being one which is capable of mediating steviol glycoside transport and which polypeptide comprises the amino acid sequence set forth in SEQ ID NO: 29 or an amino acid sequence having at least about 50% sequence identity thereto.

The expression of such a polypeptide may also be modified in a host, such as a recombinant host cell, such that it is reduced compared to a corresponding cell which has not been similarly modified. In this way, the amount of one or more steviol glycosides outside the cell may be reduced in comparison with a corresponding cell which has not been similarly modified. This may allow for increased glycosylation of one or more steviol glycosides within the cell compared with a corresponding cell which has not been similarly modified. Such a host may thus comprise steviol glycosides having a higher average glycosylation number compared with a corresponding cell which has not been similarly modified.

Accordingly, the invention provides a recombinant host capable of producing a steviol glycoside which has been modified, preferably in its genome, to result in a deficiency in the production of a polypeptide, the polypeptide being one which is capable of mediating steviol glycoside transport and which polypeptide comprises the amino acid sequence set forth in SEQ ID NO: 29 or an amino acid sequence having at least about 50% sequence identity thereto.

A host cell of the invention is a recombinant host cell. "Recombinant" in this sense means that the host cell is a non-naturally occurring host cell, for example modified by introduction of one or more nucleic acids using recombinant techniques. A nucleic acid used to modify a host cell to arrive at a recombinant host cell of the invention may be a naturally-occurring nucleic acid or a non-naturally occurring nucleic acid.

Thus, when used in reference to a host of the invention, "recombinant" indicates that a cell has been modified by the introduction of one or more heterologous nucleic acid or protein or the alteration of a native nucleic acid or protein, or that the cell is derived from a cell so modified. The term "heterologous" as used herein refers to nucleic acid or amino acid sequences not naturally occurring in a host cell. In other words, the nucleic acid or amino acid sequence is not identical to that naturally found in the host cell.

The invention relates to a recombinant host capable of producing a steviol glycoside which overexpresses a heterologous polypeptide which mediates steviol glycoside transport. Such a heterologous polypeptide may be obtained from or derived from a genus or species other than that of the host. Accordingly, if the recombinant host is a yeast, the heterologous polypeptide which mediates steviol glycoside transport may be obtained from or derived from a different genus or species of yeast.

For example, if the host cell is a *Saccharomyces* (e.g., *S. cerevisiae, S. bayanus, S. pastorianus, S. carlsbergensis*), the heterologous polypeptide which mediates steviol glycoside transport may be obtained from or derived from a *Candida* (e.g., *C. krusei, C. revkaufi, C. pulcherrima, C. tropicalis, C. utilis*), an *Issatchenkia* (eg. *I. orientalis*) or a *Yarrowia* (e.g., *Y. lipolytica* (formerly classified as *Candida lipolytica*)).

For example, if the host cell is a *Candida* (e.g., *C. krusei, C. revkaufi, C. pulcherrima, C. tropicalis, C. utilis*), the heterologous polypeptide which mediates steviol glycoside transport may be obtained from or derived from a *Saccharomyces* (e.g., *S. cerevisiae, S. bayanus, S. pastorianus, S. carlsbergensis*), an *Issatchenkia* (eg. *I. orientalis*) or a *Yarrowia* (e.g., *Y. lipolytica* (formerly classified as *Candida lipolytica*)).

For example, if the host cell is an *Issatchenkia* (eg. *I. orientalis*), the heterologous polypeptide which mediates steviol glycoside transport may be obtained from or derived from a *Saccharomyces* (e.g., *S. cerevisiae, S. bayanus, S. pastorianus, S. carlsbergensis*), a *Candida* (e.g., *C. krusei, C. revkaufi, C. pulcherrima, C. tropicalis, C. utilis*) or a *Yarrowia* (e.g., *Y. lipolytica* (formerly classified as *Candida lipolytica*)).

For example, if the host cell is a *Yarrowia* (e.g., *Y. lipolytica* (formerly classified as *Candida lipolytica*)), the heterologous polypeptide which mediates steviol glycoside transport may be obtained from or derived from a *Saccharomyces* (e.g., *S. cerevisiae, S. bayanus, S. pastorianus, S. carlsbergensis*). a *Candida* (e.g., *C. krusei, C. revkaufi, C. pulcherrima, C. tropicalis, C. utilis*) or an *Issatchenkia* (eg. *I. orientalis*).

If the host cell is *Saccharomyces cerevisiae*, the heterologous polypeptide which mediates steviol glycoside transport may be obtained from or derived from *Yarrowia lipolytica* (formerly classified as *Candida lipolytica*)), *Candida krusei* or *Issatchenkia orientalis*.

If the host cell is *Yarrowia lipolytica*, the heterologous polypeptide which mediates steviol glycoside transport may be obtained from or derived from *Saccharomyces cerevisiae*, *Yarrowia lipolytica* (formerly classified as *Candida lipolytica*)) or *Candida krusei* or *Issatchenkia orientalis*.

If the host cell is *Candida krusei* or *Issatchenkia orientalis*, the heterologous polypeptide which mediates steviol glycoside transport may be obtained from or derived from *Saccharomyces cerevisiae* or *Yarrowia lipolytica*.

The term "derived from" also includes the terms "originated from," "obtained from," "obtainable from," "isolated from," and "created from," and generally indicates that one specified material find its origin in another specified material or has features that can be described with reference to the another specified material. As used herein, a substance (e.g., a nucleic acid molecule or polypeptide) "derived from" a microorganism may indicate that the substance is native to that microorganism or is a substance native to that microorganism, but may also indicate a substance that has been altered from a native version.

Thus, for example, a recombinant cell may express a polypeptide as defined herein not found within the native (non-recombinant) form of the cell. Alternatively, a recombinant cell may be modified so as to express a native gene encoding a polypeptide as defined herein to a greater degree than takes place within the native "non-recombinant" form of the cell.

Alternatively, a recombinant cell may be modified so as to express a native gene encoding a polypeptide as defined herein to a lesser degree than takes place within the native "non-recombinant" form of the cell.

In a cell of the invention, a polypeptide as defined herein may be overexpressed. Herein, "overexpressed", "overexpression" or the like implies that the recombinant host cell expresses more of the polypeptide than a corresponding cell which does not overexpress the polypeptide or, alternatively, that the polypeptide is expressed in a cell which would not typically express that protein. Alternatively, overexpression may be achieved by expressing a variant polypeptide having a higher specific activity.

A recombinant cell of the invention cell may be modified, preferably in its genome, to result in a deficiency in the production of a polypeptide as defined herein.

Such a cell may be from a parent host cell and be modified, preferably in its genome, if compared to the parent host cell to obtain a different genotype and/or a different phenotype if compared to the parent host cell from which it is derived.

Such a cell which has been modified, preferably in its genome, to result in a deficiency in the production of a polypeptide as defined herein, is a mutant host cell which has been modified, preferably in its genome, to result in a phenotypic feature wherein the cell: a) produces less of the product or produces substantially no product and/or b) produces a product having a decreased activity or decreased specific activity or a product having no activity or no specific activity and combinations of one or more of these possibilities as compared to the parent microbial host cell that has not been modified, when analyzed under the same conditions.

The term "recombinant" is synonymous with "genetically modified".

Such a recombinant host may be a full or partial knockout of a nucleic acid sequence encoding a polypeptide as described herein.

The invention thus concerns recombinant hosts overexpressing or deficient in a polypeptide identified as having steviol glycoside transport mediating activity: typically, the host is one which may be used for the production of steviol glycosides. The ability of a given recombinant host to produce a steviol glycoside may be a property of the host in non-recombinant form or may be a result of the introduction of one or more recombinant nucleic acid sequences (i.e. encoding enzymes leading to the production of a steviol glycoside).

For the purpose of this invention, a polypeptide having steviol glycoside transport mediating activity (i.e. a polypeptide which mediates steviol glycoside transport) is one which has an effect on transport of one or more steviol glycosides across a cell membrane. The effect may be direct, i.e. the polypeptide may be a transporter protein or comprise a functional transporter region. Alternatively, the effect may be indirect, i.e. the polypeptide is not a transporter protein, but its activity nevertheless has an effect on steviol glycoside transport.

Typically, the effect will be such that increasing the level of expression of the polypeptide increases the amount of transport of one or more steviol glycosides across the membrane of a cell (in comparison with a corresponding cell having a lower level of expression of the polypeptide). Conversely, decreasing the level of expression of the polypeptide may decrease the amount of transport of one or more steviol glycosides across the membrane of a cell (in comparison with a corresponding cell having a higher level of expression of the polypeptide).

Typically, a recombinant host of the invention is capable of producing a steviol glycoside. For example, a recombinant host of the invention may be capable of producing one or more of, for example but not limited to, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM. A recombinant host of the invention may be capable of producing one or more of the steviol glycosides set out in Ceunen and Geuns, Journal of Natural Products 76(6), 1201-1228, 2013.

Thus, a cell of the invention may be one in which the amount of total amount of steviol glycosides outside the cell as compared with inside the cell is greater or less than compared with a corresponding cell which either does not overexpress or does not have a reduced level of expression of a cell of the invention.

Alternatively, a cell of the invention may have the same total amount of steviol glycosides outside the cell as compared with inside the cell compared with a corresponding cell which either does not overexpress or does not have a reduced level of expression of a cell of the invention, but may have an altered distribution of steviol glycosides inside and outside the cell.

Thus, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebB, rebC, rebD, rebE or rebM.

Thus, a recombinant host of the invention may be one in which at least about 10%, at least about 20%, at least about 30%, at least about 40%, at least about 50% of the rebA produced by the cell is outside the cell.

Thus, a recombinant host of the invention may be one in which at least about 10%, at least about 20%, at least about 30%, at least about 40%, at least about 50% of the rebD produced by the cell is outside the cell.

Thus, a recombinant host of the invention may be one in which at least about 10%, at least about 20%, at least about 30%, at least about 40%, at least about 50% of the rebM produced by the cell is outside the cell.

A recombinant cell of the invention may be one in which no more than about 50%, no more than about 40%, no more than about 30%, no more than about 20%, no more than about 10% of the rebA produced by the cell is outside the cell.

A recombinant cell of the invention may be one in which no more than about 50%, no more than about 40%, no more than about 30%, no more than about 20%, no more than about 10% of the rebD produced by the cell is outside the cell.

A recombinant cell of the invention may be one in which no more than about 50%, no more than about 40%, no more than about 30%, no more than about 20%, no more than about 10% of the rebM produced by the cell is outside the cell.

A recombinant cell of the invention may be one where the average glycosylation number of the steviol glycosides is at least 3, at least 4, at least 5, at least 6 or more. The average glycosylation number may be increased or decreased in comparison with a corresponding cell not modified according to the invention. For example, average glycosylation may decrease when a polypeptide as described herein is overexpressed. For example, average glycosylation may increase (in particular in a cell itself) when expression of a polypeptide of the invention is reduced.

The average glycosylation may refer to that in the supernatant of a recombinant cell of the invention or to the average glycosylation in the broth (pellet+supernatant).

The invention thus provides a recombinant cell capable of producing a steviol glycoside either overexpressing or deficient in the expression of a polypeptide comprising the amino acid sequence set forth in SEQ ID NO: 29 or an amino acid sequence having at least about 50% sequence identity thereto. Such an amino acid sequence has an effect of steviol glycoside transport, i.e. is a mediator of steviol glycoside transport.

The polypeptide may also be defined as one comprising the following amino acid sequence (or an amino acid sequence having at least about 45% sequence identity thereto):

```
                                           (SEQ ID NO: 29)
MGKTEVTQESLECGSVTSSLGKKPFSIITLFTGRRIPPVPTEKPDSAEER

AGILSKLTWQWLSPLLKTGYLRNIEREDLYKVRERNSAAVIQQRLESNLE

KQYAKYHAKLLKKGLSEQEAHLKLQDSAKPLVLALNQTFFWKFWLAGLFA

LVKDLCGIASAMVSRVLIEYIQDRYLYRGTDREPKVGRGVGPSIGLFLLA

VGVTFFFNHMFYNVKMVGAQARAALVAVIYSKSTRLSAKGRAQYTTGKIT

NLAAIDAHRVDLSCESFHYITIFLPVVGCAIAVLVVNLKVAALVGIATMI

VLIFVVAGITIFSMKLRAIIVKLTDKRVTYIREALQSIRIIKYYGWEVPY

CDKIKKVRLDETRNYAKMGSIRGTAIGMFQALPILAGALSFITYAALGHG

TDPARMFSSLTLFNLLLPALAVLPQALQAAGDARVALRRIQRFLGAEEST

PTTVFDATLESTDDAVIVEDASFIWPEVVDDKSDKEKAKDAKKEEKDKKK

AEKKAKKAAKKAAKEIAVVVEEEVEHEKTEGSSESEKGTLKSTFKGFNNL

SFKIKRGEFVVVTGPIGSGKSSLLAAITGSMVLTGGSVRVSSTEWIGCLE

PWIQNATVRDNIVFGRKFDSEWYRTVVTACQLSQDLKIMTHGDNTMIGER
```

-continued

GITVSGGQKARINLARAIYGNPEILIMDDVLSAVDARVGAGIVDDCLRGL

AKNSTRILATHQLSVLPKADHVIFMDAEGQPHIGTYQELEADNEQFKALL

AAGSMSKEEVVAVDETEVVIEGDLEDDCDNKEEYEDAAETISILADATQE

LQKVTTTVSAFEENDNMMEEEERMRDAVGLHVYWQYFRQANPSRVKVMMF

IGMIFISMIVIAFLFVFTSVWLSFWTGDRFHASRNFYTGIYIMLGILLLL

AVAGYMIVNEINSAMAARNLHNHALDSVFAARTSFFDTTPQGRIINRFTR

DTDSLDNELAMRLTMLFFGVSAFFSNFLLTCVYVPYVTLVLVPVGFVFYV

SLGYYRKSAREVKRIDSIERSHMMSVFNESISGMPVIIMYKAQHRLMNKL

QATLDDMDSAYFLTAANQRWLSLRLDGLGSLVVLVATILVAVGVFDLTPS

NMGLIISAASFIPEVMSMVAQAVAELENCMNATERILYYKDNIPAEAARE

VDGTELDQRPNWPEQGAISFNNVSMKYRDGLPYVLKSLSVDFQGGHKVGI

CGRTGAGKSTILQTLYRIVELAEGSITIDGVDISTIGLHQLRSQLSIIPQ

EPVLFLGTIRSNLDPLEQYSDAELWGSLRRSGLLDEGETEGKFHLDQKVE

ADGSNFSLGERQLLTLARALLRNTKILVLDEATSNVDYKTDKLVQETISR

EFGHCTILCIAHRLRTIAKYDRILVLESGEINQYDTPWNLYNDKEGIFRG

MCDTSGLNEVDFNK.

A polypeptide, typically having steviol glycoside transport mediating activity, may comprise an amino acid sequence having at least about 50%, at least about 55%, at least about 60%, at least about 65%, at least about 70%, at least about 75%, at least about 80%, at least about 85%, at least about, 86%, at least about 87%, at least about 88%, at least about 89%, at least about 90%, at least about 91%, at least about 92%, at least about 93%, at least about 94%, at least about 95%, at least about 96%, at least about 97%, at least about 98% or at least about 99% sequence identity to SEQ ID NO: 29.

A polypeptide, typically having steviol glycoside transport mediating activity, encoded by a recombinant nucleic acid present in a recombinant host of the invention may comprise an amino acid sequence which is a fragment of an amino acid sequence described herein, for example a truncated version of such an amino acid sequence.

That is to say, the invention also a recombinant host overexpressing a biologically active fragment of a polypeptide having steviol glycoside transport mediating activity as described herein.

Biologically active fragments of a polypeptide of the invention include polypeptides comprising amino acid sequences sufficiently identical to or derived from the amino acid sequence of SEQ ID NO: 29 which include fewer amino acids than the full-length polypeptide as given in SEQ ID NO: 29, but which exhibit at least one biological activity of the corresponding full-length polypeptide.

Typically, biologically active fragments comprise a domain or motif with at least one activity of the polypeptide of the invention. A biologically active fragment of a polypeptide of the invention can be a polypeptide which is, for example, about 10, about 25, about 50, about 100 or more amino acids in length or at least about 100 amino acids, at least 150, 200, 250, 300, 350, 400, 600, 1000 amino acids in length, or of a length up to the total number of amino acids of the polypeptide of the invention. Moreover, other biologically active portions, in which other regions of the polypeptide are deleted, can be prepared by recombinant techniques and evaluated for one or more of the biological activities of the native form of a polypeptide of the invention. The invention also features nucleic acid fragments which encode the above biologically active fragments of the polypeptide of the invention.

A recombinant host of the invention may overexpress or be deficient in such a polypeptide.

A recombinant host of the invention may comprise recombinant nucleic acid sequences encoding more than one such polypeptide, for example two, three, four or more such polypeptides. The polypeptides thus encoded may be the same or different.

A recombinant cell of the invention may be modified so as to reduce the expression level of more than one such polypeptide, for example two, three, four or more such polypeptides.

An overexpressed polypeptide encoded by a recombinant nucleic acid present in a recombinant host may be one which is obtainable from or derived from or found in an organism of the genus Yarrowia, for example one which is obtainable from or derived from or found in a Yarrowia lipolytica.

As used herein, the term "polypeptide" refers to a molecule comprising amino acid residues linked by peptide bonds and containing more than five amino acid residues. The amino acids are identified by either the single-letter or three-letter designations. The term "protein" as used herein is synonymous with the term "polypeptide" and may also refer to two or more polypeptides. Thus, the terms "protein", "peptide" and "polypeptide" can be used interchangeably. Polypeptides may optionally be modified (e.g., glycosylated, phosphorylated, acylated, farnesylated, prenylated, sulfonated, and the like) to add functionality. Polypeptides exhibiting activity may be referred to as enzymes. It will be understood that, as a result of the degeneracy of the genetic code, a multitude of nucleotide sequences encoding a given polypeptide may be produced.

A polypeptide encoded by a recombinant nucleic acid for use in a recombinant host of the invention may comprise a signal peptide and/or a propeptide sequence. In the event that a polypeptide of the invention comprises a signal peptide and/or a propeptide, sequence identity may be calculated over the mature polypeptide sequence.

A recombinant nucleic acid sequence for use in a recombinant host of the invention may be provided in the form of a nucleic acid construct. The term "nucleic acid construct" refers to a nucleic acid molecule, either single- or double-stranded, which is isolated from a naturally occurring gene or which has been modified to contain segments of nucleic acid which are combined and juxtaposed in a manner which would not otherwise exist in nature. The term nucleic acid construct is synonymous with the term "expression cassette" when the nucleic acid construct contains all the control sequences required for expression of a coding sequence, wherein said control sequences are operably linked to said coding sequence.

A recombinant nucleic acid sequence for use in a recombinant host of the invention may be provided in the form of an expression vector, wherein the polynucleotide sequence is operably linked to at least one control sequence for the expression of the polynucleotide sequence in a recombinant host cell.

The term "operably linked" as used herein refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

An expression vector comprises a polynucleotide coding for a polypeptide as described herein, operably linked to the appropriate control sequences (such as a promoter, and transcriptional and translational stop signals) for expression and/or translation in vitro, or in the host cell of the polynucleotide.

The expression vector may be any vector (e.g., a plasmid or virus), which can be conveniently subjected to recombinant DNA procedures and can bring about the expression of the polynucleotide. The choice of the vector will typically depend on the compatibility of the vector with the cell into which the vector is to be introduced. The vectors may be linear or closed circular plasmids. The vector may be an autonomously replicating vector, i.e., a vector, which exists as an extra-chromosomal entity, the replication of which is independent of chromosomal replication, e.g., a plasmid, an extra-chromosomal element, a mini-chromosome, or an artificial chromosome.

Alternatively, the vector may be one which, when introduced into the host cell, is integrated into the genome and replicated together with the chromosome(s) into which it has been integrated. The integrative cloning vector may integrate at random or at a predetermined target locus in the chromosomes of the host cell. A vector may comprise one or more selectable markers, which permit easy selection of transformed cells.

A recombinant host capable of producing a steviol glycoside which has been modified, preferably in its genome, to result in a deficiency in the production of a polypeptide described herein may be generated according to methods well known to those skilled in the art. A sequence encoding a polypeptide as described herein may be modified such that less or no expression of the polypeptide takes place. A sequence encoding a polypeptide as described herein may be partially or entirely deleted, for example.

A recombinant host of the invention may comprise any polypeptide as described herein. A recombinant host of the invention may overexpress or be deficient in any polypeptide described herein. Typically, a recombinant host of the invention is capable of producing a steviol glycoside. For example, a recombinant host of the invention may be capable of producing one or more of, for example, steviol-13-monoside, steviol-19-monoside, 13-[(β-D-Glucopyranosyl)oxy)kaur-16-en-18-oic acid 2-O-β-D-glucopyranosyl-β-D-glucopyranosyl ester, rubusoside, stevioside, steviol-19-diside, steviolbioside, rebA, rebE, rebD or rebM.

A recombinant host of the invention may comprise one or more recombinant nucleic acid sequences encoding one or more polypeptides having UDP-glycosyltransferase (UGT) activity.

For the purposes of this invention, a polypeptide having UGT activity is one which has glycosyltransferase activity (EC 2.4), i.e. that can act as a catalyst for the transfer of a monosaccharide unit from an activated nucleotide sugar (also known as the "glycosyl donor") to a glycosyl acceptor molecule, usually an alcohol. The glycosyl donor for a UGT is typically the nucleotide sugar uridine diphosphate glucose (uracil-diphosphate glucose, UDP-glucose).

Figure 21:
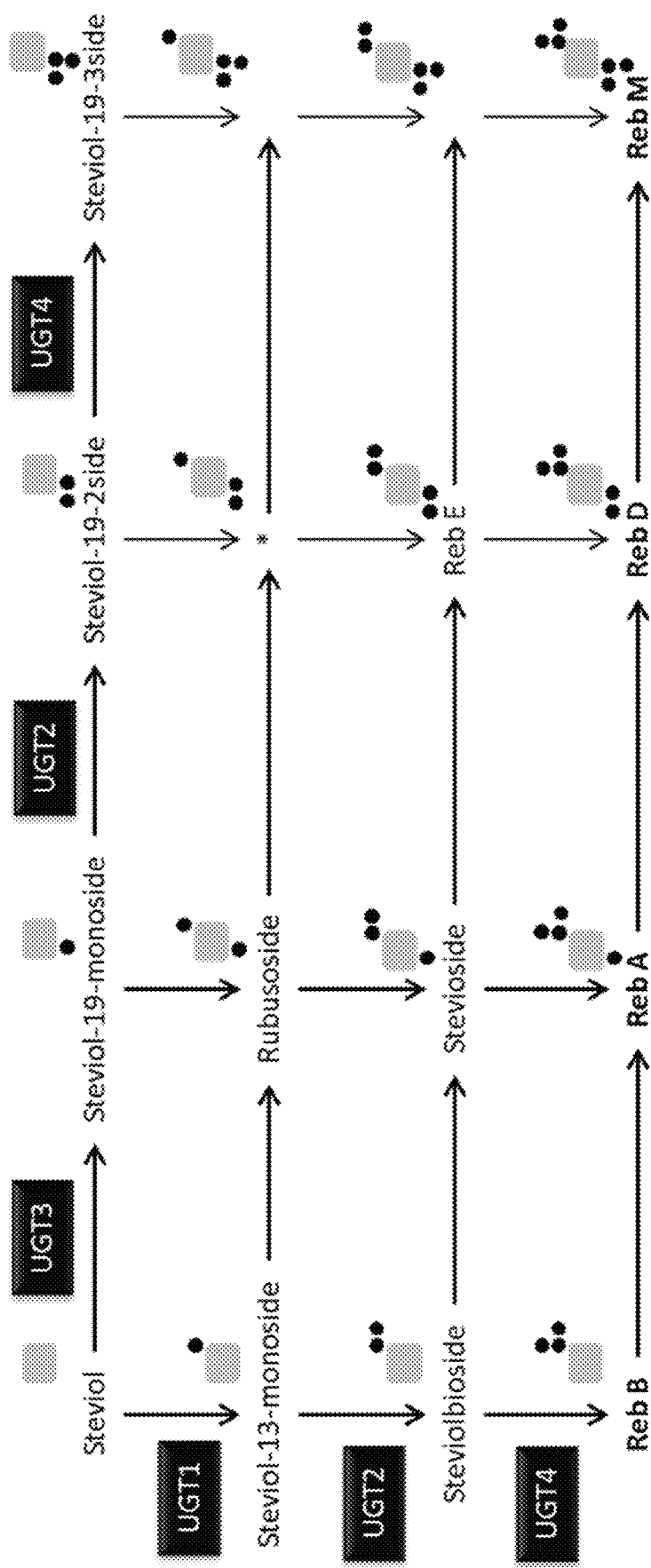
FIG. 21 sets out a schematic diagram of the potential pathways leading to biosynthesis of steviol glycosides. The compound shown with an asterisk is 13-[(β-D-Glucopyranosyl)oxy]kaur-16-en-18-oic acid 2-O-β-D-glucopyranosyl-β-D-glucopyranosyl ester.

Such additional UGTs may be selected so as to produce a desired steviol glycoside. Schematic diagrams of steviol glycoside formation are set out in Humphrey et al., Plant Molecular Biology (2006) 61: 47-62 and Mohamed et al., J. Plant Physiology 168 (2011) 1136-1141. In addition, FIG. 21 sets out a schematic diagram of steviol glycoside formation.

A recombinant host of the invention may thus comprise one or more recombinant nucleic acid sequences encoding one or more of:

(i) a polypeptide having UGT74G1 activity;
(ii) a polypeptide having UGT2 activity;
(iii) a polypeptide having UGT85C2 activity; and
(iv) a polypeptide having UGT76G1 activity.

A recombinant yeast suitable for use in the invention may comprise a nucleotide sequence encoding a polypeptide capable of catalyzing the addition of a C-13-glucose to steviol. That is to say, a recombinant yeast suitable for use in a method of the invention may comprise a UGT which is capable of catalyzing a reaction in which steviol is converted to steviolmonoside.

Such a recombinant yeast suitable for use in a method of the invention may comprise a nucleotide sequence encoding a polypeptide having the activity shown by UDP-glycosyltransferase (UGT) UGT85C2, whereby the nucleotide sequence upon transformation of the yeast confers on that yeast the ability to convert steviol to steviolmonoside.

UGT85C2 activity is transfer of a glucose unit to the 13-OH of steviol.
Thus, a suitable UGT85C2 may function as a uridine 5'-diphospho glucosyl: steviol 13-OH transferase, and a uridine 5'-diphospho glucosyl: steviol-19-0-glucoside 13-OH transferase. A functional UGT85C2 polypeptides may also catalyze glucosyl transferase reactions that utilize steviol glycoside substrates other than steviol and steviol-19-O-glucoside. Such sequences may be referred to as UGT1 sequences herein.

A recombinant yeast suitable for use in the invention may comprise a nucleotide sequence encoding a polypeptide which has UGT2 activity.

A polypeptide having UGT2 activity is one which functions as a uridine 5'-diphospho glucosyl: steviol-13-O-glucoside transferase (also referred to as a steviol-13-monoglucoside 1,2-glucosylase), transferring a glucose moiety to the C-2' of the 13-O-glucose of the acceptor molecule, steviol-13-O-glucoside. Typically, a suitable UGT2 polypeptide also functions as a uridine 5'-diphospho glucosyl: rubusoside transferase transferring a glucose moiety to the C-2' of the 13-O-glucose of the acceptor molecule, rubusoside.

A polypeptide having UGT2 activity may also catalyze reactions that utilize steviol glycoside substrates other than steviol-13-0-glucoside and rubusoside, e.g., functional UGT2 polypeptides may utilize stevioside as a substrate, transferring a glucose moiety to the C-2' of the 19-O-glucose residue to produce rebaudioside E. A functional UGT2 polypeptides may also utilize rebaudioside A as a substrate, transferring a glucose moiety to the C-2' of the 19-O-glucose residue to produce rebaudioside D. However, a functional UGT2 polypeptide may be one which does not transfer a glucose moiety to steviol compounds having a 1,3-bound glucose at the C-13 position, i.e., transfer of a glucose moiety to steviol 1,3-bioside and 1,3-stevioside typically does not occur.

A polypeptide having UGT2 activity may also transfer sugar moieties from donors other than uridine diphosphate glucose. For example, a polypeptide having UGT2 activity act as a uridine 5'-diphospho D-xylosyl: steviol-13-O-glucoside transferase, transferring a xylose moiety to the C-2' of the 13-O-glucose of the acceptor molecule, steviol-13-O-glucoside. As another example, a polypeptide having UGT2 activity may act as a uridine 5'-diphospho L-rhamnosyl:

steviol-13-O-glucoside transferase, transferring a rhamnose moiety to the C-2' of the 13-O-glucose of the acceptor molecule, steviol.

A recombinant yeast suitable for use in the method of the invention may comprise a nucleotide sequence encoding a polypeptide having UGT activity may comprise a nucleotide sequence encoding a polypeptide capable of catalyzing the addition of a C-19-glucose to steviolbioside. That is to say, a recombinant yeast of the invention may comprise a UGT which is capable of catalyzing a reaction in which steviol-bioside is converted to stevioside. Accordingly, such a recombinant yeast may be capable of converting steviolbioside to stevioside. Expression of such a nucleotide sequence may confer on the recombinant yeast the ability to produce at least stevioside.

A recombinant yeast suitable for use in a method of the invention may thus also comprise a nucleotide sequence encoding a polypeptide having the activity shown by UDP-glycosyltransferase (UGT) UGT74G1, whereby the nucleotide sequence upon transformation of the yeast confers on the cell the ability to convert steviolbioside to stevioside.

Suitable UGT74G1 polypeptides may be capable of transferring a glucose unit to the 13-OH and/or the 19-COOH of steviol. A suitable UGT74G1 polypeptide may function as a uridine 5'-diphospho glucosyl: steviol 19-COOH transferase and/or a uridine 5'-diphospho glucosyl: steviol-13-O-glucoside 19-COOH transferase. Functional UGT74G1 polypeptides also may catalyze glycosyl transferase reactions that utilize steviol glycoside substrates other than steviol and steviol-13-O-glucoside, or that transfer sugar moieties from donors other than uridine diphosphate glucose. Such sequences may be referred to herein as UGT3 sequences.

A recombinant yeast suitable for use in a method the invention may comprise a nucleotide sequence encoding a polypeptide capable of catalyzing glucosylation of the C-3' of the glucose at the C-13 position of stevioside. That is to say, a recombinant yeast suitable for use in a method of the invention may comprise a UGT which is capable of catalyzing a reaction in which stevioside is converted to rebaudioside A. Accordingly, such a recombinant yeast may be capable of converting stevioside to rebaudioside A. Expression of such a nucleotide sequence may confer on the yeast the ability to produce at least rebaudioside A.

A recombinant yeast suitable for use in a method of the invention may thus also comprise a nucleotide sequence encoding a polypeptide having the activity shown by UDP-glycosyltransferase (UGT) UGT76G1, whereby the nucleotide sequence upon transformation of a yeast confers on that yeast the ability to convert stevioside to rebaudioside A.

A suitable UGT76G1 adds a glucose moiety to the C-3' of the C-13-O-glucose of the acceptor molecule, a steviol 1,2 glycoside. Thus, UGT76G1 functions, for example, as a uridine 5'-diphospho glucosyl: steviol 13-0-1,2 glucoside C-3 ' glucosyl transferase and a uridine 5'-diphospho glucosyl: steviol-19-0-glucose, 13-0-1,2 bioside C-3' glucosyl transferase. Functional UGT76G1 polypeptides may also catalyze glucosyl transferase reactions that utilize steviol glycoside substrates that contain sugars other than glucose, e.g., steviol rhamnosides and steviol xylosides. Such sequences may be referred to herein as UGT4 sequences. A UGT4 may alternatively or in addition be capable of converting RebD to RebM.

A recombinant yeast suitable for use in a method of the invention typically comprises nucleotide sequences encoding at least one polypeptide having UGT1 activity, at least one polypeptide having UGT2 activity, least one polypeptide having UGT3 activity and at least one polypeptide having UGT4 activity. One or more of these nucleic acid sequences may be recombinant. A given nucleic acid may encode a polypeptide having one or more of the above activities. For example, a nucleic acid encode for a polypeptide which has two, three or four of the activities set out above. Preferably, a recombinant yeast for use in the method of the invention comprises UGT1, UGT2 and UGT3 and UGT4 activity. Suitable UGT1, UGT2, UGT3 and UGT4 sequences are described in Table 1 of WO2015/007748.

A recombinant host of the invention may comprise two or more nucleic acid sequences encoding a polypeptide having any one UGT activity, for example UGT1, 2, 3 or 4, activity. Where a recombinant host of the invention comprises two or more nucleic acid sequence encoding a polypeptide having any one UGT activity, those nucleic acid sequences may be the same or different and/or may encode the same or different polypeptides. In particular, a recombinant host of the invention may comprise a nucleic acid sequence encoding a two different UGT2 polypeptides.

A recombinant host according to the invention may comprise one or more recombinant nucleotide sequence(s) encoding one of more of:

a polypeptide having ent-copalyl pyrophosphate synthase activity;
a polypeptide having ent-Kaurene synthase activity;
a polypeptide having ent-Kaurene oxidase activity; and
a polypeptide having kaurenoic acid 13-hydroxylase activity.

For the purposes of this invention, a polypeptide having ent-copalyl pyrophosphate synthase (EC 5.5.1.13) is capable of catalyzing the chemical reaction:

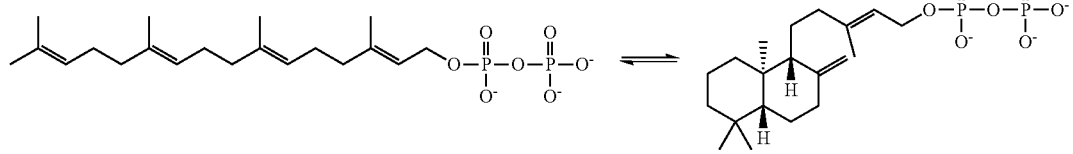

This enzyme has one substrate, geranylgeranyl pyrophosphate, and one product, ent-copalyl pyrophosphate. This enzyme participates in gibberellin biosynthesis. This enzyme belongs to the family of isomerase, specifically the class of intramolecular lyases. The systematic name of this enzyme class is ent-copalyl-diphosphate lyase (decyclizing). Other names in common use include having ent-copalyl pyrophosphate synthase, ent-kaurene synthase A, and ent-kaurene synthetase A.

Suitable nucleic acid sequences encoding an ent-copalyl pyrophosphate synthase may for instance comprise a sequence as set out in SEQ ID. NO: 1, 3, 5, 7, 17, 19, 59, 61, 141, 142, 151, 152, 153, 154, 159, 160, 182 or 184 of WO2015/007748.

For the purposes of this invention, a polypeptide having ent-kaurene synthase activity (EC 4.2.3.19) is a polypeptide that is capable of catalyzing the chemical reaction:

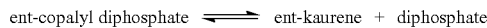

ent-copalyl diphosphate ⇌ ent-kaurene + diphosphate

Hence, this enzyme has one substrate, ent-copalyl diphosphate, and two products, ent-kaurene and diphosphate.

This enzyme belongs to the family of lyases, specifically those carbon-oxygen lyases acting on phosphates. The systematic name of this enzyme class is ent-copalyl-diphosphate diphosphate-lyase (cyclizing, ent-kaurene-forming). Other names in common use include ent-kaurene synthase B, ent-kaurene synthetase B, ent-copalyl-diphosphate diphosphate-lyase, and (cyclizing). This enzyme participates in diterpenoid biosynthesis.

Suitable nucleic acid sequences encoding an ent-Kaurene synthase may for instance comprise a sequence as set out in SEQ ID. NO: 9, 11, 13, 15, 17, 19, 63, 65, 143, 144, 155, 156, 157, 158, 159, 160, 183 or 184 of WO2015/007748.

ent-copalyl diphosphate synthases may also have a distinct ent-kaurene synthase activity associated with the same protein molecule. The reaction catalyzed by ent-kaurene synthase is the next step in the biosynthetic pathway to gibberellins. The two types of enzymic activity are distinct, and site-directed mutagenesis to suppress the ent-kaurene synthase activity of the protein leads to build up of ent-copalyl pyrophosphate.

Accordingly, a single nucleotide sequence used in a recombinant host of the invention may encode a polypeptide having ent-copalyl pyrophosphate synthase activity and ent-kaurene synthase activity. Alternatively, the two activities may be encoded two distinct, separate nucleotide sequences.

For the purposes of this invention, a polypeptide having ent-kaurene oxidase activity (EC 1.14.13.78) is a polypeptide which is capable of catalysing three successive oxidations of the 4-methyl group of ent-kaurene to give kaurenoic acid. Such activity typically requires the presence of a cytochrome P450.

Suitable nucleic acid sequences encoding an ent-Kaurene oxidase may for instance comprise a sequence as set out in SEQ ID. NO: 21, 23, 25, 67, 85, 145, 161, 162, 163, 180 or 186 of WO2015/007748.

For the purposes of the invention, a polypeptide having kaurenoic acid 13-hydroxylase activity (EC 1.14.13) is one which is capable of catalyzing the formation of steviol (ent-kaur-16-en-13-ol-19-oic acid) using NADPH and $O_2$. Such activity may also be referred to as ent-ka 13-hydroxylase activity.

Suitable nucleic acid sequences encoding a kaurenoic acid 13-hydroxylase may for instance comprise a sequence as set out in SEQ ID. NO: 27, 29, 31, 33, 69, 89, 91, 93, 95, 97, 146, 164, 165, 166, 167 or 185 of WO2015/007748.

A recombinant host of the invention may comprise a recombinant nucleic acid sequence encoding a polypeptide having NADPH-cytochrome p450 reductase activity. That is to say, a recombinant host of the invention may be capable of expressing a nucleotide sequence encoding a polypeptide having NADPH-cytochrome p450 reductase activity. For the purposes of the invention, a polypeptide having NADPH-Cytochrome P450 reductase activity (EC 1.6.2.4; also known as NADPH:ferrihemoprotein oxidoreductase, NADPH:hemoprotein oxidoreductase, NADPH:P450 oxidoreductase, P450 reductase, POR, CPR, CYPOR) is typically one which is a membrane-bound enzyme allowing electron transfer to cytochrome P450 in the microsome of the eukaryotic cell from a FAD- and FMN-containing enzyme NADPH:cytochrome P450 reductase (POR; EC 1.6.2.4).

In a recombinant host of the invention, the ability of the host to produce geranylgeranyl diphosphate (GGPP) may be upregulated. Upregulated in the context of this invention implies that the recombinant host produces more GGPP than an equivalent non-recombinant host.

Accordingly, a recombinant host of the invention may comprise one or more nucleotide sequence(s) encoding hydroxymethylglutaryl-CoA reductase, farnesyl-pyrophosphate synthetase and geranylgeranyl diphosphate synthase, whereby the nucleotide sequence(s) upon transformation of a host confer(s) on that host the ability to produce elevated levels of GGPP. Thus, a recombinant host according to the invention may comprise one or more recombinant nucleic acid sequence(s) encoding one or more of hydroxymethylglutaryl-CoA reductase, farnesyl-pyrophosphate synthetase and geranylgeranyl diphosphate synthase.

Accordingly, a recombinant host of the invention may comprise nucleic acid sequences encoding one or more of:
  a polypeptide having hydroxymethylglutaryl-CoA reductase activity;
  a polypeptide having farnesyl-pyrophosphate synthetase activity; and A recombinant host of the invention may be, for example, an multicellular organism or a cell thereof or a unicellular organism. A host of the invention may be a prokaryotic, archaebacterial or eukaryotic host cell.

A prokaryotic host cell may, but is not limited to, a bacterial host cell. An eukaryotic host cell may be, but is not limited to, a yeast, a fungus, an amoeba, an algae, an animal, an insect host cell.

An eukaryotic host cell may be a fungal host cell. "Fungi" include all species of the subdivision Eumycotina (Alexopoulos, C. J., 1962, In: Introductory Mycology, John Wiley & Sons, Inc., New York). The term fungus thus includes among others filamentous fungi and yeast.

"Filamentous fungi" are herein defined as eukaryotic microorganisms that include all filamentous forms of the subdivision Eumycotina and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolismis obligatory aerobic. Filamentous fungal strains include, but are not limited to, strains of *Acremonium, Aspergillus, Agaricus, Aureobasidium, Cryptococcus, Corynascus, Chrysosporium, Filibasidium, Fusarium, Humicola, Magnaporthe, Monascus, Mucor, Myceliophthora, Mortierella, Neocallimastix, Neurospora, Paecilomyces, Penicillium, Piromyces, Phanerochaete Podospora, Pycnoporus, Rhizopus, Schizophyllum, Sordaria, Talaromyces, Rasmsonia, Thermoascus, Thielavia, Tolypocladium, Trametes* and *Trichoderma*. Preferred filamentous fungal strains that may serve as host cells belong to the species *Aspergillus niger, Aspergillus oryzae, Aspergillus fumigatus, Penicillium chrysogenum, Penicillium citrinum, Acremonium chrysogenum, Trichoderma reesei, Rasamsonia emersonii* (formerly known as *Talaromyces emersonii*), *Aspergillus sojae, Chrysosporium lucknowense, Myceliophtora thermophyla*. Reference host cells for the comparison of fermentation characteristics of transformed and untransformed cells, include e.g. *Aspergillus niger* CBS120.49, CBS 513.88, *Aspergillus oryzae* ATCC16868, ATCC 20423, IFO 4177, ATCC 1011, ATCC 9576, ATCC14488-14491, ATCC 11601, ATCC12892, *Aspergillus fumigatus* AF293 (CBS101355), *P. chrysogenum* CBS 455.95, *Penicillium citrinum* ATCC 38065, *Penicillium chrysogenum* P2, *Acremonium chrysogenum* ATCC 36225, ATCC 48272, *Trichoderma reesei* ATCC 26921, ATCC 56765, ATCC 26921, *Aspergillus sojae* ATCC11906, *Chrysosporium lucknowense* ATCC44006 and derivatives of all of these strains. Particularly preferred as filamentous fungal host cell are *Aspergillus niger* CBS 513.88 and derivatives thereof.

An eukaryotic host cell may be a yeast cell. Preferred yeast host cells may be selected from the genera: *Saccharomyces* (e.g., *S. cerevisiae, S. bayanus, S. pastorianus, S. carlsbergensis*), Brettanomyces, *Kluyveromyces*, Candida (e.g., *C. krusei, C. revkaufi, C. pulcherrima, C. tropicalis, C. utilis*), Issatchenkia (eg. *I. orientalis*) Pichia (e.g., *P. pastoris* and *P. kudriavzevii*), Schizosaccharomyces, Hansenula, Kloeckera, Pachysolen, Schwanniomyces, Trichosporon, Yarrowia (e.g., *Y. lipolytica* (formerly classified as *Candida lipolytica*)), Yamadazyma.

Prokaryotic host cells may be bacterial host cells. Bacterial host cell may be Gram negative or Gram positive bacteria. Examples of bacteria include, but are not limited to, bacteria belonging to the genus *Bacillus* (e.g., *B. subtilis, B. amyloliquefaciens, B. licheniformis, B. puntis, B. megaterium, B. halodurans, B. pumilus,*), Acinetobacter, Nocardia, Xanthobacter, Escherichia (e.g., *E. coli* (e.g., strains DH 1 OB, Stbl2, DH5-alpha, DB3, DB3.1), DB4, DB5, JDP682 and ccdA-over (e.g., U.S. application Ser. No. 09/518, 188))), Streptomyces, Erwinia, Klebsiella, Serratia (e.g., *S. marcessans*), Pseudomonas (e.g., *P. aeruginosa*), Salmonella (e.g., *S. typhimurium, S. typhi*). Bacteria also include, but are not limited to, photosynthetic bacteria (e.g., green non-sulfur bacteria (e.g., Choroflexus bacteria (e.g., *C. aurantiacus*), Chloronema (e.g., *C. gigateum*)), green sulfur bacteria (e.g., Chlorobium bacteria (e.g., *C. limicola*), Pelodictyon (e.g., *P. luteolum*), purple sulfur bacteria (e.g., Chromatium (e.g., *C. okenii*)), and purple non-sulfur bacteria (e.g., Rhodospirillum (e.g., *R. rubrum*), Rhodobacter (e.g. *R. sphaeroides, R. capsulatus*), and Rhodomicrobium bacteria (e.g., *R. vanellii*)).

Host Cells may be host cells from non-microbial organisms. Examples of such cells, include, but are not limited to, insect cells (e.g., *Drosophila* (e.g., *D. melanogaster*), Spodoptera (e.g., *S. frugiperda* Sf9 or Sf21 cells) and *Trichoplusa* (e.g., High-Five cells); nematode cells (e.g., *C. elegans* cells); avian cells; amphibian cells (e.g., *Xenopus laevis* cells); reptilian cells; and mammalian cells (e.g., NIH3T3, 293, CHO, COS, VERO, C127, BHK, Per-C6, Bowes melanoma and HeLa cells).

A recombinant host according to the present invention may be able to grow on any suitable carbon source known in the art and convert it to a steviol glycoside. The recombinant host may be able to convert directly plant biomass, celluloses, hemicelluloses, pectines, rhamnose, galactose, fucose, maltose, maltodextrines, ribose, ribulose, or starch, starch derivatives, sucrose, lactose and glycerol. Hence, a preferred host expresses enzymes such as cellulases (endocellulases and exocellulases) and hemicellulases (e.g. endo- and exo-xylanases, arabinases) necessary for the conversion of cellulose into glucose monomers and hemicellulose into xylose and arabinose monomers, pectinases able to convert pectines into glucuronic acid and galacturonic acid or amylases to convert starch into glucose monomers. Preferably, the host is able to convert a carbon source selected from the group consisting of glucose, xylose, arabinose, sucrose, lactose and glycerol. The host cell may for instance be a eukaryotic host cell as described in WO03/062430, WO06/009434, EP1499708B1, WO2006096130 or WO04/099381.

Thus, in a further aspect, the invention also provides a process for the preparation of a steviol glycoside which comprises fermenting a recombinant host of the invention which is capable of producing at least one steviol glycoside in a suitable fermentation medium, and optionally recovering the steviol glycoside.

The fermentation medium used in the process for the production of a steviol glycoside may be any suitable fermentation medium which allows growth of a particular eukaryotic host cell. The essential elements of the fermentation medium are known to the person skilled in the art and may be adapted to the host cell selected.

Preferably, the fermentation medium comprises a carbon source selected from the group consisting of plant biomass, celluloses, hemicelluloses, pectines, rhamnose, galactose, fucose, fructose, maltose, maltodextrines, ribose, ribulose, or starch, starch derivatives, sucrose, lactose, fatty acids, triglycerides and glycerol. Preferably, the fermentation medium also comprises a nitrogen source such as ureum, or an ammonium salt such as ammonium sulphate, ammonium chloride, ammoniumnitrate or ammonium phosphate.

The fermentation process according to the present invention may be carried out in batch, fed-batch or continuous mode. A separate hydrolysis and fermentation (SHF) process or a simultaneous saccharification and fermentation (SSF) process may also be applied. A combination of these fermentation process modes may also be possible for optimal productivity. A SSF process may be particularly attractive if starch, cellulose, hemicelluose or pectin is used as a carbon source in the fermentation process, where it may be necessary to add hydrolytic enzymes, such as cellulases, hemicellulases or pectinases to hydrolyse the substrate.

The recombinant host used in the process for the preparation of a steviol glycoside may be any suitable recombinant host as defined herein above. It may be advantageous to use a recombinant eukaryotic recombinant host according to the invention in the process since most eukaryotic cells do not require sterile conditions for propagation and are insensitive to bacteriophage infections. In addition, eukaryotic host cells may be grown at low pH to prevent bacterial contamination.

The recombinant host according to the present invention may be a facultative anaerobic microorganism. A facultative anaerobic recombinant host can be propagated aerobically to a high cell concentration. This anaerobic phase can then be carried out at high cell density which reduces the fermentation volume required substantially, and may minimize the risk of contamination with aerobic microorganisms.

The fermentation process for the production of a steviol glycoside according to the present invention may be an aerobic or an anaerobic fermentation process.

An anaerobic fermentation process may be herein defined as a fermentation process run in the absence of oxygen or in which substantially no oxygen is consumed, preferably less than 5, 2.5 or 1 mmol/L/h, and wherein organic molecules serve as both electron donor and electron acceptors. The fermentation process according to the present invention may also first be run under aerobic conditions and subsequently under anaerobic conditions.

The fermentation process may also be run under oxygen-limited, or micro-aerobical, conditions. Alternatively, the fermentation process may first be run under aerobic conditions and subsequently under oxygen-limited conditions. An oxygen-limited fermentation process is a process in which the oxygen consumption is limited by the oxygen transfer from the gas to the liquid. The degree of oxygen limitation is determined by the amount and composition of the ingoing gasflow as well as the actual mixing/mass transfer properties of the fermentation equipment used.

The production of a steviol glycoside in the process according to the present invention may occur during the growth phase of the host cell, during the stationary (steady state) phase or during both phases. It may be possible to run the fermentation process at different temperatures.

The process for the production of a steviol glycoside may be run at a temperature which is optimal for the recombinant host. The optimum growth temperature may differ for each transformed recombinant host and is known to the person skilled in the art. The optimum temperature might be higher than optimal for wild type organisms to grow the organism efficiently under non-sterile conditions under minimal infection sensitivity and lowest cooling cost. Alternatively, the process may be carried out at a temperature which is not optimal for growth of the recombinant host.

The process for the production of a steviol glycoside according to the present invention may be carried out at any suitable pH value. If the recombinant host is a yeast, the pH in the fermentation medium preferably has a value of below 6, preferably below 5.5, preferably below 5, preferably below 4.5, preferably below 4, preferably below pH 3.5 or below pH 3.0, or below pH 2.5, preferably above pH 2. An advantage of carrying out the fermentation at these low pH values is that growth of contaminant bacteria in the fermentation medium may be prevented.

Such a process may be carried out on an industrial scale. The product of such a process is one or more steviol glycosides.

Recovery of steivol glycoside(s) from the fermentation medium may be performed by known methods in the art, for instance by distillation, vacuum extraction, solvent extraction, or evaporation.

In the process for the production of a steviol glycoside according to the invention, it may be possible to achieve a concentration of above 5 mg/l fermentation broth, preferably above 10 mg/l, preferably above 20 mg/l, preferably above 30 mg/l fermentation broth, preferably above 40 mg/l, more preferably above 50 mg/l, preferably above 60 mg/l, preferably above 70, preferably above 80 mg/l, preferably above 100 mg/l, preferably above 1 g/l, preferably above 5 g/l, preferably above 10 g/l, for example at least about 15 g/L, such as at least about 20 g/l.

The invention further provides a fermentation broth comprising a steviol glycoside obtainable by the process of the invention for the preparation of a steivol glycoside.

In the event that one or more steviol glycosides is expressed within a recombinant host of the invention, such cells may need to be treated so as to release them. Preferentially, at least one steviol glycoside, for example rebA or rebM, is produced extracellularly The invention also provides a steviol glycoside obtained by a process according to the invention for the preparation of a steviol glycoside or obtainable from a fermentation broth of the invention. Such a steviol glycoside may be a non-naturally occurring steviol glycoside, that is to say one which is not produced in plants.

Also provided is a composition obtainable by a process of the invention (which typically comprises one or more steviol glycosides), Also provided is a composition comprising two or more steviol glycosides obtainable by a process of the invention for the preparation of a steviol glycoside or obtainable from a fermentation broth of the invention. In such a composition, one or more of the steviol glycosides may be a non-naturally occurring steviol glycoside, that is to say one which is not produced in plants. These are all compositions of the invention.

A composition of the invention may be used in any application known for such compounds. In particular, such a composition may for instance be used as a sweetener, for example in a food or a beverage. According to the invention therefore, there is provided a foodstuff, feed or beverage which comprises a composition of the invention.

For example a composition of the invention may be formulated in soft drinks, as a tabletop sweetener, chewing gum, dairy product such as yoghurt (eg. plain yoghurt), cake, cereal or cereal-based food, nutraceutical, pharmaceutical, edible gel, confectionery product, cosmetic, toothpastes or other oral cavity composition, etc. In addition, a composition of the invention can be used as a sweetener not only for drinks, foodstuffs, and other products dedicated for human consumption, but also in animal feed and fodder with improved characteristics.

Accordingly, the invention provides, inter alia, a foodstuff, feed or beverage which comprises a composition of the invention.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

A composition of the invention can be used in dry or liquid forms. It can be added before or after heat treatment of food products. The amount of the sweetener depends on the purpose of usage. It can be added alone or in the combination with other compounds.

A composition of the invention may be blended with one or more further non-caloric or caloric sweeteners. Such blending may be used to improve flavour or temporal profile or stability. A wide range of both non-caloric and caloric sweeteners may be suitable for blending with a composition of the invention. For example, non-caloric sweeteners such as mogroside, monatin, aspartame, acesulfame salts, cyclamate, sucralose, saccharin salts or erythritol. Caloric sweeteners suitable for blending with a steviol glycoside or a composition of the invention include sugar alcohols and carbohydrates such as sucrose, glucose, fructose and HFCS. Sweet tasting amino acids such as glycine, alanine or serine may also be used.

A composition of the invention can be used in the combination with a sweetener suppressor, such as a natural sweetener suppressor. It may be combined with an umami taste enhancer, such as an amino acid or a salt thereof.

A composition of the invention can be combined with a polyol or sugar alcohol, a carbohydrate, a physiologically active substance or functional ingredient (for example a carotenoid, dietary fiber, fatty acid, saponin, antioxidant, nutraceutical, flavonoid, isothiocyanate, phenol, plant sterol or stanol (phytosterols and phytostanols), a polyols, a prebiotic, a probiotic, a phytoestrogen, soy protein, sulfides/thiols, amino acids, a protein, a vitamin, a mineral, and/or a substance classified based on a health benefits, such as cardiovascular, cholesterol-reducing or anti-inflammatory.

A composition of the invention may include a flavoring agent, an aroma component, a nucleotide, an organic acid, an organic acid salt, an inorganic acid, a bitter compound, a protein or protein hydrolyzate, a surfactant, a flavonoid, an astringent compound, a vitamin, a dietary fiber, an antioxidant, a fatty acid and/or a salt.

A composition of the invention may be applied as a high intensity sweetener to produce zero calorie, reduced calorie or diabetic beverages and food products with improved taste characteristics. Also it can be used in drinks, foodstuffs, pharmaceuticals, and other products in which sugar cannot be used.

In addition, a composition of the invention may be used as a sweetener not only for drinks, foodstuffs, and other products dedicated for human consumption, but also in animal feed and fodder with improved characteristics.

The examples of products where a composition of the invention can be used as a sweetening compound can be as alcoholic beverages such as vodka, wine, beer, liquor, sake, etc; natural juices, refreshing drinks, carbonated soft drinks, diet drinks, zero calorie drinks, reduced calorie drinks and foods, yogurt drinks, instant juices, instant coffee, powdered types of instant beverages, canned products, syrups, fermented soybean paste, soy sauce, vinegar, dressings, mayonnaise, ketchups, curry, soup, instant bouillon, powdered soy sauce, powdered vinegar, types of biscuits, rice biscuit, crackers, bread, chocolates, caramel, candy, chewing gum, jelly, pudding, preserved fruits and vegetables, fresh cream, jam, marmalade, flower paste, powdered milk, ice cream, sorbet, vegetables and fruits packed in bottles, canned and boiled beans, meat and foods boiled in sweetened sauce, agricultural vegetable food products, seafood, ham, sausage, fish ham, fish sausage, fish paste, deep fried fish products, dried seafood products, frozen food products, preserved seaweed, preserved meat, tobacco, medicinal products, and many others. In principal it can have unlimited applications.

The sweetened composition comprises a beverage, non-limiting examples of which include non-carbonated and carbonated beverages such as colas, ginger ales, root beers, ciders, fruit-flavored soft drinks (e.g., citrus-flavored soft drinks such as lemon-lime or orange), powdered soft drinks, and the like; fruit juices originating in fruits or vegetables, fruit juices including squeezed juices or the like, fruit juices containing fruit particles, fruit beverages, fruit juice beverages, beverages containing fruit juices, beverages with fruit flavorings, vegetable juices, juices containing vegetables, and mixed juices containing fruits and vegetables; sport drinks, energy drinks, near water and the like drinks (e.g., water with natural or synthetic flavorants); tea type or favorite type beverages such as coffee, cocoa, black tea, green tea, oolong tea and the like; beverages containing milk components such as milk beverages, coffee containing milk components, cafe au lait, milk tea, fruit milk beverages, drinkable yogurt, lactic acid bacteria beverages or the like; and dairy products.

Generally, the amount of sweetener present in a sweetened composition varies widely depending on the particular type of sweetened composition and its desired sweetness. Those of ordinary skill in the art can readily discern the appropriate amount of sweetener to put in the sweetened composition.

During the manufacturing of foodstuffs, drinks, pharmaceuticals, cosmetics, table top products, chewing gum the conventional methods such as mixing, kneading, dissolution, pickling, permeation, percolation, sprinkling, atomizing, infusing and other methods can be used.

Thus, compositions which incorporate a composition of the invention can be made by any method known to those skilled in the art that provide homogenous even or homogeneous mixtures of the ingredients. These methods include dry blending, spray drying, agglomeration, wet granulation, compaction, co-crystallization and the like.

In solid form a composition of the invention can be provided to consumers in any form suitable for delivery into the comestible to be sweetened, including sachets, packets, bulk bags or boxes, cubes, tablets, mists, or dissolvable strips. The composition can be delivered as a unit dose or in bulk form.

For liquid sweetener systems and compositions convenient ranges of fluid, semi-fluid, paste and cream forms, appropriate packing using appropriate packing material in any shape or form shall be invented which is convenient to carry or dispense or store or transport any combination containing any of the above sweetener products or combination of product produced above.

A composition of the invention may include various bulking agents, functional ingredients, colorants, flavors.

The terms "sequence homology" or "sequence identity" or "homology" or "identity" are used interchangeably herein. For the purpose of this invention, it is defined here that in order to determine the percentage of sequence homology or sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. Alternatively, the alignment may be carried out over a shorter length, for example over about 20, about 50, about 100 or more nucleic acids/based or amino acids. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J. B. (1983) An overview of sequence comparison In D. Sankoff and J. B. Kruskal, (ed.), Time warps, string edits and macromolecules: the theory and practice of sequence comparison, pp. 1-44 Addison Wesley). The percent sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) J. Mol. Biol. 215:403-10. BLAST nucleotide searches can be performed with the NBLAST program, score=100, wordlength=12 to obtain nucleotide sequences homologous to nucleic acid molecules of the invention. BLAST protein searches can be performed with the XBLAST program, score=50, wordlength=3 to obtain amino acid sequences homologous to protein molecules of the invention. To obtain gapped alignments for comparison purposes, Gapped BLAST can be utilized as described in Altschul et al., (1997) Nucleic Acids Res. 25(17): 3389-3402. When utilizing BLAST and Gapped BLAST programs, the default parameters of the respective programs (e.g., XBLAST and NBLAST) can be used. See the homepage of the National Center for Biotechnology Information at www.ncbi.nlm.nih.gov.

Standard genetic techniques, such as overexpression of enzymes in the host cells, genetic modification of host cells, or hybridisation techniques, are known methods in the art, such as described in Sambrook and Russel (2001) "Molecular Cloning: A Laboratory Manual ($3^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation, genetic modification etc of fungal host cells are known from e.g. EP-A-0 635 574, WO 98/46772, WO 99/60102 and WO 00/37671, WO90/14423, EP-A-0481008, EP-A-0635 574 and U.S. Pat. No. 6,265,186.

EMBODIMENTS OF THE INVENTION

1. A recombinant host capable of producing a steviol glycoside which overexpresses a polypeptide which mediates steviol glycoside transport and which polypeptide comprises the amino acid sequence set forth in SEQ ID NO: 29 or an amino acid sequence having at least about 50% sequence identity thereto.
2. A recombinant host capable of producing a steviol glycoside which has been modified, preferably in its genome, to result in a deficiency in the production of a polypeptide which mediates steviol glycoside transport and which polypeptide comprises the amino acid sequence set forth in SEQ ID NO: 29 or an amino acid sequence having at least about 50% sequence identity thereto.
3. A recombinant host according to claim 1, which comprises a recombinant nucleic acid encoding a polypeptide which comprises the amino acid sequence set forth in SEQ ID NO: 29 or an amino acid sequence having at least about 50% sequence identity thereto.
4. A recombinant host according to any one of the preceding embodiments which comprises one or more recombinant nucleotide sequence(s) encoding:
   a polypeptide having ent-copalyl pyrophosphate synthase activity;
   a polypeptide having ent-Kaurene synthase activity;
   a polypeptide having ent-Kaurene oxidase activity; and
   a polypeptide having kaurenoic acid 13-hydroxylase activity.
5. A recombinant host according to any one of the preceding embodiments, which comprises a recombinant nucleic acid sequence encoding a polypeptide having NADPH-cytochrome p450 reductase activity.
6. A recombinant host according to any one of the preceding embodiments which comprises a recombinant nucleic acid sequence encoding one or more of:
   (i) a polypeptide having UGT74G1 activity;
   (ii) a polypeptide having UGT2 activity;
   (iii) a polypeptide having UGT85C2 activity; and
   (iv) a polypeptide having UGT76G1 activity.
7. A recombinant host according to any one of the preceding embodiments, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.
8. A recombinant host according to embodiment 7, wherein the recombinant host is a *Saccharomyces cerevisiae* cell, a *Yarrowia lipolytica* cell, a *Candida krusei* cell, an *Issatchenkia orientalis* cell or an *Escherichia coli* cell.
9. A recombinant host according to any one of the preceding embodiments, wherein the ability of the host to produce geranylgeranyl diphosphate (GGPP) is upregulated.
10. A recombinant host according to any one of the preceding embodiments which comprises a nucleic acid sequence encoding one or more of:
    a polypeptide having hydroxymethylglutaryl-CoA reductase activity; or
    a polypeptide having farnesyl-pyrophosphate synthetase activity.
11. A recombinant host capable of producing a steviol glycoside which overexpresses a heterologous polypeptide which mediates steviol glycoside transport.
12. A process for the preparation of a steviol glycoside which comprises fermenting a recombinant host according to any one of the preceding embodiments in a suitable fermentation medium and, optionally, recovering the steviol glycoside.
13. A process according to embodiment 12 for the preparation of a steviol glyocisde, optionally wherein the process is carried out on an industrial scale.
14. A fermentation broth comprising a steviol glycoside obtainable by the process according to embodiment 12 or 13.
15. A steviol glycoside obtained by a process according to embodiment 12 or 13 or obtained from a fermentation broth according to embodiment 14.
16. A composition obtainable by a process according to embodiment 12 or 13, a composition comprising two or more steviol glycosides obtained by a process according to embodiment 12 or 13 or a composition obtained from a fermentation broth according to embodiment 14.
17. A foodstuff, feed or beverage which comprises a steviol glycoside according to claim 15 or a composition according to claim 16.

A reference herein to a patent document or other matter which is given as prior art is not to be taken as an admission that that document or matter was known or that the information it contains was part of the common general knowledge as at the priority date of any of the claims.

The disclosure of each reference set forth herein is incorporated herein by reference in its entirety.

The present invention is further illustrated by the following Examples:

EXAMPLES

General

Standard genetic techniques, such as overexpression of enzymes in the host cells, as well as for additional genetic modification of host cells, are known methods in the art, such as described in Sambrook and Russel (2001) "Molecular Cloning: A Laboratory Manual (3$^{rd}$ edition), Cold Spring Harbor Laboratory, *Cold Spring Harbor Laboratory Press*, or F. Ausubel et al, eds., "Current protocols in molecular biology", Green Publishing and Wiley Interscience, New York (1987). Methods for transformation and genetic modification of fungal host cells are known from e.g. EP-A-0 635 574, WO 98/46772, WO 99/60102 and WO 00/37671.

Example 1: Description of Steviol Glycoside Production Strain ML14094 (MAT-A Lineage)

Two *Yarrowia lipolytica* strains of mating types MATA and MATB were engineered for steviol glycoside production. These strains were mated, the diploid sporulated, and spores with steviol glycoside production were selected. One of these spores was further developed for the production of steviol glycosides, including the production of Rebaudioside A.

Figure 2:
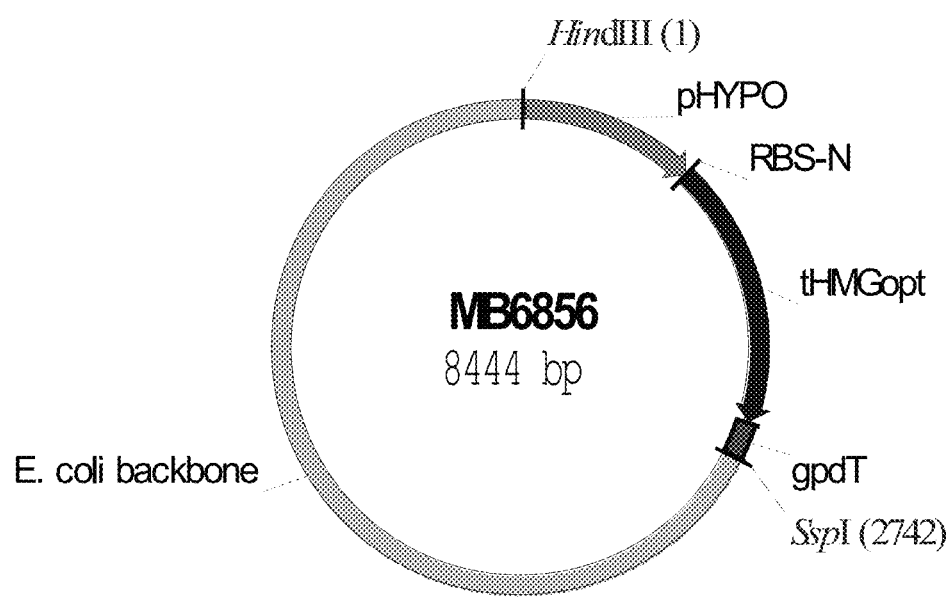
FIG. 2 sets out a schematic representation of the plasmid MB6856, encoding tHMG.
Figure 3:
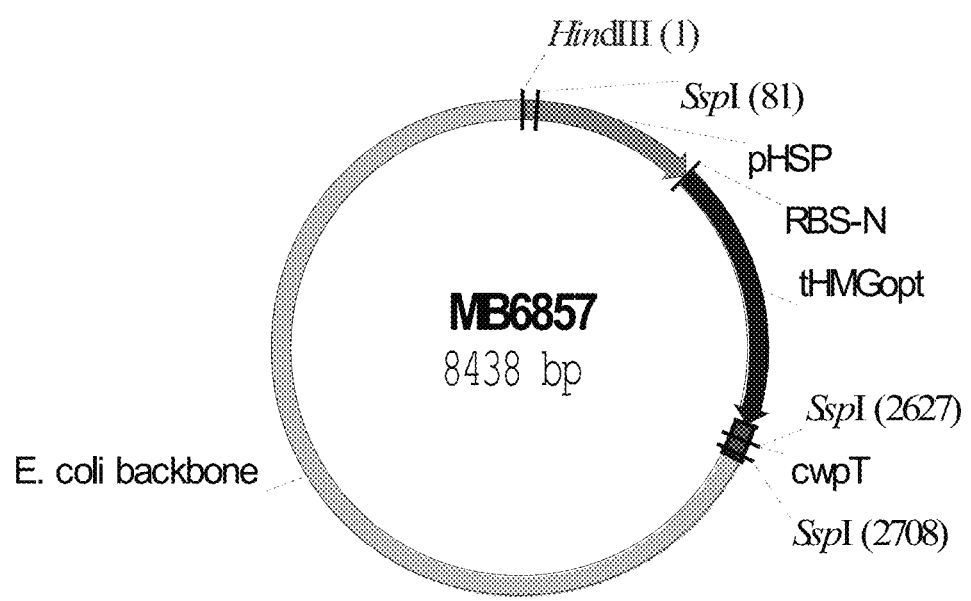
FIG. 3 sets out a schematic representation of the plasmid MB6857, encoding tHMG.
Figure 4:
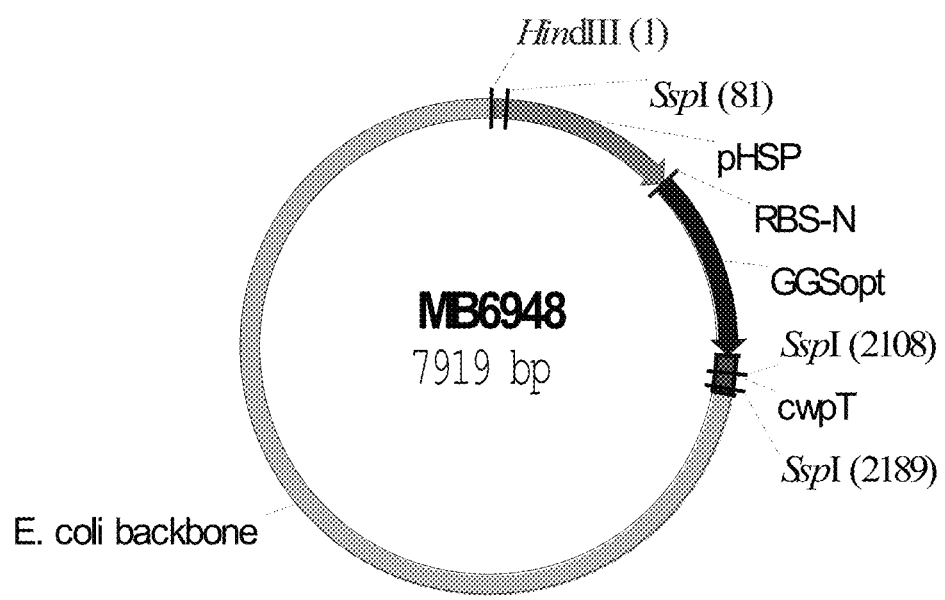
FIG. 4 sets out a schematic representation of the plasmid MB6948, encoding GGS.
Figure 5:
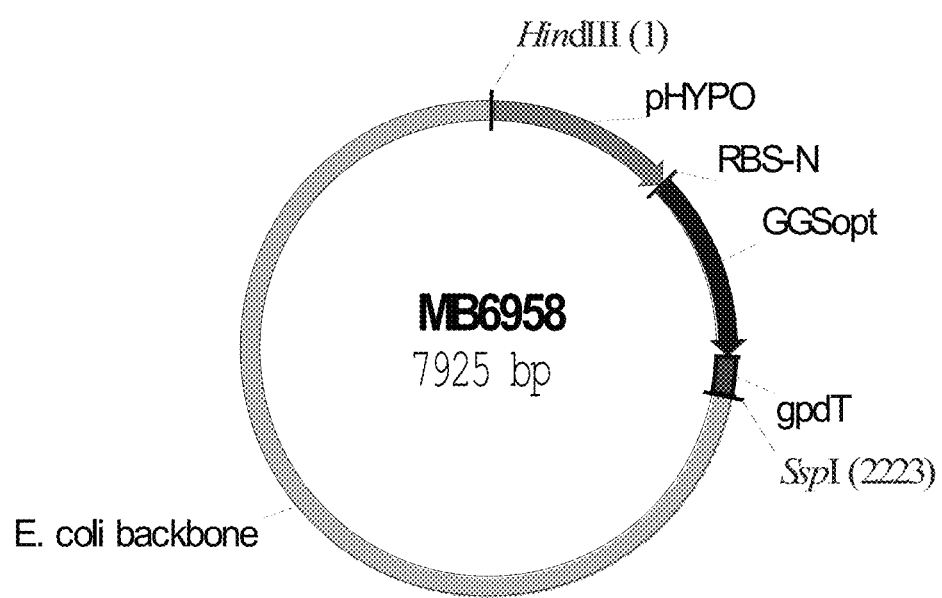
FIG. 5 sets out a schematic representation of the plasmid MB6958, encoding GGS.

Step 1: Strain ML10371 (MAT-A, lys1-, ura3-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.
1) a 7.0 kb DNA fragment isolated by gel purification following HindIII/NotI digestion of plasmid MB6969 (FIG. 1). This construct encodes a synthetic construct for the overexpression of UGT2_1a (SEQ ID NO: 1) linked to the pPGM promoter (SEQ ID NO: 2) and xprT terminator (SEQ ID NO: 9) and the HPH hygromycin resistance gene, together flanked by lox sites (Güldener et al, 1996, Lambert et al, 2007), and a synthetic construct for the overexpression of the codon optimized *Y. lipolytica* hydroxymethylglutaryl-coenzyme A reductase open reading frame lacking the 5' membrane anchor sequence (tHMGopt: SEQ ID NO: 15) linked to the pHSP promoter (SEQ ID NO: 3) and cwpT terminator (SEQ ID NO: 10).
2) a 2.7 kb DNA fragment isolated by gel purification following HindIII/SspI digestion of MB6856 (FIG. 2). This construct encodes tHMGopt (SEQ ID NO: 15) linked to the pHYPO promoter (SEQ ID NO: 4) and gpdT terminator (SEQ ID NO: 11).
3) a 2.5 kb DNA fragment isolated by gel purification following SspI digestion of MB6857 (FIG. 3). This construct encodes tHMGopt (SEQ ID NO: 15) linked to the pHSP promoter (SEQ ID NO: 3) and cwpT terminator (SEQ ID NO: 10).
4) a 2.0 kb DNA fragment isolated by gel purification following SspI digestion of MB6948 (FIG. 4). This construct encodes a synthetic construct for the overexpression of the codon optimized *Y. lipolytica* geranyl-geranyl-pyrophosphate synthetase (GGSopt: SEQ ID NO: 16) linked to the pHSP promoter (SEQ ID NO: 3) and cwpT terminator (SEQ ID NO: 10).
5) a 2.2 kb DNA fragment isolated by gel purification following HindIII/SspI digestion of MB6958 (FIG. 5). This construct encodes GGSopt (SEQ ID NO: 16) linked to the pHYPO promoter (SEQ ID NO: 4) and gpdT terminator (SEQ ID NO: 11). The resulting strain was denoted ML13462.

Figure 6:
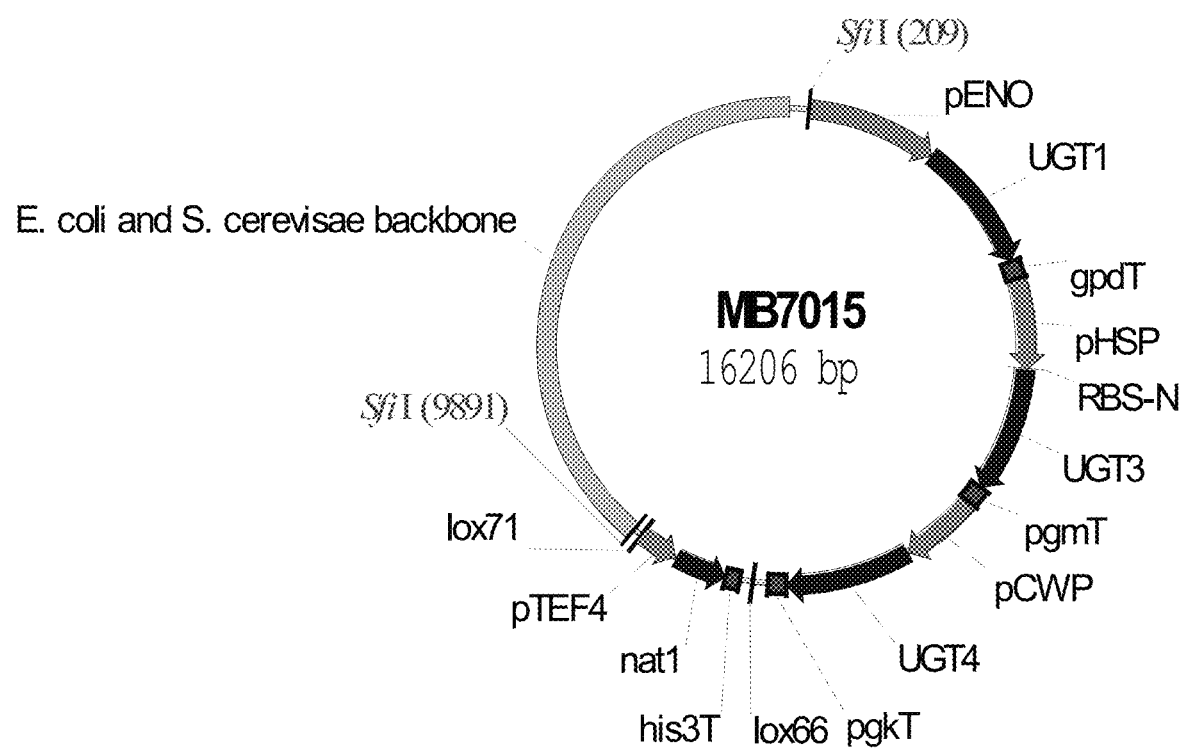
FIG. 6 sets out a schematic representation of the plasmid MB7015, encoding UGT1, UGT3, UGT4, NAT.

Step 2. Strain ML13462 was transformed with a 9.7 kb fragment isolated by gel purification following SfiI digestion of plasmid MB7015 (FIG. 6). This construct encodes a synthetic construct for the overexpression of UGT1 (SEQ ID NO: 17) linked to the pENO (SEQ ID NO: 5) promoter and gpdT terminator (SEQ ID NO: 11), UGT3 (SEQ ID NO: 18) linked to the pHSP promoter (SEQ ID NO: 3) and pgmT terminator (SEQ ID NO: 12), UGT4 (SEQ ID NO: 19) linked to the pCWP (SEQ NO: 6) promoter and pgkT terminator (SEQ ID NO: 13), and the lox-flanked nourseothricin resistance marker (NAT). Note that placement of lox sites allows for subsequent removal of nourseothricin resistance via CRE recombinase mediated recombination. A nourseothricin resistant isolate was denoted ML13500.

Figure 7:
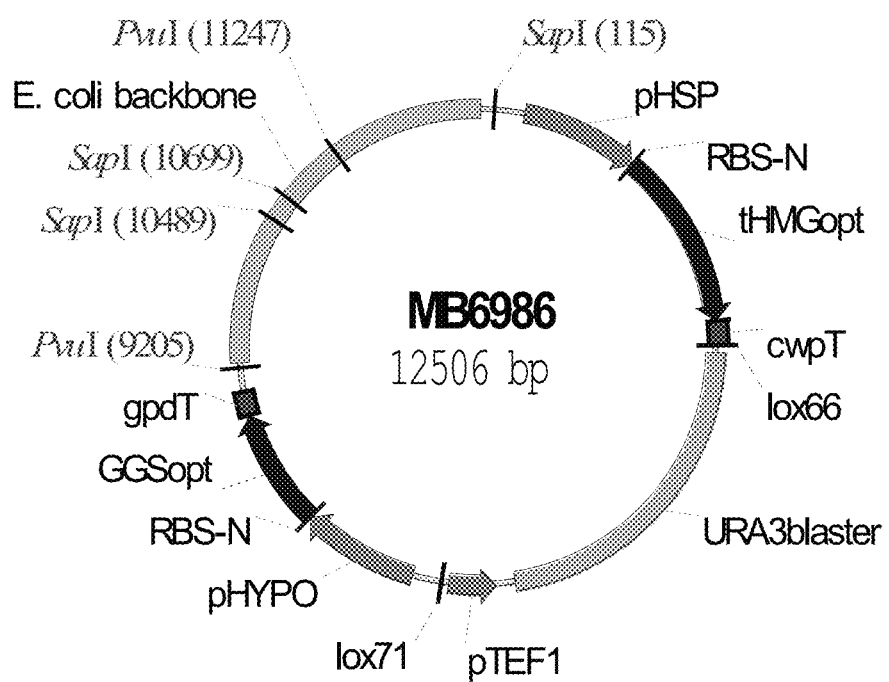
FIG. 7 sets out a schematic representation of the plasmid MB6986, encoding tHMG, URA3, GGS.

Step 3. Strain ML13500 was transformed with a 9.1 kb fragment isolated by gel purification following PvuI/SapI digestion of plasmid MB6986 (FIG. 7). This construct encodes tHMGopt (SEQ ID NO: 15) linked to the pHSP promoter (SEQ ID NO: 3) and cwpT terminator (SEQ ID NO: 10), the lox-flanked URA3blaster prototrophic marker, and GGSopt (SEQ ID NO: 16) linked to the pHYPO promoter (SEQ ID NO: 4) and gpdT terminator (SEQ ID NO: 11). Transformants were selected on minimal medium lacking uracil. One selected uracil prototroph was denoted ML13723.

Figure 8:
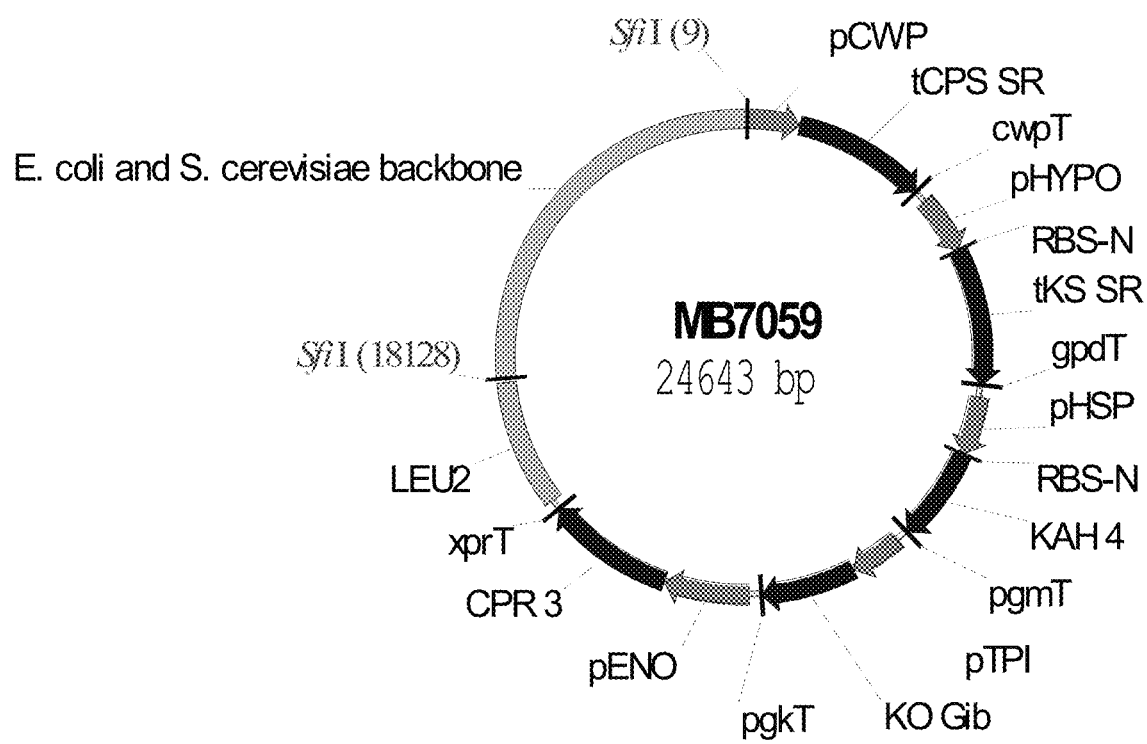
FIG. 8 sets out a schematic representation of the plasmid MB7059, encoding tCPS_SR, tKS_SR, KAH_4, KO_Gib, CPR_3, LEU2.

Step 4. Strain ML13723 was transformed with an 18.1 kb fragment isolated by gel purification following SfiI digestion of plasmid MB7059 (FIG. 8). MB7059 encodes the tCPS_SR (SEQ ID NO: 20) linked to pCWP promoter (SEQ ID NO: 6) and cwpT terminator (SEQ ID NO: 10), the tKS_SR (SEQ ID NO: 21) linked to the pHYPO promoter (SEQ ID NO: 4) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pTPI promoter (SEQ ID NO: 7) and pgkT terminator (SEQ ID NO: 13), the CPR_3 (SEQ ID NO: 24) linked to the pENO promoter (SEQ ID NO: 5) and xprT terminator (SEQ ID NO: 9) and the native *Y. lipolytica* LEU2 locus. One selected rebaudioside A-producing transformant was denoted ML14032.

Step 5. Strain ML14032 was struck to YPD and grown overnight and then struck to 5-FOA plates to allow for recombination mediated loss of the URA3 marker introduced previously. One selected 5-FOA resistant transformant was denoted ML14093.

Figure 9:
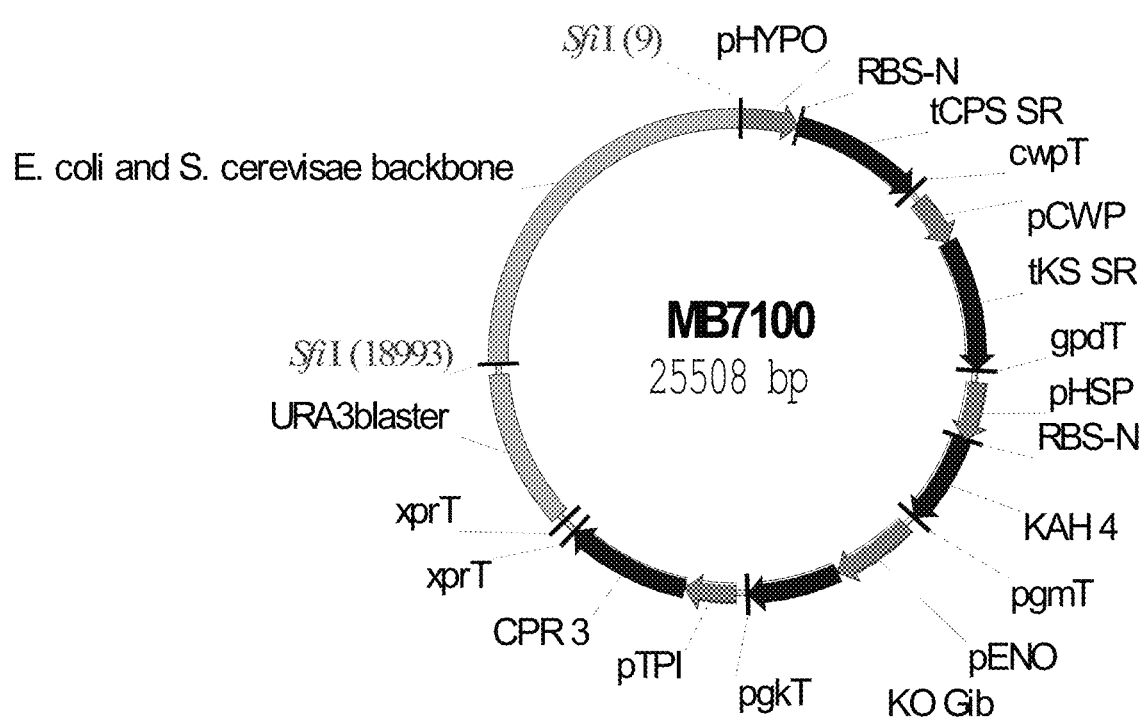
FIG. 9 sets out a schematic representation of the plasmid MB7100, encoding tCPS_SR, tKS_SR, KAH_4, KO_Gib, CPR_3, URA3.

Step 6. Strain ML14093 was transformed with a 19.0 kb fragment isolated by gel purification following SfiI digestion of plasmid MB7100 (FIG. 9). MB7100 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and URA3blaster prototrophic marker. Transformants were selected on minimal medium lacking uracil. One selected rebaudioside A producing uracil prototroph was denoted ML14094.

Example 2. Description of Steviol Glycoside Production Strain ML14087 (MAT-B Lineage)

Figure 10:
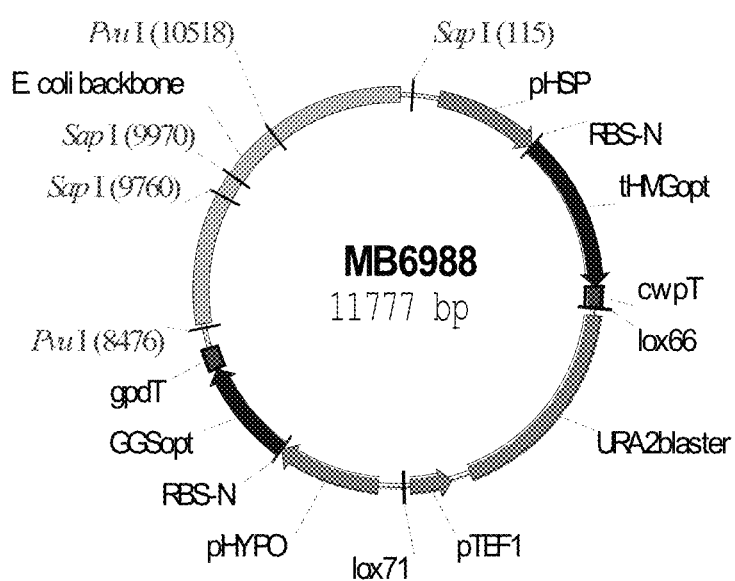
FIG. 10 sets out a schematic representation of the plasmid MB6988, encoding tHMG, URA2, GGS.
Figure 11:
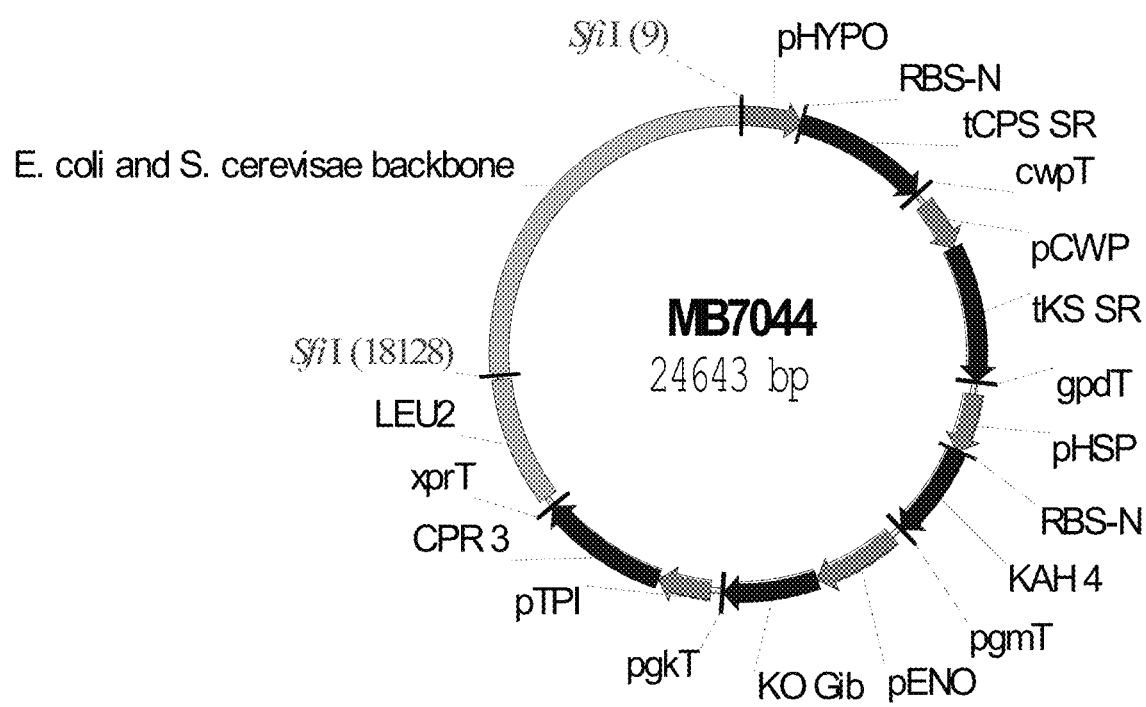
FIG. 11 sets out a schematic representation of the plasmid MB7044, encoding tCPS_SR, tKS_SR, KAH_4, KO_Gib, CPR_3, LEU2.
Figure 12:
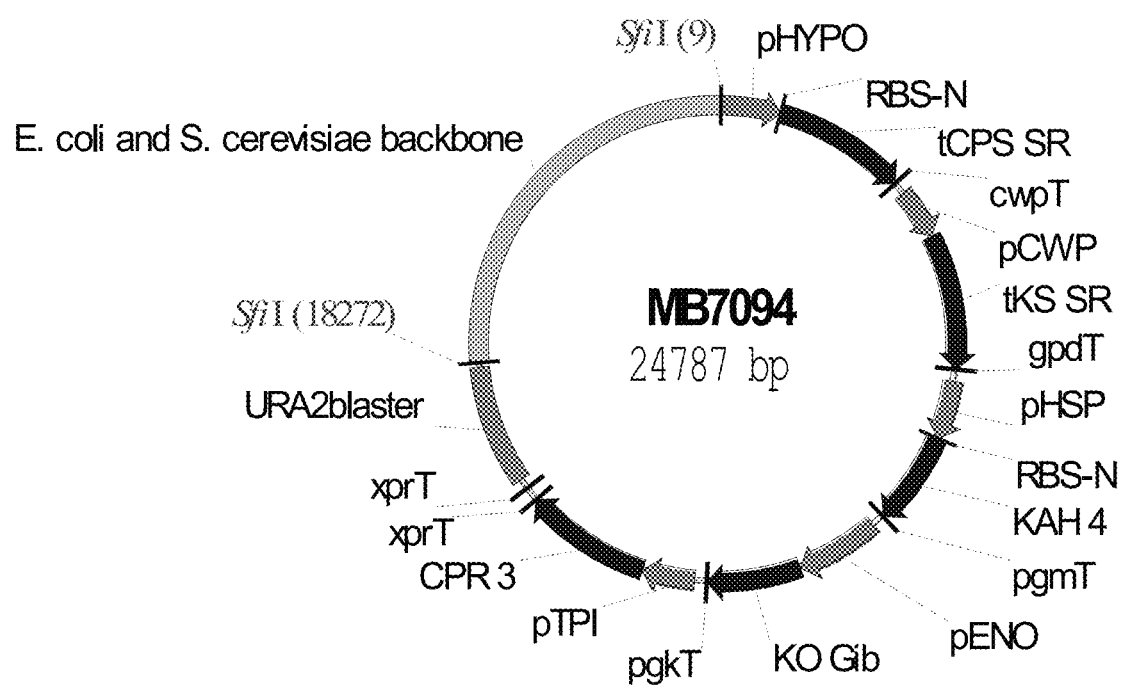
FIG. 12 sets out a schematic representation of the plasmid MB7094, encoding tCPS_SR, tKS_SR, KAH_4, KO_Gib, CPR_3, URA2.

Step 1. Strain ML13206 (MAT-β, ade1-, ure2-, leu2-) was transformed with 5 defined DNA fragments. All transformations were carried out via a lithium acetate/PEG fungal transformation protocol method and transformants were selected on minimal medium, YPD+100 ug/ml nourseothricin or YPD+100 ug/ml hygromycin, as appropriate.
  1) a 7.0 kb DNA fragment isolated by gel purification following HindIII/NotI digestion of plasmid MB6969 (FIG. 1). This construct encodes a synthetic construct for the overexpression of the codon pair optimized (CpO) ORF of UGT2_1a (SEQ ID NO: 1) linked to the pPGM (SEQ ID NO: 2) promoter and xprT terminator (SEQ ID NO: 9) and the HPH hygromycin resistance gene, together flanked by lox sites (Güldener et al, 1996, Lambert et al, 2007), and a synthetic construct for the overexpression of the codon optimized *Y. lipolytica* hydroxymethylglu-taryl-coenzyme A reductase open reading frame lacking the 5' membrane anchor sequence (tHMGopt: SEQ ID NO: 15) linked to the pHSP promoter (SEQ ID NO: 3) and cwpT terminator (SEQ ID NO: 10).
  2) a 2.7 kb DNA fragment isolated by gel purification following HindIII/SspI digestion of MB6856 (FIG. 2). This construct encodes tHMGopt (SEQ ID NO: 15) linked to the pHYPO promoter (SEQ ID NO: 4) and gpdT terminator (SEQ ID NO: 11).
  3) a 2.5 kb DNA fragment isolated by gel purification following SspI digestion of MB6857 (FIG. 3). This construct encodes tHMGopt (SEQ ID NO: 15) linked to the pHSP promoter (SEQ ID NO: 3) and cwpT terminator (SEQ ID NO: 10).
  4) a 2.0 kb DNA fragment isolated by gel purification following SspI digestion of MB6948 (FIG. 4). This construct encodes a synthetic construct for the overexpression of the codon optimized *Y. lipolytica* geranyl-geranyl-pyrophosphate synthetase (GGSopt: SEQ ID NO: 16) linked to the pHSP promoter (SEQ ID NO: 3) and cwpT terminator (SEQ ID NO: 10).
  5) a 2.2 kb DNA fragment isolated by gel purification following HindIII/SspI digestion of MB6958 (FIG. 5). This construct encodes GGSopt (SEQ ID NO: 16) linked to the pHYPO (SEQ ID NO: 4) promoter and gpdT terminator (SEQ ID NO: 11). The resulting strain was denoted ML13465.
Step 2. Strain ML13465 was transformed with 2 defined DNA fragments:
  1). a 9.7 kb fragment isolated by gel purification following SfiI digestion of plasmid MB7015 (FIG. 6). This construct encodes a synthetic construct for the overexpression of UGT1 (SEQ ID NO: 17) linked to the pENO promoter (SEQ ID NO: 5) and gpdT (SEQ ID NO: 11) terminator, UGT3 (SEQ ID NO: 18) linked to the pHSP promoter (SEQ ID NO: 3) and pgmT terminator (SEQ ID NO: 12), UGT4 (SEQ ID NO: 19) linked to the pCWP promoter (SEQ ID NO: 6) and pgkT terminator (SEQ ID NO: 13), and the lox-flanked nourseothricin resistance marker (NAT). Note that placement of lox sites allows for subsequent removal of nourseothricin resistance via CRE recombinase mediated recombination.
  2). a 9.1 kb fragment isolated by gel purification following PvuI/SapI digestion of plasmid MB6988 (FIG. 10). This construct encodes tHMGopt (SEQ ID NO: 15) linked to the pHSP promoter (SEQ ID NO: 3) and cwpT terminator (SEQ ID NO: 10), the lox-flanked URA2blaster prototrophic marker, and GGSopt (SEQ ID NO: 16) linked to the pHYPO promoter (SEQ ID NO: 4) and gpdT terminator (SEQ ID NO: 11). Strains were selected on YPD+ 100 ug/ml nourseothricin and replica plated to minimal medium lacking uracil. A nourseothricin resistant, uracil prototrophic isolate was denoted ML13490
Step 3. Strain ML13490 was struck to YPD and grown overnight and then struck to 5-FOA plates to allow for recombination mediated loss of the URA2 marker introduced previously. One selected 5-FOA resistant transformant was denoted ML13501.
Step 4. Strain ML13501 was transformed with a 9.1 kb fragment isolated by gel purification following PvuI/SapI digestion of plasmid MB6988 (FIG. 10). Transformants were selected on minimal medium lacking uracil. One selected uracil prototroph was denoted ML13724.
Step 5. Strain ML13724 was transformed with an 18.1 kb fragment isolated by gel purification following SfiI digestion of plasmid MB7044 (FIG. 11). MB7044 encodes the CPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9) and the LEU2 locus. One selected rebaudioside A-producing transformant was denoted ML14044.
Step 6. Strain ML14044 was struck to YPD and grown overnight and then struck to 5-FOA plates to allow for recombination mediated loss of the URA2 marker introduced previously. One selected 5'-FOA resistant transformant was denoted ML14076.
Step 7. Strain ML14076 was transformed with a 19.0 kb fragment isolated by gel purification following SfiI digestion of plasmid MB7094 (FIG. 12). MB7094 encodes the tCPS_SR (SEQ ID NO: 20) linked to the pHYPO promoter (SEQ ID NO: 4) and cwpT terminator (SEQ ID NO: 10), the tKS_SR (SEQ ID NO: 21) linked to the pCWP promoter (SEQ ID NO: 6) and gpdT terminator (SEQ ID NO: 11), the KAH_4 (SEQ ID NO: 22) linked to the pHSP promoter (SEQ ID NO: 3) and pgmT terminator (SEQ ID NO: 12), the KO_Gib (SEQ ID NO: 23) linked to the pENO promoter (SEQ ID NO: 5) and pgkT terminator (SEQ ID NO: 13), the CPR_3 (SEQ ID NO: 24) linked to the pTPI promoter (SEQ ID NO: 7) and xprT terminator (SEQ ID NO: 9)

and URA2blaster prototrophic marker. Transformants were selected on minimal medium lacking uracil. One selected rebaudioside A producing uracil prototroph was denoted ML14087.

Example 3. Mating MATA and MATB Lineage and Selecting Steviol Glycoside-Producing Progeny Strains of opposite mating types (ML14094 and ML14087) with complementary nutritional deficiencies (ADE1+lys1− and ade1−LYS1+) were allowed to mate and then plated on selective media that would allow only diploids to grow (minimal media lacking both adenine and lysine). Diploid cells (ML14143) were then induced to undergo meiosis and sporulation by starvation, and the resulting haploid progenies were replica-plated to identify prototrophic isolates with hygromycin and nourseothricin resistance. One selected rebaudioside A-producing strain was denoted ML14737

Example 4. Making the Strain UGT2 1a-Free

Figure 13:
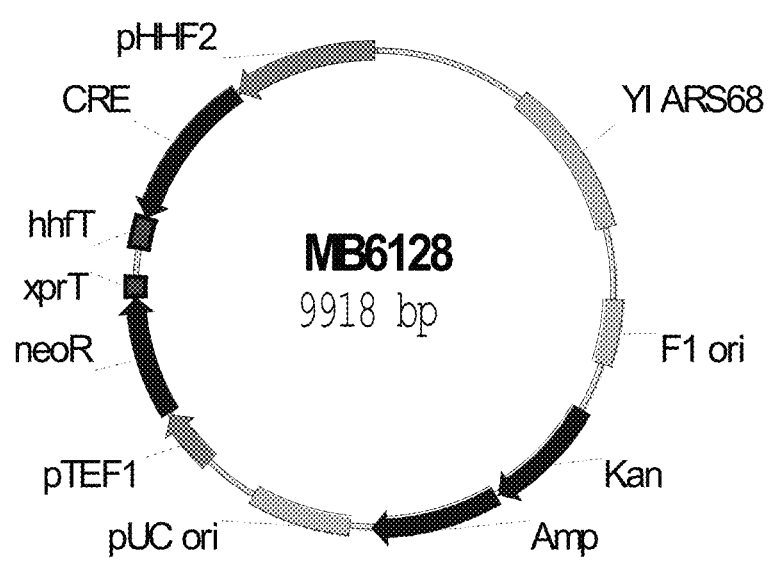
FIG. 13 sets out a schematic representation of the plasmid MB6128, encoding CRE, neoR.

The hygromycin antibiotic marker and the nourseothricin antibiotic marker were removed from strain ML14737 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator, and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14869. This strain no longer produces rebaudioside A due to the loss of UGT2_1a along with the hygromycin resistance and produces the intermediate rubusoside instead.

Example 5. Introduction of UGT2 10b

ML14869 was transformed with a 4.2 kb DNA fragment produced by PCR and purified following gel electrophoresis. The fragment encoded a sequence optimized variant of UGT2_10 b (SEQ ID NO: 25) and hygromycin resistance. The DNA fragment was generated by fusion PCR as follows. UGT2_10 b was codon pair optimized for expression in *Y. lipolytica* and synthesized by DNA2.0, linked to the native *Yarrowia lipolytica* pHSP promoter and gpdT terminator and flanked by connector sequences. This 1.4 kb DNA fragment was amplified using appropriate oligos and purified by gel electrophoresis. The HPH marker was flanked by lox sites, and linked to the *Ashbya gossypii* pTEF1 promoter and tef1T terminator and flanked by connector sequences. This 1.8 kb DNA fragment was amplified using appropriate oligos and purified by gel electrophoresis. A 4.2 kb DNA fragment was obtained by PCR using these two DNA fragments with followed by gel electrophoresis and purification. Transformation of ML14869 with this defined DNA fragment and selection on YPD+100 ug/ml hygromycin yielded the rebaudioside A producing strain ML14937.

Example 6. Making Strain ML14937 Marker-Free

The hygromycin antibiotic marker was removed from strain ML14937 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator and a neoR (encoding for G418 resistance) under the control of the native *Yarrowia lipolytica* pTEF1 promoter and xprT terminator. After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). The resulting antibiotic marker-free variant is denoted ML14958.

Example 7. Transformation with Extra Gene Copies

Figure 14:
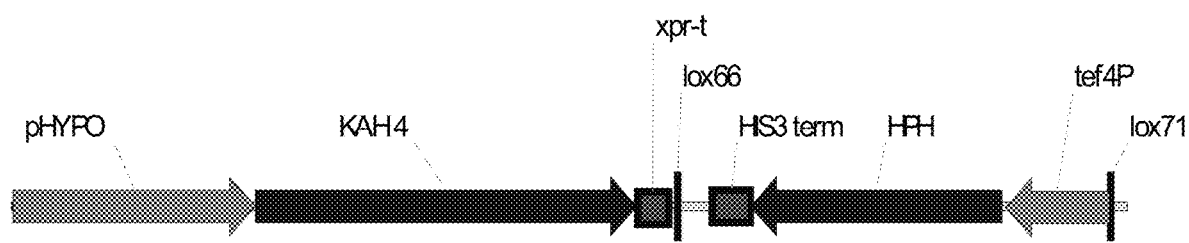
FIG. 14 sets out a schematic representation of the construct containing KAH and HPH.
Figure 15:
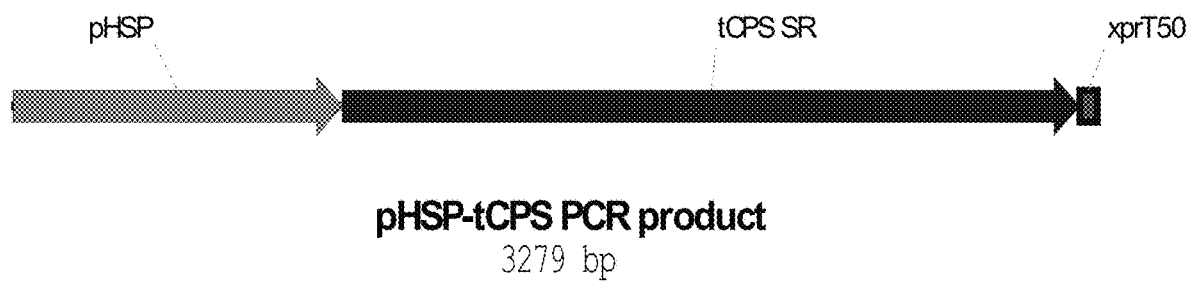
FIG. 15 sets out a schematic representation of the construct containing tCPS_SR.
Figure 16:
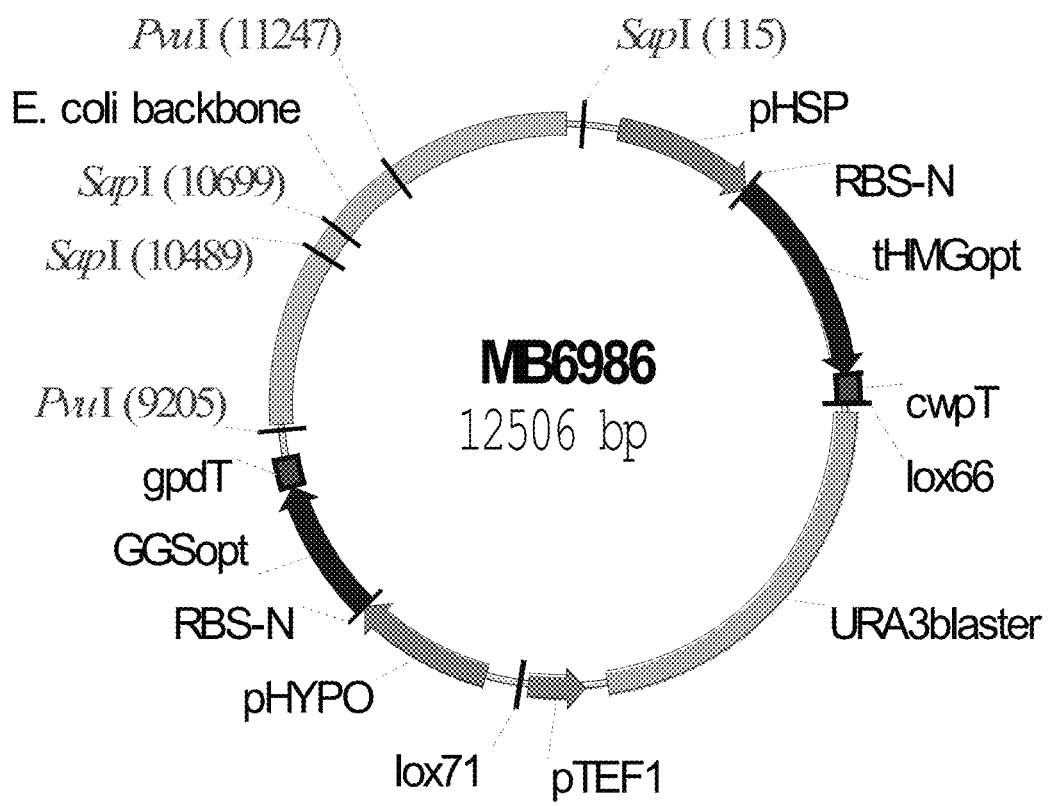
FIG. 16 sets out a schematic representation of the plasmid MB6986, encoding tHMG, URA3, GGS.

Strain ML14958 was struck to YPD and grown overnight and then struck to 5-FOA plates to allow for recombination-mediated loss of the URA2 marker. One selected 5'-FOA resistant transformant was denoted ML15075. Strain ML15075 was transformed with 3 defined DNA fragments and selected for transformation on YPD with 100 ug/ml hygromycin. The three fragments were as follows:
1) a 4.6 kb DNA fragment encoding the KAH open reading frame linked to the native *Y. lipolytica* pHYPO promoter and the xprT terminator and also encoding the HPH hygromycin resistance gene flanked by lox sites, produced by PCR and purified following gel electrophoresis. Sequences were assembled in *Saccharomyces cerevisiae*, and DNA from this *S. cerevisiae* strain was used as template for PCR yielding the 4.6 kb DNA fragment (see FIG. 14) used to transform ML15075.
2) a 3.3 kb DNA fragment encoding the tCPS open reading frame linked to the native *Y. lipolytica* pHSP promoter and xprT terminator, produced by PCR and purified following gel electrophoresis. Sequences were assembled in *Saccharomyces cerevisiae*, and DNA from this *S. cerevisiae* strain was used as template for PCR yielding the 3.3 kb DNA fragment (FIG. 15) used to transform ML15075.
3) a 9.1 kb fragment isolated by gel purification following PvuI/SapI digestion of plasmid MB6986 (FIG. 16). This construct encodes tHMG linked to the native *Y. lipolytica* HSP promoter and CWP terminator, the lox-flanked URA3blaster prototrophic marker, and GGS1 linked to the native *Y. lipolytica* HYPO promoter and GPD terminator. ML15075 is auxotrophic due to a mutation in ura2, so this fragment was not selected for.

One selected hygromycin-resistant transformant was denoted ML15085.

Example 8. Transformation of Extra Copies of tHMG and GGS

Strain ML15085 was transformed with a 8.4 kb fragment isolated by gel purification following PvuI/SapI digestion of plasmid MB6988 (FIG. 10). This construct encodes tHMGopt linked to the native *Y. lipolytica* pHSP promoter and cwpT terminator, the lox-flanked URA2blaster prototrophic marker, and GGSopt linked to the native *Y. lipolytica* pHYPO promoter and gpdT terminator. Transformants were selected on minimal medium lacking uracil. One selected uracil prototroph was denoted ML15086.

Example 9. Making Strain ML15086 Marker-Free

The hygromycin antibiotic marker was removed from strain ML15086 after transformation with MB6128 (FIG. 13) which encodes a construct for constitutive overexpression of the CRE recombinase. CRE recombinase deletes the antibiotics markers by recombination over the Lox66 and Lox71 sites. An inactive Lox72 site is left in the genome (Güldener et al, 1996, Lambert et al, 2007). Plasmid MB6128 is a CEN plasmid which replicates episomally in *Yarrowia lipolytica* and which contains the CRE recombinase coding region under control of the native *Yarrowia lipolytica* pHHF promoter and hhfT terminator and a neoR (encoding for G418 resistance) under the control of the native *Yarrowia lipolytica* pTEF1 promoter and xprT terminator.

After selection of MB6128 transformants on YPD+G418 and screening for transformants that lost hygromycin and nourseothricin resistance by successful Cre-Lox recombination, the sensitive colonies were grown on non-selective medium to remove the MB6128 CEN plasmid (spontaneous loss of the CEN plasmid). One prototrophic, antibiotic marker-free variant is denoted ML15087.

Example 10. Disruption of YALI0C08701 in *Y. lipolytica* ML15087

To increase the efficiency of targeted transporter disruptions and avoid integration events at other loci in the genome than targeted for, YALI0C08701 (SEQ ID NO: 26), an important factor in non-homologous end joining, was disrupted. Disruption constructs were designed based on single cross-over integration using internal homologous fragments to target the disruption construct to the YALI0C08701 ORF. The internal homologous fragments used to assemble the disruption constructs were PCR amplified from *Y. lipolytica* genomic DNA using suitable primers which were elongated with appropriate connector sequences. The total length of the PCR fragments was 600 bp. 500 bp of these fragments are homologous to the targeted YALI0C08701 and 50 bp to the vector backbone and KanMX marker cassette. The KanMX marker cassette was PCR amplified with suitable primers. For both flanks and marker cassette six 50 µl PCR reactions were perfomed using Phusion polymerase (New England Biolabs) according to suppliers' instructions. The PCR products were purified and concentrated using NucleoSpin Gel and PCR Clean-up Kit (Machery Nagel).

Figure 17:
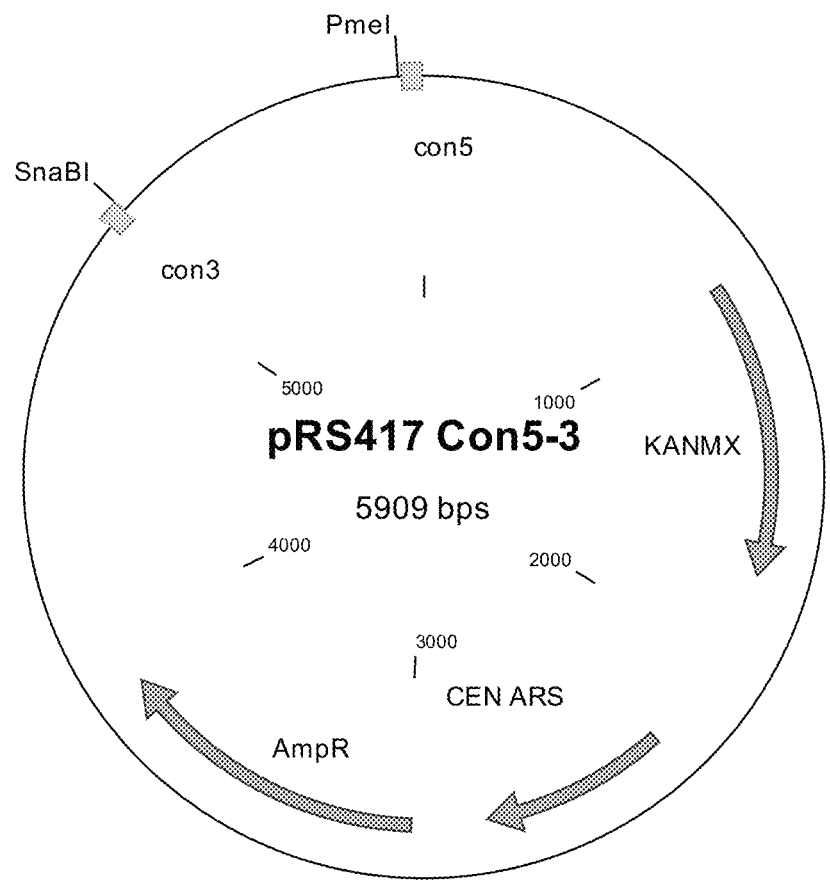
FIG. 17 sets out a schematic representation of the plasmid pRS417 Con5-3.

The flanks and marker were assembled in the SnaBI/PmeI digested pRS417 5_3 (FIG. 17) shuttle vector backbone in-vivo by transforming both flanks, the KanMX fragment and the linear pRS417 5_3 shuttle vector to *S. cerevisiae* CEN.PK113-7D. After transformation and recovery for 2 hours in YEPhD at 30° C. the cells were plated on YEPhD agar with 200 µg/ml G418 (Invitrogen). The plates were incubated at 30° C. for 2 days. Transformants were cultured in YEPD+200 µg/ml G418 at 30° C. Plasmid DNA was isolated and purified.

Correct assembly of the disruption cassettes was established with diagnostic PCR. The expression cassettes were PCR amplified in six 50 µl PCR reactions. The PCR product was purified and concentrated using NucleoSpin Gel and PCR Clean-up Kit (Machery Nagel). 1 µg of the PCR amplified disruption cassette was transformed to *Y. lipolytica* strain ML15087. After transformation and recovery for 2 hours in YEPhD at 30° C. the cells were plated on YEPhD agar with 400 µg/ml G418. The plates were incubated at 30° C. for 2 days. Transformants were purified by re-streaking them on YEPhD agar with 400 µg/ml G418. One of the transformants was named STV2049. Correct integration was established with diagnostic PCR using appropriate oligo's.

Example 11. Disruption of Transporter YALI0E25201 in *Y. lipolytica* STV2049

Figure 18:
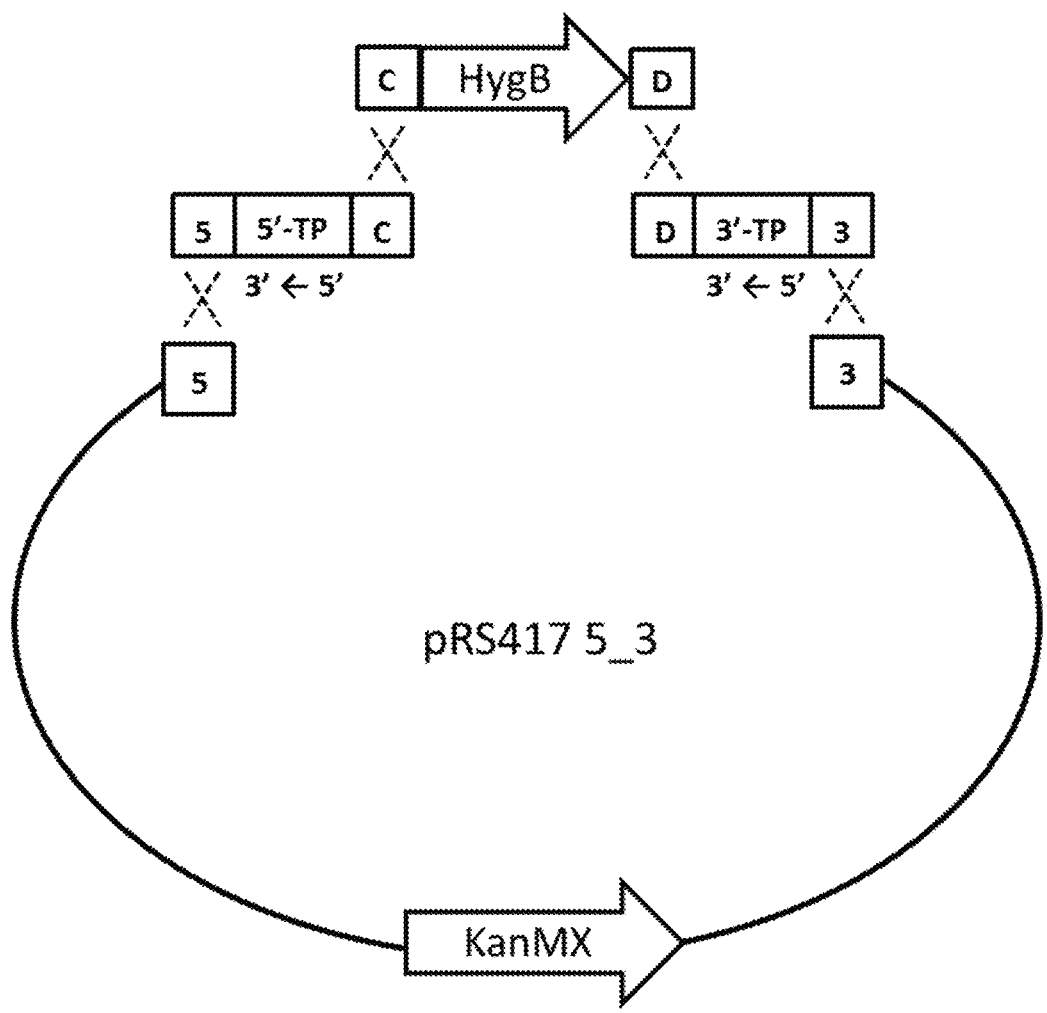
FIG. 18 sets out a schematic representation of the assembly of the HygB marker with the transporter internal fragments in plasmid pRS417 5-3.

Disruption constructs were designed based on single cross-over integration using internal homologues fragments to target the disruption construct to the YALI0E25201 ORF (SEQ ID NO: 27). The internal homologous fragments used to assemble the disruption constructs were ordered as synthetic DNA in the form of gBlocks (IDT) with a total length of 700 bp. 600 bp of these fragments are homologous to the targeted transporter YALI0E25201 and 50 bp to the vector backbone (5 and 3 connector sequence, FIG. 18) and HygB marker cassette (c and d connector sequence, FIG. 18). The HygB marker cassette was PCR amplified with suitable primers using Phusion polymerase (New England Biolabs) according to suppliers' instructions. The PCR product was purified and concentrated using NucleoSpin Gel and PCR Clean-up Kit (Machery Nagel).

The flanks and marker were assembled in the SnaBI/PmeI digested pRS417 5_3 shuttle vector backbone in-vivo by transforming both flanks, the HygB fragment and the linear pRS417 5_3 shuttle vector to *S. cerevisiae* CEN-PK-7D. See FIG. 18.

After transformation and recovery for 2 hours in YEPhD at 30° C. the cells were plated on YEPhD agar with 200 µg/ml G418 (Invitrogen). The plates were incubated at 30° C. for 2 days. Transformants were cultured in YEPD+200 µg/ml G418 at 30° C., 550 rpm and 80% humidity. Plasmid DNA was isolated and purified. Correct assembly of the disruption cassettes was established with diagnostic PCR.

Figure 19:
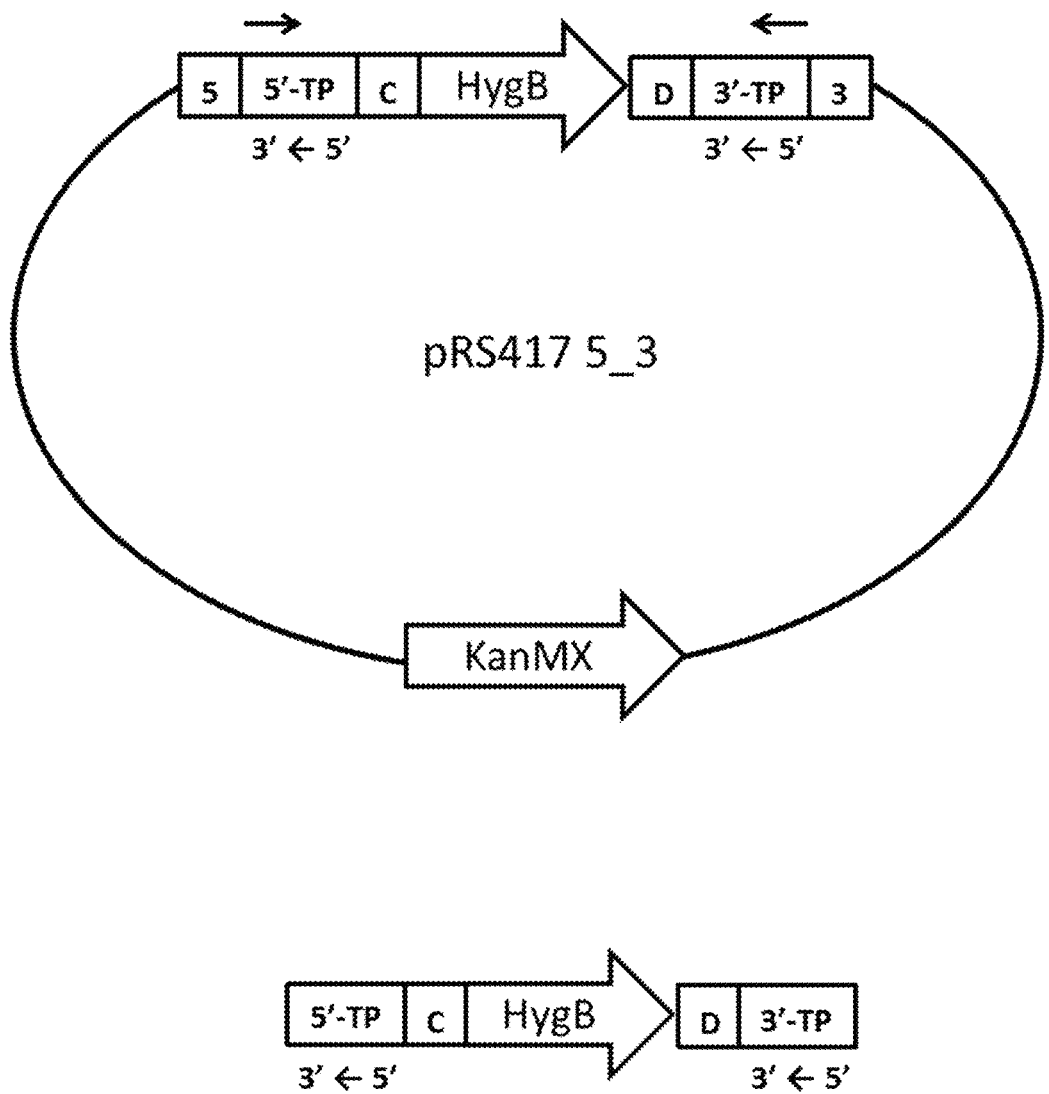
FIG. 19 sets out a schematic representation of the PCR amplification of the transporter disruption constructs off plasmid pRS417 5-3 containing the HYG marker and transporter internal fragments.
Figure 20:
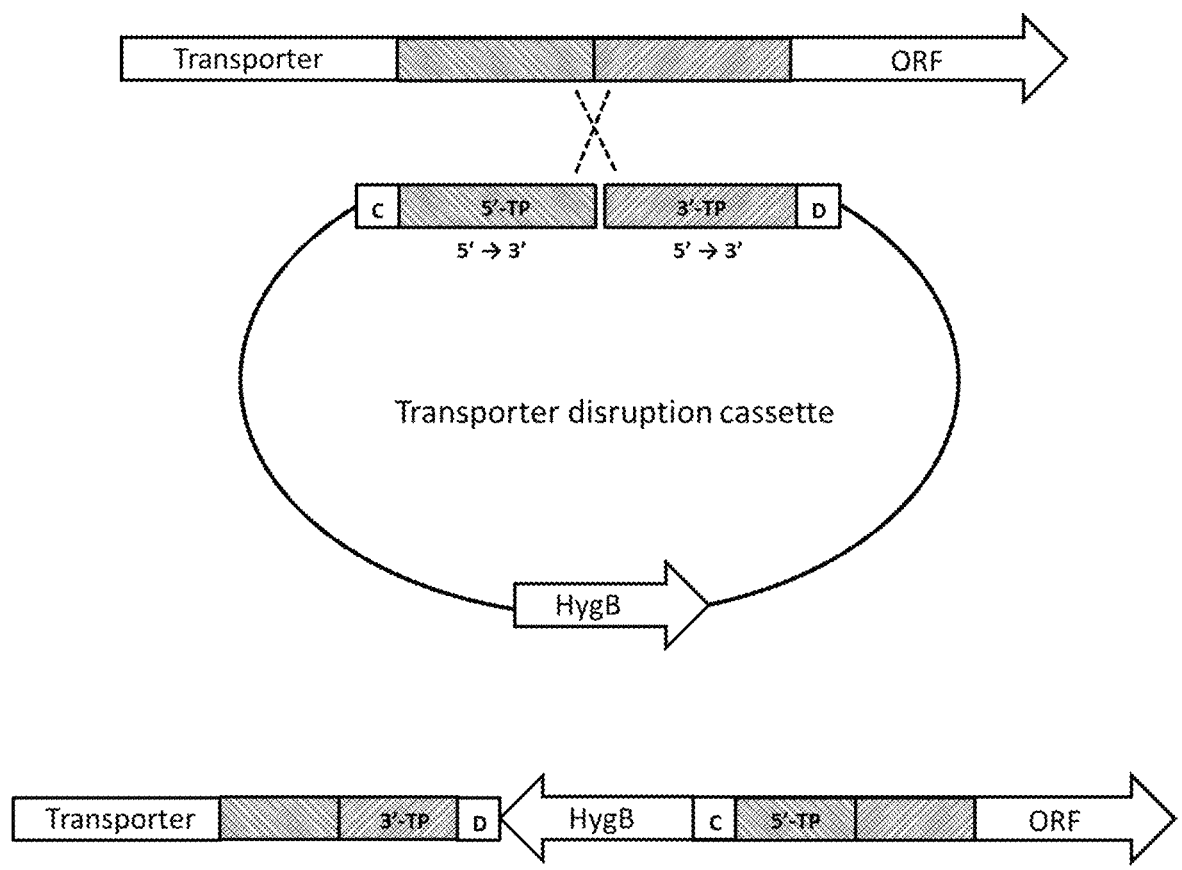
FIG. 20 sets out a schematic representation of the recombination event at the genome resulting in a disruption of the transporter gene and integration of the HygB marker.

The expression cassettes were PCR amplified (FIG. 19) in six 50 µl PCR reactions. The PCR product was purified and concentrated using NucleoSpin Gel and PCR Clean-up Kit (Machery Nagel). 1 µg of the PCR amplified disruption cassette was transformed to *Y. lipolytica* STV2049. After transformation and recovery for 2 hours in YEPhD at 30° C. the cells were plated on YEPhD agar with 100 µg/ml HygB (Invitrogen). The plates were incubated at 30° C. for 2 days. Transformants were purified by re-streaking them on YEPhD agar with 100 µg/ml HygB. Correct integration, as illustrated in FIG. 20, was established with diagnostic PCR using appropriate oligo's.

Example 12. Fermentation of *Y. lipolytica* STV2049 and STV2049 YALI0E25201 Disruption Transformants A pre-culture was inoculated with colony material from YEPh-D agar. The pre-culture was grown in 96-Half Deep Well Plate containing 200 µl 0.5×YEP with 2% glucose per well. The plates were sealed with a breathable seal and incubated in an Infors incubator at 30° C., 80% humidity, 750 rpm for 48 hours.

40 µl of the 96-well pre-culture was used to inoculate a 24-well deep well plate containing 2.5 ml of 0.25×YEP with 5% glucose per well. Plates were sealed with a breathable seal and incubated in an Infors incubator at 30° C., 80% humidity, 500 rpm for 120 hours.

The 24-well plates were spun down in an MTP centrifuge and 1 ml of the supernatant was harvested. The remaining supernatant was decanted from the pellet.

The supernatant fraction was diluted 1000 times in 33% Acetonitrile. The pellet was suspended in 2.5 ml milli-Q and 1 ml was transferred to a 96-well DWP. The plate was sealed with an aluminium seal and incubated for 10 minutes at 90° C. The plate was cooled down to room temperature and 0.5 ml of 100% Acetonitrile was added and homogenized. The plates were centrifuged at 2088×g for 10 minutes to pellet cell material and debris. The supernatant of the pellet fraction was diluted 33 times in 33% acetonitrile resulting in a combined 50 times dilution. Samples were analyzed for Rebaudioside A and other steviolglycosides using LC/MS.

We found that the strains that had the YALI0E25201 disruption produced lower titers of Rebaudioside A in the supernatant compared to the parent strain. The concentration of Rebaudioside A was approximately three fold lower in the transporter disruption strain compared to the parental strain (see Table 1).

TABLE 1

Rebaudioside A supernatant concentrations in 24-well fermentations. Six replicate cultures were performed for parent strain STV2049. Duplicate cultures of three independent STV2049 ΔYALI0E25201 transformants were performed. The averages are taken for the data in Table 1.

| Strain | RebA supernatant (mg/L) |
|---|---|
| STV2049 | 441 |
| STV2049 ΔYALI0E25201 A | 155 |

The observation that the concentration of Rebaudioside A in the supernatant is lower for the transporter disruption strain compared to the reference strain was also seen for Stevioside, Rubusoside, and to a lesser degree for Rebaudioside D and Steviol-19-monoside (see Tables 2 to 5).

TABLE 2

Stevioside supernatant concentrations in 24-well fermentations. Six replicate cultures were performed for parent strain STV2049. Duplicate cultures of three independent STV2049 ΔYALI0E25201 transformants were performed. The averages are taken for the data in Table 2.

| Strain | Stevioside supernatant (mg/L) |
|---|---|
| STV2049 | 144 |
| STV2049 ΔYALI0E25201 A | 46.9 |

TABLE 3

Rubusoside supernatant concentrations in 24-well fermentations. Six replicate cultures were performed for parent strain STV2049. Duplicate cultures of three independent STV2049 ΔYALI0E25201 transformants were performed. The averages are taken for the data in Table 3.

| strain | Rubusoside supernatant (mg/L) |
|---|---|
| STV2049 | 42.2 |
| STV2049 ΔYALI0E25201 A | 17.2 |

TABLE 4

Rebaudioside D supernatant concentrations in 24-well fermentations. Six replicate cultures were performed for parent strain STV2049. Duplicate cultures of three independent STV2049 ΔYALI0E25201 transformants were performed. The averages are taken for the data in Table 4.

| Strain | RebD supernatant (mg/L) |
|---|---|
| STV2049 | 39.7 |
| STV2049 ΔYALI0E25201 A | 32.6 |

TABLE 5

Steviol-19-monoside supernatant concentrations in 24-well fermentations. Six replicate cultures were performed for parent strain STV2049. Duplicate cultures of three independent STV2049 ΔYALI0E25201 transformants were performed. The averages are taken for the data in Table 5.

| Strain | Steviol-19-monoside supernatant (mg/L) |
|---|---|
| STV2049 | 35.7 |
| STV2049 ΔYALI0E25201 A | 20.2 |

The effect of disrupting the transporter gene was most pronounced on the transport of the aforementioned steviol glycosides, and not a consequence of a general decreased production of steviol glycosides. This is illustrated when the concentration of all steviol glycosides are measured in the pellet fraction (Table 6). Here it can be seen that in the YALI0E25201 disruption strain, the concentration of all steviol glycosides in the pellet fraction is increased in the transporter disruption strain, indicative of reduced transport.

TABLE 6

Concentration of the sum of all steviol glycosides (Rebaudioside A, Stevioside, Rebaudioside B, Rebaudioside D, Steviolbioside, Rubusoside, Steviol-19-monoside, Steviol-13-monoside and Rebaudioside M) in the pellet fraction in 24-well fermentations. Six replicate cultures were performed for parent strain STV2049. Duplicate cultures of three independent STV2049 ΔYALI0E25201 transformants were performed. The averages are taken for the data in Table 6.

| strain | Sum steviol glycosides pellet (uM) |
|---|---|
| STV2049 | 34 |
| STV2049 ΔYALI0E25201 A | 67 |

Example 13. Over-Expression of the YALI0E25201 Transporter in Steviol Glycosides Producing *Y. lipolytica* Strains To further demonstrate the functionality of the YALI0E25201 transporter, the YALI0E25201 ORF was assembled in an expression cassette with the *Y. lipolytica* YP006 promoter and *Y. lipolytica* TEF4 terminator. The cassettes were assembled in the pRS417 5_3 vector together with the Nourseothricin marker. As a negative control the same cassette only containing the Nourseothricin marker was constructed. The expression cassettes were PCR amplified and the obtained fragments were transformed to three different strains: strains STV2049 is a strain producing mostly RebA, and is described above. Also, the transporter deletion strain is included (STV2049 ΔYALI0E25201 (described above)). The third strain is STV2170, a strain producing mostly RebM. STV2170 was build similarly to strain STV2049, and the genotype is listed below in Table 7.

TABLE 7

Genotype of strain STV2170. Between brackets indicates the gene copy number present in the strain

| Strain name | genotype |
|---|---|
| STV2170 | tHMG (2; SEQ ID NO: 15) GGS (2; SEQ ID NO: 16) CarG (1; SEQ ID NO: 32) CPS (2 SEQ ID NO: 20) KS (2; SEQ ID NO: 21) KO_Gib (2; SEQ ID NO: 23), KAH4 (4; SEQ ID NO: 22) CPR3 (2; SEQ ID NO: 24) UGT1 (5; SEQ ID NO: 17) UGT2_6b (2; SEQ ID NO: 33) UGT3 (2; SEQ ID NO: 18) UGT4 (4; SEQ ID NO: 19) RT18 (1; SEQ ID NO: 34) |

Six transformants were selected for each combination of strain and expression cassette. The transformants were grown in 24-well fermentation and the supernatant- and pellet fractions were analyzed by LC-MS as described in Example 12.

TABLE 8

RebA supernatant and pellet concentrations in 24-well fermentations in the control strain (STV2049 with NatMX marker) and YALI0E25201 transporter over-expression strain (STV2049 with transporter and NatMX marker)

| Strain | RebA supernatant (mg/L) | RebA pellet (mg/L) |
|---|---|---|
| STV2049 control | 392 | 15 |
| YALI0E25201 O.E. | 461 | 15 |

These data illustrate that over-expression of the YALI0E25201 transporter has a positive effect on extracellular RebA production.

TABLE 9

RebM supernatant and pellet concentrations in 24-well fermentations in the control strain (STV2049 with NatMX marker) and YALI0E25201 transporter over-expression strain (STV2049 with transporter and NatMX marker)

| Strain | RebM supernatant (mg/L) | RebM pellet (mg/L) |
|---|---|---|
| STV2049 control | 59 | 10 |
| YALI0E25201 O.E. | 43 | 4 |

RebM production in this strain is low compared to RebA production, but even so, the effect of the transporter over-expression can be seen in the concentrations of RebM. As RebA is more efficiently exported to outside the cell in the YALI0E25201 over-expression strain, less RebA will be available for further glycosylation inside the cell, and hence resulting in lower production of RebM, particularly in the pellet fraction.

TABLE 10

RebA supernatant and pellet concentrations in 24-well fermentations in the transporter deletion strain (STV2049 ΔYALI0E25201 with NatMX marker) and the same background with the YALI0E25201 transporter over-expressed (STV2049 ΔYALI0E25201 with transporter and NatMX marker.)

| Strain | RebA supernatant (mg/L) | RebA pellet (mg/L) |
|---|---|---|
| STV2049 ΔYALI0E25201 control | 114 | 23 |
| STV2049 ΔYALI0E25201 YALI0E25201 O.E. | 431 | 17 |

Upon over-expression of the YALI0E25201 transporter in the YALI0E25201 deletion strain, the extracellular production of RebA is greatly enhanced, and restored to similar levels as the reference strain without the transporter deletion.

TABLE 11

RebM supernatant and pellet concentrations in 24-well fermentations in the transporter deletion strain (STV2049 ΔYALI0E25201 with NatMX marker) and the same background with the YALI0E25201 transporter over-expressed (STV2049 ΔYALI0E25201 YALI0E25201 O.E.)

| Strain | RebM supernatant (mg/L) | RebM pellet (mg/L) |
|---|---|---|
| STV2049 ΔYALI0E25201 control | 6 | 45 |
| STV2049 ΔYALI0E25201 YALI0E25201 O.E. | 22 | 1 |

In the transporter deletion strain, steviol glycosides including RebA accumulate in the cell, allowing for continued glycosylation inside the cell. As a consequence, RebM concentrations may increase. In the transporter deletion strain, the concentration RebM in the pellet fraction is much higher than in the supernatant. Upon restoring transport this is reversed: less accumulation of intracellular RebM, and more export of RebM.

TABLE 12

RebA supernatant and pellet concentrations in 24-well fermentations in the RebM production control strain (STV2170 with NatMX marker) and YALI0E25201 transporter over-expression strain (STV2170 with transporter and NatMX marker)

| Strain | RebA supernatant (mg/L) | RebA pellet (mg/L) |
|---|---|---|
| STV2170 control | 107 | 22 |
| STV2170 YALI0E25201 O.E. | 283 | 8 |

Over-expression of the YALI0E25201 transporter results in greatly increased extracellular production of RebA, and greatly reduced accumulation of RebA in the pellet.

TABLE 13

RebM supernatant and pellet concentrations in 24-well fermentations in the RebM production control strain (STV2170 with NatMX marker) and YALI0E25201 transporter over-expression strain (STV2170 with transporter and NatMX marker)

| Strain | RebM supernatant (mg/L) | RebM pellet (mg/L) |
|---|---|---|
| STV2170 control | 631 | 132 |
| STV2170 YALI0E25201 O.E. | 660 | 61 |

Over-expression of the YALI0E25201 transporter results in increased extracellular production of RebM, and reduced accumulation of RebM in the pellet.

Together these data illustrate that over-expression of the YALI0E25201 transporter has a positive effect on extracellular RebA and RebM production. Not only is the distribution of RebA and RebM production in the supernatant fraction versus the pellet fraction favourable when the transporter is over-expressed, over-expression of the YALI0E25201 transporter also has a positive effect on the total amount of RebA and RebM production.

TABLE 14

Description of the sequence listing

| SEQ ID NO | Description | SEQ ID NO | Description |
| --- | --- | --- | --- |
| SEQ ID NO: 1 | UGT2_1a CpO for *Y. lipolytica* | SEQ ID NO: 18 | UGT3 CpO for *Y. lipolytica* |
| SEQ ID NO: 2 | PGM promoter from *Y. lipolytica* | SEQ ID NO: 19 | UGT4 CpO for *Y. lipolytica* |
| SEQ ID NO: 3 | HSP promoter from *Y. lipolytica* | SEQ ID NO: 20 | tCPS from *S. rebaudiana* CpO for *Y. lipolytica* |
| SEQ ID NO: 4 | HYPO promoter from *Y. lipolytica* | SEQ ID NO: 21 | tKS from *S. rebaudiana* CpO for *Y. lipolitica* |
| SEQ ID NO: 5 | ENO promoter from *Y. lipolytica* | SEQ ID NO: 22 | KAH_4 CpO for *Y. lipolitica* |
| SEQ ID NO: 6 | CWP promoter from *Y. lipolytica* | SEQ ID NO: 23 | KO from *Gibberella fujikori* CpO for *Y. lipolytica* |
| SEQ ID NO: 7 | TPI promoter from *Y. lipolytica* | SEQ ID NO: 24 | CPR_3 CpO for *Y. lipolytica* |
| SEQ ID NO: 8 | YP001 promoter from *Y. lipolytica* | SEQ ID NO: 25 | UGT2_10b CpO for *Y. lipolytica* |
| SEQ ID NO: 9 | Xpr terminator from *Y. lipolytica* | SEQ ID NO: 26 | YALI0C08701 WT CDS |
| SEQ ID NO: 10 | Cwp terminator from *Y. lipolytica* | SEQ ID NO: 27 | YALI0E25201 WT CDS |
| SEQ ID NO: 11 | Gpd terminator from *Y. lipolytica* | SEQ ID NO: 28 | YALI0E25201 CpO for *Y. lipolytica* |
| SEQ ID NO: 12 | Pgm terminator from *Y. lipolytica* | SEQ ID NO: 29 | YALI0E25201 WT from *Y. lipolytica* |
| SEQ ID NO: 13 | Pgk terminator from *Y. lipolytica* | SEQ ID NO: 30 | YP006 promoter from *Y. lipolytica* |
| SEQ ID NO: 14 | act1T terminator from *Y. lipolytica* | SEQ ID NO: 31 | Tef4 terminator from *Y. lipolytica* |
| SEQ ID NO: 15 | tHMG CpO for *Y. lipolitica* | SEQ ID NO: 32 | CarG codon optimized for *Y. lipolytica* |
| SEQ ID NO: 16 | GGS CpO for *Y. lipolytica* | SEQ ID NO: 33 | UGT2_6b CpO for *Y. lipolytica* |
| SEQ ID NO: 17 | UGT1 CpO for *Y. lipolytica* | SEQ ID NO: 34 | RT18 CpO for *Y. lipolytica* |

What is claimed is:

1. A recombinant host capable of producing a steviol glycoside which overexpresses a polypeptide which mediates steviol glycoside transport and which polypeptide comprises the amino acid sequence set forth in SEQ ID NO:29 or an amino acid sequence having at least about 95% sequence identity thereto, wherein the recombinant host comprises one or more recombinant nucleic acid sequence encoding:
   (i) a polypeptide having UDP-glycosyltransferase 74G1 (UGT74G1) activity;
   (ii) a polypeptide having UDP-glycosyltransferase 2 (UGT2) activity;
   (iii) a polypeptide having UDP-glycosyltransferase 85C2 (UGT85C2) activity; and
   (iv) a polypeptide having UDP-glycosyltransferase 76G1 (UGT76G1) activity.

2. A recombinant host capable of producing a steviol glycoside which overexpresses a polypeptide which mediates steviol glycoside transport and which polypeptide comprises the amino acid sequence set forth in SEQ ID NO:29 or an amino acid sequence having at least about 95% sequence identity thereto, wherein the recombinant host comprises one or more recombinant nucleic acid sequence encoding:
   (i) a polypeptide having UDP-glycosyltransferase 74G1 (UGT74G1) activity;
   (ii) a polypeptide having UDP-glycosyltransferase 2 (UGT2) activity;
   (iii) a polypeptide having UDP-glycosyltransferase 85C2 (UGT85C2) activity;
   (iv) a polypeptide having UDP-glycosyltransferase 76G1 (UGT76G1) activity;
   (v) a polypeptide having ent-copalyl pyrophosphate synthase activity;
   (vi) a polypeptide having ent-Kaurene synthase activity;
   (vii) a polypeptide having ent-Kaurene oxidase activity;
   (viii) a polypeptide having kaurenoic acid 13-hydroxylase activity.

3. The recombinant host of claim 1, comprising a recombinant nucleic acid which encodes a polypeptide comprising the amino acid sequence set forth in SEQ ID NO:29 or an amino acid sequence having at least about 95% sequence identity thereto.

4. The recombinant host of claim 1, comprising one or more recombinant nucleotide sequence(s) encoding:
- a polypeptide having ent-copalyl pyrophosphate synthase activity;
- a polypeptide having ent-Kaurene synthase activity;
- a polypeptide having ent-Kaurene oxidase activity; and
- a polypeptide having kaurenoic acid 13-hydroxylase activity.

5. The recombinant host of claim 1, comprising a recombinant nucleic acid sequence encoding a polypeptide having NADPH-cytochrome p450 reductase activity.

6. The recombinant host of claim 1, wherein the host belongs to one of the genera *Saccharomyces, Aspergillus, Pichia, Kluyveromyces, Candida, Hansenula, Humicola, Issatchenkia, Trichosporon, Brettanomyces, Pachysolen, Yarrowia, Yamadazyma* or *Escherichia*.

7. The recombinant host of claim 5, wherein the recombinant host is a *Saccharomyces cerevisiae* cell, a *Yarrowia lipolytica* cell, a *Candida krusei* cell, or an *Escherichia coli* cell.

8. The recombinant host of claim 1, wherein the ability of the host to produce geranylgeranyl diphosphate (GGPP) is upregulated.

9. The recombinant host of claim 1, comprising a nucleic acid sequence encoding one or more of:
- a polypeptide having hydroxymethylglutaryl-CoA reductase activity; or
- a polypeptide having farnesyl-pyrophosphate synthetase activity.

10. A process for the preparation of a steviol glycoside which comprises fermenting the recombinant host of claim 1 in a suitable fermentation medium and, optionally, recovering the steviol glycoside.

11. The process of claim 10, wherein the process is carried out on an industrial scale.

12. A fermentation broth comprising the recombinant host of claim 1.

13. The fermentation broth of claim 12, further comprising a steviol glycoside obtainable by fermenting, in a suitable fermentation medium, a recombinant host capable of producing a steviol glycoside which overexpresses a polypeptide which mediates steviol glycoside transport and which polypeptide comprises the amino acid sequence set forth in SEQ ID NO:29 or an amino acid sequence having at least about 95% sequence identity thereto, wherein the recombinant host comprises one or more recombinant nucleic acid sequence encoding:
- (i) a polypeptide having UGT74G1 activity;
- (ii) a polypeptide having UGT2 activity;
- (iii) a polypeptide having UGT85C2 activity; and
- (iv) a polypeptide having UGT76G1 activity.

* * * * *